(12) United States Patent  
Rothstein et al.

(10) Patent No.: US 7,060,457 B2
(45) Date of Patent: Jun. 13, 2006

(54) ABERRANT GLUTAMATE TRANSPORTERS AND METHODS OF USE

(75) Inventors: Jeffrey D. Rothstein, Baltimore, MD (US); Chieng-Liang Glenn Lin, Baltimore, MD (US); Lynn A. Bristol, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/040,736

(22) Filed: Mar. 18, 1998

(65) Prior Publication Data

US 2003/0060617 A1  Mar. 27, 2003

(51) Int. Cl.
 C12N 15/00 (2006.01)
 C12N 1/20 (2006.01)
 C12N 15/63 (2006.01)
 C07H 21/04 (2006.01)

(52) U.S. Cl. ............... 435/69.1; 435/320.1; 435/252.1; 536/23.1

(58) Field of Classification Search ...... 536/23.1–23.6; 435/252.3, 320.1, 69.1; 514/44; 530/300, 530/350
See application file for complete search history.

(56) References Cited

U.S. PATENT DOCUMENTS 5,631,134 A   5/1997  Cantor ...................... 435/91.1
5,643,729 A   7/1997  Taniguchi et al. .......... 435/91.2
5,658,782 A * 8/1997  Amara
5,660,979 A   8/1997  Romano et al. ........... 435/91.2

OTHER PUBLICATIONS

Arriza et al, J. Neurosci, 14:5559-69, 1994.*
Crouhe et al Antisenn & Nuc. Acid Drug Dev. 8:115-22, 1998.*
Gura T., Science, 270, Oct. 27, 1995.*
Skolnick et al., Trends in Biotech 18(1):34-39, 2000.*
Sambrook et al., Molecular Cloning, Cold Spring Harbor Lab. Press, 1989, pp. 9.47-9.51, 11.48-11.49.*
M. Johnston, Current Biology, pp. R171-174 (1998).
J. Rothstein, et al., New. Eng. Jour. Med., pp. 1464-1468 (1992).
J. Rothstein, et al., Amer. Nuro. Assoc., pp. 73-84 (1995).
L. Bristol, J. Rothstein, Amer. Nuro. Assoc., pp. 676-679 (1996).
U. Fischer, et al., Cell, pp. 1023-1029 (1997).
Q. Liu, et al., Cell, pp. 1013-1021 (1997).
D. Trotti, et al., Communication, pp. 5976-5979 (1996).
A. Volterra, et al., Molecular Pharmacology, pp. 986-992 (1994).
S. Li, et al., Jour. of Neuropathology and Exper. Neurology, pp. 901-911 (1997).

* cited by examiner

*Primary Examiner*—Sharon Turner
(74) *Attorney, Agent, or Firm*—Drinker Biddle & Reath LLP

(57) ABSTRACT

In one aspect, the present invention features methods for detecting at least one neurological disorder in a patient, the method comprising obtaining a biological sample from the patient; and detecting at least one aberrant human glutamate transporter 2 (EAAT 2) mRNA in the sample as being indicative of the neurological disorder in the patient. In a particular aspect, the invention is useful for detecting amyotrophic lateral sclerosis (ALS) in the patient.

7 Claims, 28 Drawing Sheets

FIG. 1

| FIG. 1A |
|---------|
| FIG. 1B |
| FIG. 1C |

SEQ ID NO: 1
                                                                             2

1/1                            31/11                        61/21
gat agt gct gaa gag ggg cgt tcc cag acc atg gca tct acg gaa ggt gcc aac aat atg ccc aag cag gtg gaa gtg cga atg cca
                                 M   A   S   T   E   G   A   N   N   M   P   K   Q   V   E   V   R   M   P
91/31                          121/41                       151/51
gac agt cat ctt ggc tca gag gag ccc aag cac cgg ctg cgc cac ctg ctg ggg aag aat ctg ctc acc ctg
 D   S   H   L   G   S   E   E   P   K   H   R   H   L   G   L   R   H   L   L   G   K   N   L   L   T   L
181/61                         211/71                       241/81
acg gtg ttt ggt gtc atc ctg gga gca gtg tgt ggt ctt ctt cgc ttg gca tct ccc atc cac cct gat gtg gtt atg tta ata gcc
 T   V   F   G   V   I   L   G   A   V   C   G   L   L   R   L   A   S   P   I   H   P   D   V   V   M   L   I   A
271/91                         301/101                      331/111
ttc cca ggg gat ata ctc atg agg atg cta aaa atg ctc att ctc cct cta atc tcc agc tta atc aca ggg ttg tca ggc ctg gat
 F   P   G   D   I   L   M   R   M   L   K   M   L   I   L   P   L   I   S   S   L   I   T   G   L   S   G   L   D
361/121                        391/131                      421/141
gct aag gct agt ggc cgc ttg ggc acg aga gcc atg gtg tat tac atg tcc acg acc atc att gct gca gta ctg gca gtc ctg gtc
 A   K   A   S   G   R   L   G   T   R   A   M   V   Y   Y   M   S   T   T   I   I   A   A   V   L   G   V   L   V
451/151                        481/161                      511/171
ttg gct atc cat cca ggc aat ccc aag ctc aag aag aag cag ctg ggg cct ggg aag aat gat gaa gtg tcc agc ctg gat gcc ttc ctg
 L   A   I   H   P   G   N   P   K   L   K   K   K   Q   L   G   P   G   K   N   D   E   V   S   S   L   D   A   F   L

FIG. 1A

```
541/181
gac ctt att cga aat ctc ttc cct gaa aac ctt gtc caa gcc tgc ttt caa cag att caa aca gtg acg aag aaa gtc ctg gtt gca cca
 D   L   I   R   N   L   F   P   E   N   L   V   Q   A   C   F   Q   Q   I   Q   T   V   T   K   K   V   L   V   A   P
571/191                                                  601/201
631/211                                                                                  691/231
ccg cca gac gag gag gcc aac gca acc agc gct gaa gtc tct ctg ttg aac gag act gtg act gag gtg ccg gag gag act aag atg gtt
 P   P   D   E   E   A   N   A   T   S   A   E   V   S   L   L   N   E   T   V   T   E   V   P   E   E   T   K   M   V
721/241                                                  751/251                                                  781/261
atc aag aag ggc ctg gag ttc aag gat ggg atg aac gtc tta ggt ctg ata ggg ttt ttc att gct ttt ggc ata gct atg ggg aag atg
 I   K   K   G   L   E   F   K   D   G   M   N   V   L   G   L   I   G   F   F   I   A   F   G   I   A   M   G   K   M
811/271                                                  841/281                                                  871/291
gga gat cag gcc aag ctg atg gtg gat ttc aac att ttg aat gag att gta atg aag tta gaa gtg gtt gct agg caa ctg ggg atg tac
 G   D   Q   A   K   L   M   V   D   F   N   I   L   N   E   I   V   M   K   L   E   V   V   A   R   Q   L   G   M   Y
901/301                                                  931/311                                                  961/321
ctg ggt atc gcc tgc ctg atc atc cac ggg ggc atc ttc ctg cca ctc ttc tac ttt gta gtg acc agg aaa aac ccc ttc tcc ctt ttt
 L   G   I   A   C   L   I   I   H   G   G   I   F   L   P   L   I   Y   F   V   V   T   R   K   N   P   F   S   L   F
991/331                                                  1021/341                                                 1051/351
gtc atc ata ggc atc atc atc cac ggg ggc atc ttc ctg cca ctc ttc tac ttt gta gtg acc agg aaa aac ccc ttc tcc ctt ttt gct
 V   I   I   G   I   I   I   H   G   G   I   F   L   P   L   I   Y   F   V   V   T   R   K   N   P   F   S   L   F   A
1081/361                                                 1111/371                                                 1141/381
ggc att ttc caa gct tgg atc act gcc ctg ggc acc ctg cct gtc acc ttt cgt tgc ctg gaa gaa aat ctg
 G   I   F   Q   A   W   I   T   A   L   G   T   A   S   A   G   T   L   P   V   T   F   R   C   L   E   E   N   L
```

FIG. 1B

1171/391
ggg att gat aag cgt gtg act aga ttc gtc ctt cct gtt gga gca acc att aac atg gat ggt aca gcc ctt tat gaa gcg gtg gcc gcc
 G   I   D   K   R   V   T   R   F   V   L   P   V   G   A   T   I   N   M   D   G   T   A   L   Y   E   A   V   A   A
1261/421                                                                            1321/441
atc ttt ata gcc caa atg aat ggt gtt gtc ctg gat gga cag att gtg act gta agc ctc aca gcc acc ctg gca agc gtc ggc gcg
 I   F   I   A   Q   M   N   G   V   V   L   D   G   Q   I   V   T   V   S   L   T   A   T   L   A   S   V   G   A
1351/451                                                            1411/471
gcc agt atc ccc agt gcc ggg ctg gtc acc atg ctc ctc att ctg aca gcc ggc ctg cca aca gag gac atc agc ttg ctg gtg gct
 A   S   I   P   S   A   G   L   V   T   M   L   L   I   L   T   A   V   G   L   P   T   E   D   I   S   L   L   V   A
1441/481                                                1501/501
gtg gac tgg ctg ctg gac agg atg aga act tca gtc aat gtt gtg ggt gac tct ttt ggg gct gga ata gtc tat cac ctc tcc aag tct
 V   D   W   L   L   D   R   M   R   T   S   V   N   V   V   G   D   S   F   G   A   G   I   V   Y   H   L   S   K   S
1531/511                                1591/531
gag ctg gat acc att gac tcc cag cat gaa gtg cat cga gtg cat gaa gat att gaa atg acc aag act caa tcc att tat gat gac atg aag aac cac
 E   L   D   T   I   D   S   Q   H   E   V   H   R   V   H   E   D   I   E   M   T   K   T   Q   S   I   Y   D   D   M   K   N   H
1621/541                                                                            1681/561
agg gaa agc aac tct aat caa tgt gct gca cac aac tct gtc ata gta gat gaa tgc aag gta act ctg gca gcc aat gga aag
 R   E   S   N   S   N   Q   C   V   A   A   H   N   S   V   I   V   D   E   C   K   V   T   L   A   A   N   G   K
1711/571                                                1771/591
tca gcc gac tgc agt gtt gag gaa cct tgg aaa cgt gag aaa taa gga tat gag tct cag caa att ctt gaa taa act ccc cag cgt
 S   A   D   C   S   V   E   E   P   W   K   R   E   K   *

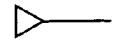 intron

| FIG. 2A |
|---------|
| FIG. 2B |

FIG. 2A

```
                                                                                              SEQ ID NO:
1   GGCAACTGGGG ATG TAC ATG GTA ACA GTG ATC ATA GGC CTC ATC ATC CAC GGG GGC ATC TTT CTC         79    3
1              Q  L  G  M  Y  M  V  T  V  I  I  G  L  I  I  H  G  G  I  F  L                  18    4

80  CCC TTG ATT TAC TTT GTA GTG ACC AGG AAA AAC CCC TTC TCC TGT GGT GGC ATT TTC CAA GCT TGG ATC ACT   154
19  P   L   I   Y   F   V   V   T   R   K   N   P   F   S   C   G   G   I   F   Q   A   W   I   T    43

155 GCC CTG GGC ACC GCT TCC AGG TAG AGAACAAAGAAATCACCTTTCTCTTGCTCACTCTGGCCCCTCTTTGCCATTCTCATTCTCAACCC  246
44  A   L   G   T   A   S   R    *                                                                    51
                                 └→ intron 7

247 CCTCCCATCACAAAGTTCAATAAGAACACTTGGCACACACATTACTTGATCTTTTGAAAGGCGA ATG ATT TGA AATTTTGTCTCCTTCTAGGAACT  342
1                                                                                                       3

343 TCTGAGCCTTCTGTGTGAACATTTTTGCTGGTTTGCAACTATATTGGAAATACGATCTCACATTAAATTTTTCAGATAA ATG CAT GCT ATT TGT  435
1                                                                                                       5

436 TTG CAT GCC TAA TTTGCCACTTAAATCATTAGTTAGTTTTAG ATG TTT TCT AAA GGG AGT GTA ACA GGA TAT TTT TCA ATA  517
6                                                                                                       13

518 AAC ATT TCA CCT GTG ATT TGG AAA ATG CTA TCA CAA AAT ATT ACT CTT TGA AGATTTTGGTAAATACATTTTCAAAAGTAGGA  600
14                                                                                                       30
```

```
601 GAAGCAGCTTTTACAAAGTAA ATG GTA TGT TAG GTGAGACTTTTTCTAACAAAATTCGGCCAAGTCTTTGACCTGACACGAACCTCTA ATG    692
      1                                                                                                   1

693 GAT TAT TTT TCC CCA GAG TTA ACT TGT CAT TGA TGAAGAATCAGTTCCCCCTTTGTTACTTAGTTCCAGTACCTAGAAAGCCAAAGAGG  781
      2                                                                                                  12

782 ACCCCAGAGAT ATG TAG AGAAAAATCATTTTTTGGACTATCATCTTGGACTGAATCTAACAAAAACAAACAAACAA ATG AAC AAG AAG AAA   872
      1                                                                                                   5

873 TAC ATA AGA AAC GTC TTA CAA TTA GGC TGG GCG CAG TAG CTC ATG CTT GTA ATC CCA GCA CTT TGG GAG GCC TCG   947
      6                                                                                                  11

948 GCA GGC GGA TCA CTT GAA GTC AGG AGT TCG AGG CCA GCC TGG CTA ACA TGG TGA AACCCCGTCTCTCCTAAAAAACAAAAA  1029
     12                                                                                                  29

1030 TTAACCAGTGCGGTGGGGGCGCCTATAATCCAGCTATTCGGTAGTCTGTGTCAGGAGAATTGCTTGAACCTAGGAGGCAGAGGTTGCAGTGAGCTGA  1129

1130 GATTGCATCACTGCACTCTAGTCTCGGGTGGCAAAGTGAGGCTCCATCTGTAAAAAAAAAAAAAAAA                                1196
```

FIG. 2B

SEQ ID NO:
5  1 gatagtgctg aagaggaggg gcgttcccag accatggcat ctacggaagg tgccaacaat
   61 atgcccaagc aggtggaagt gcgaatgcca gacagtcatc ttggctcaga ggaacccaag
  121 caccggcacc tgggcctgcg cctgtgtgac aagctgggga agaatctgct gctcaccctg
  181 acggtgtttg gtgtcatcct gggagcagtg tgtggagggc ttcttcgctt ggcatctccc
  241 atccaccctg atgtggttat gttaatagcc ttcccagggg atatactcat gaggatgcta
  301 aaaatgctca ttctccctct aatcatctcc agcttaatca cagggttgtc aggcctggat
  361 gctaaggcta gtggccgctt gggcacgaga gccatggtgt attacatgtc cacgaccatc
  421 attgctgcag tactgggggt cattctggtc ttggctatcc atccaggcaa tcccaagctc
  481 aagaagcagc tggggcctgg gaagaagaat gatgaagtgt ccagcctgga tgccttcctg
  541 gaccttattc gaaatctctt ccctgaaaac cttgtccaag cctgctttca acagattcaa
  601 acagtgacga agaaagtcct ggttgcacca ccgccagacg aggaggccaa cgcaaccagc
  661 gctgaagtct ctctgttgaa cgagactgtg actgaggtgc cggaggagac taagatggtt
  721 atcaagaagg gcctggagtt caaggatggg atgaacgtct taggtctgat agggttttc
  781 attgcttttg gcatcgctat ggggaagatg ggagatcagg ccaagctgat ggtggatttc
  841 ttcaacattt tgaatgagat tgtaatgaag ttagtgatca tgatcatgtg gtactctccc
  901 ctgggtatcg cctgcctgat ctgtggaaag atcattgcaa tcaaggactt agaagtggtt
  961 gctaggcaac tggggatgta catggtaaca gtgatcatag gcctcatcat ccacggggc
 1021atctttctcc ccttgattta ctttgtagtg accaggaaaa acccttctc ccttttgct
 1081ggcattttcc aagcttggat cactgccctg ggcaccgctt ccagtgctgg aactttgcct
 1141gtcacctttc gttgcctgga agaaaatctg gggattgata agcgtgtgac tagattcgtc
 1201cttcctgttg gagcaaccat taacatggat ggtacagccc tttatgaagc ggtggccgcc
 1261atctttatag cccaaatgaa tggtgttgtc ctggatggag gacagattgt gactgtaag▼
ggacag gatgagaact tcagtcaatg ttgtgggtga ctcttttggg
gctgggatag tctatcacct ctccaagtct gagctggata ccattgactc ccagcatcga
gtgcatgaag atattgaaat gaccaagact caatccattt atgatgacat gaagaaccac
agggaaagca actctaatca atgtgtctat gctgcacaca actctgtcat agtagatgaa
tgcaaggtaa ctctggcagc caatggaaag tcagccgact gcagtgttga ggaagaacct
tggaaacgtg agaaataagg atatgagtct cagcaaattc ttgaataaac tccccagcgt ▼ - splice junction

FIG. 3

SEQ ID NO:
6

▼tttatag cccaaatgaa tggtgttgtc ctggatggag gacagattgt gactgtaagc
ctcacagcca ccctggcaag cgtcggcgcg gccagtatcc ccagtgccgg gctggtcacc
atgctcctca ttctgacagc cgtgggcctg ccaacagagg acatcagctt gctggtggct
gctgggatag tctatcacct ctccaagtct gagctggata ccattgactc ccagcatcga
gtgcatgaag atattgaaat gaccaagact caatccattt atgatgacat gaagaaccac
agggaaagca actctaatca atgtgtctat gctgcacaca actctgtcat agtagatgaa
tgcaaggtaa ctctggcagc caatggaaag tcagccgact gcagtgttga ggaagaacct
tggaaacgtg agaaataagg atatgagtct cagcaaattc ttgaataaac tccccagcgt ▼ - splice junction

FIG. 4

SEQ ID NO:
7

▼tttatag cccaaatgaa tggtgttgtc ctggatggag gacagattgt gactgtaagc
ctcacagcca ccctggcaag cgtcggcgcg gccagtatcc ccagtgccgg gctggtcacc
atgctcctca ttctgacagc cgtgggcctg ccaacagagg acatcagctt gctggtggct
gctgggatag tctatcacct ctccaagtct gagctggata ccattgactc ccagcatcga
gtgcatgaag atattgaaat gaccaagact caatccattt atgatgacat gaagaaccac
agggaaagca actctaatca atgtgtctat gctgcacaca actctgtcat agtagatgaa
tgcaaggtaa ctctggcagc caatggaaag tcagccgact gcagtgttga ggaagaacct
tggaaacgtg agaaataagg atatgagtct cagcaaattc ttgaataaac tccccagcgt ▼ - splice junction

FIG. 5

SEQ ID NO:
 8 1 gatagtgctg aagaggaggg gcgttcccag accatggcat ctacggaagg tgccaacaat
   61 atgcccaagc aggtggaagt gcgaatc cacgaccatc
      attgctgcag tactgggggt cattctggtc ttggctatcc atccaggcaa tcccaagctc
      aagaagcagc tggggcctgg gaagaagaat gatgaagtgt ccagcctgga tgccttcctg
      gaccttattc gaaatctctt ccctgaaaac cttgtccaag cctgctttca acagattcaa
      acagtgacga agaaagtcct ggttgcacca ccgccagacg aggaggccaa cgcaaccagc
      gctgaagtct ctctgttgaa cgagactgtg actgaggtgc cggaggagac taagatggtt
      atcaagaagg gcctggagtt caaggatggg atgaacgtct taggtctgat agggttttc
      attgcttttg gcatcgctat ggggaagatg ggagatcagg ccaagctgat ggtggatttc
      ttcaacattt tgaatgagat tgtaatgaag ttagtgatca tgatcatgtg gtactctccc
      ctgggtatcg cctgcctgat ctgtggaaag atcattgcaa tcaaggactt agaagtggtt
      gctaggcaac tggggatgta catggtaaca gtgatcatag gcctcatcat ccacggggc
      atctttctcc ccttgattta ctttgtagtg accaggaaaa acccctctc ccttttgct
      ggcattttcc aagcttggat cactgccctg gcaccgcctt ccagtgctgg aactttgcct
      gtcaccttc gttgcctgga agaaaatctg gggattgata agcgtgtgac tagattcgtc
      cttcctgttg gagcaaccat taacatggat ggtacagccc tttatgaagc ggtggccgcc
      atctttatag cccaaatgaa tggtgttgtc ctggatggag gacagattgt gactgtaagc
      ctcacagcca ccctggcaag cgtcggcgcg gccagtatcc ccagtgccgg gctggtcacc
      atgctcctca ttctgacagc cgtgggcctg ccaacagagg acatcagctt gctggtggct
      gtggactggc tgctggacag gatgagaact tcagtcaatg ttgtgggtga ctcttttggg
      gctgggatag tctatcacct ctccaagtct gagctggata ccattgactc ccagcatcga
      gtgcatgaag atattgaaat gaccaagact caatccattt atgatgacat gaagaaccac
      agggaaagca actctaatca atgtgtctat gctgcacaca actctgtcat agtagatgaa
      tgcaaggtaa ctctggcagc caatggaaag tcagccgact gcagtgttga ggaagaacct
      tggaaacgtg agaaataagg atatgagtct cagcaaattc ttgaataaac tccccagcgt ▼ - splice junction

FIG. 6

SEQ ID NO:
```
9   1 gatagtgctg aagaggaggg gcgttcccag accatggcat ctacggaagg tgccaacaat
   61 atgcccaagc aggtggaagt gcgaatgcca gacagtcatc ttggctcaga ggaacccaag
  121 caccggcacc tgggcctgcg cctgtgtgac aagctgggga agaatctgct gctcaccctg
  181 acggtgtttg gtgtcatcct gggagcagtg tgtggagggc ttcttcgctt ggcatctccc
  241 atccaccctg atgtggttat gttaatagcc ttcccagggg atatactcat gaggatgcta
  301 aaaatgctca ttctccctct aatcatctcc agcttaatca cagggttgtc aggcctggat
  361 gctaaggcta gtggccgctt gggcacgaga gccatggtgt attacatgtc cacgaccatc
  421 attgctgcag tactgggggt catt▼ctggtcacc
       atgctcctca ttctgacagc cgtgggcctg ccaacagagg acatcagctt gctggtggct
       gtggactggc tgctggacag gatgagaact tcagtcaatg ttgtgggtga ctcttttggg
       gctgggatag tctatcacct ctccaagtct gagctggata ccattgactc ccagcatcga
       gtgcatgaag atattgaaat gaccaagact caatccattt atgatgacat gagaaccac
       agggaaagca actctaatca atgtgtctat gctgcacaca actctgtcat agtagatgaa
       tgcaaggtaa ctctggcagc caatggaaag tcagccgact gcagtgttga ggaagaacct
       tggaaacgtg agaataagg atatgagtct cagcaaattc ttgaataaac tccccagcgt
```

▼ - splice junction

FIG. 7

SEQ ID NO:
10      AGCCCCGCAGCAAAGCACAG▼gtggatttc
   841  ttcaacattt tgaatgagat tgtaatgaag ttagtgatca tgatcatgtg gtactctccc
   901  ctgggtatcg cctgcctgat ctgtggaaag atcattgcaa tcaaggactt agaagtggtt
   961  gctaggcaac tggggatgta catggtaaca gtgatcatag gcctcatcat ccacgggggc
  1021  atctttctcc ccttgattta ctttgtagtg accaggaaaa accccttctc ccttttttgct
  1081  ggcattttcc aagcttggat cactgccctg gcaccgctt ccagtgctgg aactttgcct
  1141  gtcacctttc gttgcctgga agaaaatctg gggattgata agcgtgtgac tagattcgtc
  1201  cttcctgttg gagcaaccat taacatggat ggtacagccc tttatgaagc ggtggccgcc
  1261  atctttatag cccaaatgaa tggtgttgtc ctggatggag gacagattgt gactgtaagc
  1321  ctcacagcca ccctggcaag cgtcggcgcg gccagtatcc ccagtgccgg gctggtcacc
  1381  atgctcctca ttctgacagc cgtgggcctg ccaacagagg acatcagctt gctggtggct
  1441  gtggactggc tgctggacag gatgagaact tcagtcaatg ttgtgggtga ctcttttggg
  1501  gctgggatag tctatcacct ctccaagtct gagctggata ccattgactc ccagcatcga
  1561  gtgcatgaag atattgaaat gaccaagact caatccattt atgatgacat gaagaaccac
  1621  agggaaagca actctaatca atgtgtctat gctgcacaca actctgtcat agtagatgaa
  1681  tgcaaggtaa ctctggcagc caatggaaag tcagccgact gcagtgttga ggaagaacct
  1741  tggaaacgtg agaaataagg atatgagtct cagcaaattc ttgaataaac tccccagcgt ▼ - splice junction

FIG. 8

SEQ ID NO:
11  1 gatagtgctg aagaggaggg gcgttcccag accatggcat ctacggaagg tgccaacaat
   61 atgcccaagc aggtggaagt gcgaatgcca gacagtcatc ttggctcaga ggaacccaag
  121 caccggcacc tgggcctgcg cctgtgtgac aagctgggga agaatctgct gctcaccctg
  181 acggtgtttg gtgtcatcct gggagcagtg tgtggagggc ttcttcgctt ggcatctccc
  241 atccaccctg atgtggttat gttaatagcc ttcccagggg atatactcat gaggatgcta
  301 aaaatgctca ttctccctct aatcatctcc agcttaatca cagggttgtc aggcctggat
  361 gctaaggcta gtggccgctt gggcacgaga gccatggtgt attacatgtc cacgaccatc
  421 attgctgcag tactgggggt cattctggtc ttggctatcc at ▼
        cc aagcttggat cactgccctg ggcaccgctt ccagtgctgg aactttgcct
        gtcacctttc gttgcctgga agaaaatctg gggattgata agcgtgtgac tagattcgtc
        cttcctgttg gagcaaccat taacatggat ggtacagccc tttatgaagc ggtggccgcc
        atctttatag cccaaatgaa tggtgttgtc ctggatggag gacagattgt gactgtaagc
        ctcacagcca ccctggcaag cgtcggcgcg gccagtatcc ccagtgccgg gctggtcacc
        atgctcctca ttctgacagc cgtgggcctg ccaacagagg acatcagctt gctggtggct
        gtggactggc tgctggacag gatgagaact tcagtcaatg ttgtgggtga ctcttttggg
        gctgggatag tctatcacct ctccaagtct gagctggata ccattgactc ccagcatcga
        gtgcatgaag atattgaaat gaccaagact caatccattt atgatgacat gaagaaccac
        agggaaagca actctaatca atgtgtctat gctgcacaca actctgtcat agtagatgaa
        tgcaaggtaa ctctggcagc caatggaaag tcagccgact gcagtgttga ggaagaacct
        tggaaacgtg agaaataagg atatgagtct cagcaaattc ttgaataaac tccccagcgt ▼ - splice junction

FIG. 9

SEQ ID NO:
12  1 gatagtgctg aagaggaggg gcgttcccag accatggcat ctacggaagg ▼
        ggacag gatgagaact tcagtcaatg ttgtgggtga ctcttttggg
        gctgggatag tctatcacct ctccaagtct gagctggata ccattgactc ccagcatcga
        gtgcatgaag atattgaaat gaccaagact caatccattt atgatgacat gaagaaccac
        agggaaagca actctaatca atgtgtctat gctgcacaca actctgtcat agtagatgaa
        tgcaaggtaa ctctggcagc caatggaaag tcagccgact gcagtgttga ggaagaacct
        tggaaacgtg agaaataagg atatgagtct cagcaaattc ttgaataaac tccccagcgt ▼ - splice junction

FIG. 10

SEQ ID NO:

13 1  gatagtgctg aagaggaggg gcgttcccag accatggcat ctacggaagg▼
cctcacagcca ccctggcaag cgtcggcgcg gccagtatcc ccagtgccgg gctggtcacc
atgctcctca ttctgacagc cgtgggcctg ccaacagagg acatcagctt gctggtggct
gtggactggc tgctggacag gatgagaact tcagtcaatg ttgtgggtga ctcttttggg
gctgggatag tctatcacct ctccaagtct gagctggata ccattgactc ccagcatcga
gtgcatgaag atattgaaat gaccaagact caatccattt atgatgacat gaagaaccac
agggaaagca actctaatca atgtgtctat gctgcacaca actctgtcat agtagatgaa
tgcaaggtaa ctctggcagc caatggaaag tcagccgact gcagtgttga ggaagaacct
tggaaacgtg agaaataagg atatgagtct cagcaaattc ttgaataaac tccccagcgt ▼ - splice junction

FIG. 11

| Exon | Position[a] | Size (bp) | Acceptor sequence | Seq. ID No. | Donor sequence | Seq. ID No. |
|---|---|---|---|---|---|---|
| I | -89-17 | 106 | | | GAAGGgtgagggatt | 34 |
| II | 18-157 | 140 | tctgttcccagTGCCA | 24 | GTTTGgtaggtacct | 35 |
| III | 158-310 | 152 | ttcctttttagGTGTC | 25 | CACAGgtaagactac | 36 |
| IV | 311-561 | 250 | ttcaatccagGGTTG | 26 | AACAGgtaacccaga | 37 |
| V | 562-730 | 169 | actctgttagATTCA | 27 | CTTAGgtaggccagc | 38 |
| VI | 731-858 | 128 | cacccaacagGTCTG | 28 | ATGTGgtaagtgcc | 39 |
| VII | 859-1091 | 233 | tgttttcagGTACT | 29 | TCCAGgtagagaaca | 40 |
| VIII | 1092-1286 | 195 | ttgttctcagTGCTG | 30 | GTAAGgtgagaaggg | 41 |
| IX | 1287-1421 | 135 | gttctcatagCCTCA | 31 | CTGCTgtaagtgtct | 42 |
| X | 1422-1653 | 232 | tgtaccccagGGACA | 32 | GCAAGgtacattcc | 43 |
| XI | 1654-1809 | 156 | ttatttcagGTAAC | 33 | | |

FIG. 12

| SEQUENCE ID NO: | | | |
|---|---|---|---|
| 44 | ↓-246 AAGCGCCATCCCCGCGGGCG------ | ↓52 GGCCGCCATCTTTATAGCCC | |
| 45 | ↓-259 GGAGCTCCCCGCCAAGCGCG------ | ↓53 GGCCGCCATCTTTATAGCCC | |
| 46 | ↓53 GAAGTGCGAATGCCAGACAG------ | ↓54 GTATTACATGTCCACGACCA | |
| 47 | ↓412 GGGGGTCATTCTGGTCTTGG------ | ↓55 CAGTGCCGGGCTGGTCACCA | |
| 48 | ↓-365 CAAAGCACAGCGCCCCGAGC------ | ↓56 CAAGCTGATGGTGGATTCT | |
| 49 | ↓434 ATCTATCCATCCAGGCAATC------ | ↓57 CTGGCATTTTCCAAGCTTGG | |
| 50 | EXON 2 ↓17 EXON 3 CTACGGAAGGTGCCAACAAT------ | ↓1422 EXON 10 58 ACTGGCTGCTGGACAGGATG | |
| 51 | EXON 2 ↓17 EXON 3 CTACGGAAGGTGCCAACAAT------ | ↓1287 EXON 9 59 TGACTGTAAGCCTCACAGCC | |

FIG. 13B

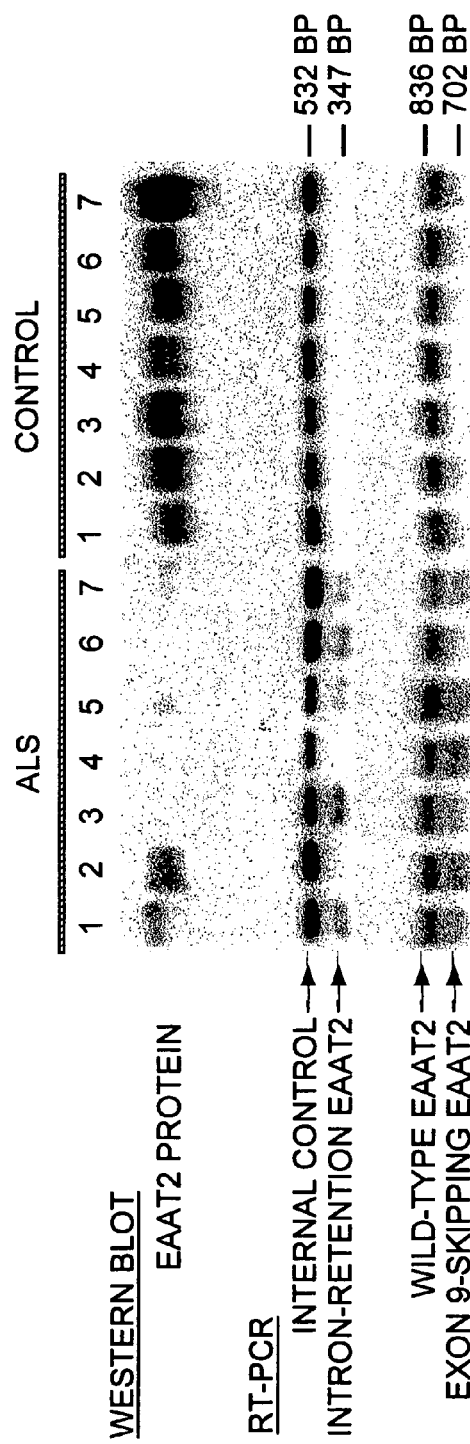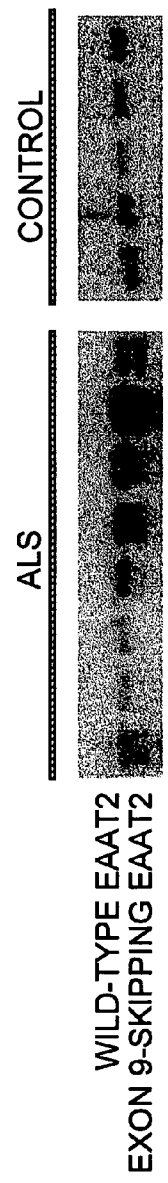
FIG. 14A
FIG. 14B

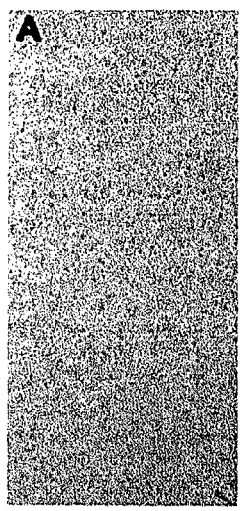 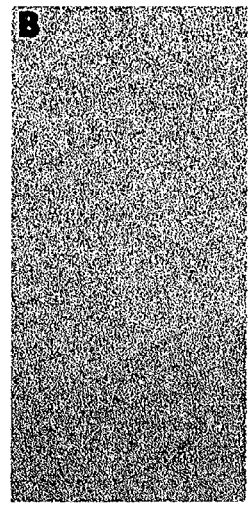 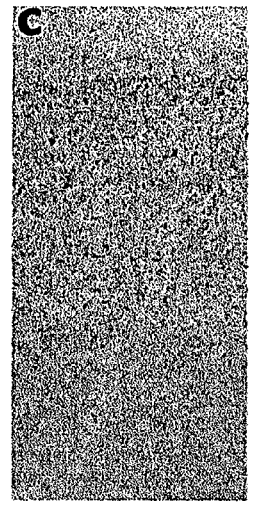
FIG. 15A  FIG. 15B  FIG. 15C

FIG. 15F
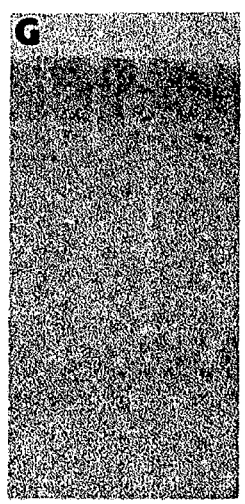 
FIG. 15G  FIG. 15H

SEQ ID NO: 60

-380
AGCCCCGCAGCAAAGCACAGTGGCAGGGCTGCAGGGGCATCGCCGGGTGCGC
CCTCCTGCAGCCCTGGGCGCTCTCTCGGGGAAGCCACCCTCGGAGCCCCGG
AGCTCCCCGCCAAGCGCCATCCCCGCGGGCGAGGGGAGCGCGGTCGCGCCGTG
GAGAGCCGGGACGCGGGATTAGCGCCCGCAGGAGCCTCCTGCGCCCGTTGAGGCGCTA
AAGGGCTTACCCCCGGAGGCGGGGGTGGAAGGGGCAGAGGCTCCTCTTAAATACCG
CTCCCCGGCCGCACTTCGCGCTCACCCCGGGTCCGCGTTTCTCCCTCGCCCACAGCTGC
CGGATAGTGCTGAAGAGAGGAAGGGGGCGTTCCCCAGACC |+1 ATG → CODING REGION

FIG. 20

SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
      (A) LENGTH: 1800 base pairs
      (B) TYPE: nucleic acid
      (C) STRANDEDNESS: single -continued (D) TOPOLOGY: linear (ii) MOLECULE TYPE: cDNA (ix) FEATURE:
    (A) NAME/KEY: CDS
    (B) LOCATION: 34..1755

(xi) SEQUENCE DESCRIPTION: SEQ ID NO:1:

```
GATAGTGCTG AAGAGGAGGG GCGTTCCCAG ACC ATG GCA TCT ACG GAA GGT GCC         54
                                    Met Ala Ser Thr Glu Gly Ala
                                    1               5

AAC AAT ATG CCC AAG CAG GTG GAA GTG CGA ATG CCA GAC AGT CAT CTT         102
Asn Asn Met Pro Lys Gln Val Glu Val Arg Met Pro Asp Ser His Leu
        10                  15                  20

GGC TCA GAG GAA CCC AAG CAC CGG CAC CTG GGC CTG CGC CTG TGT GAC         150
Gly Ser Glu Glu Pro Lys His Arg His Leu Gly Leu Arg Leu Cys Asp
    25                  30                  35

AAG CTG GGG AAG AAT CTG CTG CTC ACC CTG ACG GTG TTT GGT GTC ATC         198
Lys Leu Gly Lys Asn Leu Leu Leu Thr Leu Thr Val Phe Gly Val Ile
40                  45                  50                  55

CTG GGA GCA GTG TGT GGA GGG CTT CTT CGC TTG GCA TCT CCC ATC CAC         246
Leu Gly Ala Val Cys Gly Gly Leu Leu Arg Leu Ala Ser Pro Ile His
                60                  65                  70

CCT GAT GTG GTT ATG TTA ATA GCC TTC CCA GGG GAT ATA CTC ATG AGG         294
Pro Asp Val Val Met Leu Ile Ala Phe Pro Gly Asp Ile Leu Met Arg
            75                  80                  85

ATG CTA AAA ATG CTC ATT CTC CCT CTA ATC ATC TCC AGC TTA ATC ACA         342
Met Leu Lys Met Leu Ile Leu Pro Leu Ile Ile Ser Ser Leu Ile Thr
        90                  95                  100

GGG TTG TCA GGC CTG GAT GCT AAG GCT AGT GGC CGC TTG GGC ACG AGA         390
Gly Leu Ser Gly Leu Asp Ala Lys Ala Ser Gly Arg Leu Gly Thr Arg
    105                 110                 115

GCC ATG GTG TAT TAC ATG TCC ACG ACC ATC ATT GCT GCA GTA CTG GGG         438
Ala Met Val Tyr Tyr Met Ser Thr Thr Ile Ile Ala Ala Val Leu Gly
120                 125                 130                 135

GTC ATT CTG GTC TTG GCT ATC CAT CCA GGC AAT CCC AAG CTC AAG AAG         486
Val Ile Leu Val Leu Ala Ile His Pro Gly Asn Pro Lys Leu Lys Lys
                140                 145                 150

CAG CTG GGG CCT GGG AAG AAG AAT GAT GAA GTG TCC AGC CTG GAT GCC         534
Gln Leu Gly Pro Gly Lys Lys Asn Asp Glu Val Ser Ser Leu Asp Ala
            155                 160                 165

TTC CTG GAC CTT ATT CGA AAT CTC TTC CCT GAA AAC TTG GTC CAA GCC         582
Phe Leu Asp Leu Ile Arg Asn Leu Phe Pro Glu Asn Leu Val Gln Ala
        170                 175                 180

TGC TTT CAA CAG ATT CAA ACA GTG ACG AAG AAA GTC CTG GTT GCA CCA         630
Cys Phe Gln Gln Ile Gln Thr Val Thr Lys Lys Val Leu Val Ala Pro
    185                 190                 195

CCG CCA GAC GAG GAG GCC AAC GCA ACC AGC GCT GAA GTC TCT CTG TTG         678
Pro Pro Asp Glu Glu Ala Asn Ala Thr Ser Ala Glu Val Ser Leu Leu
200                 205                 210                 215

AAC GAG ACT GTG ACT GAG GTG CCG GAG GAG ACT AAG ATG GTT ATC AAG         726
Asn Glu Thr Val Thr Glu Val Pro Glu Glu Thr Lys Met Val Ile Lys
                220                 225                 230

AAG GGC CTG GAG TTC AAG GAT GGG ATG AAC GTC TTA GGT CTG ATA GGG         774
Lys Gly Leu Glu Phe Lys Asp Gly Met Asn Val Leu Gly Leu Ile Gly
            235                 240                 245

TTT TTC ATT GCT TTT GGC ATC GCT ATG GGG AAG ATG GGA GAT CAG GCC         822
Phe Phe Ile Ala Phe Gly Ile Ala Met Gly Lys Met Gly Asp Gln Ala
        250                 255                 260

AAG CTG ATG GTG GAT TTC TTC AAC ATT TTG AAT GAG ATT GTA ATG AAG         870
```

```
                                                                -continued

Lys Leu Met Val Asp Phe Phe Asn Ile Leu Asn Glu Ile Val Met Lys
265                 270                 275

TTA GTG ATC ATG ATC ATG TGG TAC TCT CCC CTG GGT ATC GCC TGC CTG       918
Leu Val Ile Met Ile Met Trp Tyr Ser Pro Leu Gly Ile Ala Cys Leu
280                 285                 290                 295

ATC TGT GGA AAG ATC ATT GCA ATC AAG GAC TTA GAA GTG GTT GCT AGG       966
Ile Cys Gly Lys Ile Ile Ala Ile Lys Asp Leu Glu Val Val Ala Arg
                300                 305                 310

CAA CTG GGG ATG TAC ATG GTA ACA GTG ATC ATA GGC CTC ATC ATC CAC      1014
Gln Leu Gly Met Tyr Met Val Thr Val Ile Ile Gly Leu Ile Ile His
                315                 320                 325

GGG GGC ATC TTT CTC CCC TTG ATT TAC TTT GTA GTG ACC AGG AAA AAC      1062
Gly Gly Ile Phe Leu Pro Leu Ile Tyr Phe Val Val Thr Arg Lys Asn
                330                 335                 340

CCC TTC TCC CTT TTT GCT GGC ATT TTC CAA GCT TGG ATC ACT GCC CTG      1110
Pro Phe Ser Leu Phe Ala Gly Ile Phe Gln Ala Trp Ile Thr Ala Leu
345                 350                 355

GGC ACC GCT TCC AGT GCT GGA ACT TTG CCT GTC ACC TTT CGT TGC CTG      1158
Gly Thr Ala Ser Ser Ala Gly Thr Leu Pro Val Thr Phe Arg Cys Leu
360                 365                 370                 375

GAA GAA AAT CTG GGG ATT GAT AAG CGT GTG ACT AGA TTC GTC CTT CCT      1206
Glu Glu Asn Leu Gly Ile Asp Lys Arg Val Thr Arg Phe Val Leu Pro
                380                 385                 390

GTT GGA GCA ACC ATT AAC ATG GAT GGT ACA GCC CTT TAT GAA GCG GTG      1254
Val Gly Ala Thr Ile Asn Met Asp Gly Thr Ala Leu Tyr Glu Ala Val
                395                 400                 405

GCC GCC ATC TTT ATA GCC CAA ATG AAT GGT GTT GTC CTG GAT GGA GGA      1302
Ala Ala Ile Phe Ile Ala Gln Met Asn Gly Val Val Leu Asp Gly Gly
                410                 415                 420

CAG ATT GTG ACT GTA AGC CTC ACA GCC ACC CTG GCA AGC GTC GGC GCG      1350
Gln Ile Val Thr Val Ser Leu Thr Ala Thr Leu Ala Ser Val Gly Ala
425                 430                 435

GCC AGT ATC CCC AGT GCC GGG CTG GTC ACC ATG CTC CTC ATT CTG ACA      1398
Ala Ser Ile Pro Ser Ala Gly Leu Val Thr Met Leu Leu Ile Leu Thr
440                 445                 450                 455

GCC GTG GGC CTG CCA ACA GAG GAC ATC AGC TTG CTG GTG GCT GTG GAC      1446
Ala Val Gly Leu Pro Thr Glu Asp Ile Ser Leu Leu Val Ala Val Asp
                460                 465                 470

TGG CTG CTG GAC AGG ATG AGA ACT TCA GTC AAT GTT GTG GGT GAC TCT      1494
Trp Leu Leu Asp Arg Met Arg Thr Ser Val Asn Val Val Gly Asp Ser
                475                 480                 485

TTT GGG GCT GGG ATA GTC TAT CAC CTC TCC AAG TCT GAG CTG GAT ACC      1542
Phe Gly Ala Gly Ile Val Tyr His Leu Ser Lys Ser Glu Leu Asp Thr
                490                 495                 500

ATT GAC TCC CAG CAT CGA GTG CAT GAA GAT ATT GAA ATG ACC AAG ACT      1590
Ile Asp Ser Gln His Arg Val His Glu Asp Ile Glu Met Thr Lys Thr
505                 510                 515

CAA TCC ATT TAT GAT GAC ATG AAG AAC CAC AGG GAA AGC AAC TCT AAT      1638
Gln Ser Ile Tyr Asp Asp Met Lys Asn His Arg Glu Ser Asn Ser Asn
520                 525                 530                 535

CAA TGT GTC TAT GCT GCA CAC AAC TCT GTC ATA GTA GAT GAA TGC AAG      1686
Gln Cys Val Tyr Ala Ala His Asn Ser Val Ile Val Asp Glu Cys Lys
                540                 545                 550

GTA ACT CTG GCA GCC AAT GGA AAG TCA GCC GAC TGC AGT GTT GAG GAA      1734
Val Thr Leu Ala Ala Asn Gly Lys Ser Ala Asp Cys Ser Val Glu Glu
                555                 560                 565

GAA CCT TGG AAA CGT GAG AAA TAAGGATATG AGTCTCAGCA AATTCTTGAA         1785
Glu Pro Trp Lys Arg Glu Lys
                570
```

TAAACTCCCC AGCGT                                                    1800

(2) INFORMATION FOR SEQ ID NO:2:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ser Thr Glu Gly Ala Asn Asn Met Pro Lys Gln Val Glu Val
  1               5                  10                  15

Arg Met Pro Asp Ser His Leu Gly Ser Glu Glu Pro Lys His Arg His
                 20                  25                  30

Leu Gly Leu Arg Leu Cys Asp Lys Leu Gly Lys Asn Leu Leu Leu Thr
             35                  40                  45

Leu Thr Val Phe Gly Val Ile Leu Gly Ala Val Cys Gly Gly Leu Leu
 50                  55                  60

Arg Leu Ala Ser Pro Ile His Pro Asp Val Val Met Leu Ile Ala Phe
 65                  70                  75                  80

Pro Gly Asp Ile Leu Met Arg Met Leu Lys Met Leu Ile Leu Pro Leu
                 85                  90                  95

Ile Ile Ser Ser Leu Ile Thr Gly Leu Ser Gly Leu Asp Ala Lys Ala
                100                 105                 110

Ser Gly Arg Leu Gly Thr Arg Ala Met Val Tyr Tyr Met Ser Thr Thr
            115                 120                 125

Ile Ile Ala Ala Val Leu Gly Val Ile Leu Val Leu Ala Ile His Pro
130                 135                 140

Gly Asn Pro Lys Leu Lys Lys Gln Leu Gly Pro Gly Lys Lys Asn Asp
145                 150                 155                 160

Glu Val Ser Ser Leu Asp Ala Phe Leu Asp Leu Ile Arg Asn Leu Phe
                165                 170                 175

Pro Glu Asn Leu Val Gln Ala Cys Phe Gln Gln Ile Gln Thr Val Thr
                180                 185                 190

Lys Lys Val Leu Val Ala Pro Pro Asp Glu Glu Ala Asn Ala Thr
            195                 200                 205

Ser Ala Glu Val Ser Leu Leu Asn Glu Thr Val Thr Glu Val Pro Glu
210                 215                 220

Glu Thr Lys Met Val Ile Lys Lys Gly Leu Glu Phe Lys Asp Gly Met
225                 230                 235                 240

Asn Val Leu Gly Leu Ile Gly Phe Phe Ile Ala Phe Gly Ile Ala Met
                245                 250                 255

Gly Lys Met Gly Asp Gln Ala Lys Leu Met Val Asp Phe Phe Asn Ile
            260                 265                 270

Leu Asn Glu Ile Val Met Lys Leu Val Ile Met Ile Met Trp Tyr Ser
            275                 280                 285

Pro Leu Gly Ile Ala Cys Leu Ile Cys Gly Lys Ile Ile Ala Ile Lys
290                 295                 300

Asp Leu Glu Val Val Ala Arg Gln Leu Gly Met Tyr Met Val Thr Val
305                 310                 315                 320

Ile Ile Gly Leu Ile Ile His Gly Gly Ile Phe Leu Pro Leu Ile Tyr
                325                 330                 335

Phe Val Val Thr Arg Lys Asn Pro Phe Ser Leu Phe Ala Gly Ile Phe
                340                 345                 350
```

```
Gln Ala Trp Ile Thr Ala Leu Gly Thr Ala Ser Ser Ala Gly Thr Leu
            355                 360                 365

Pro Val Thr Phe Arg Cys Leu Glu Glu Asn Leu Gly Ile Asp Lys Arg
    370                 375                 380

Val Thr Arg Phe Val Leu Pro Val Gly Ala Thr Ile Asn Met Asp Gly
385                 390                 395                 400

Thr Ala Leu Tyr Glu Ala Val Ala Ala Ile Phe Ile Ala Gln Met Asn
                405                 410                 415

Gly Val Val Leu Asp Gly Gly Gln Ile Val Thr Val Ser Leu Thr Ala
            420                 425                 430

Thr Leu Ala Ser Val Gly Ala Ala Ser Ile Pro Ser Ala Gly Leu Val
            435                 440                 445

Thr Met Leu Leu Ile Leu Thr Ala Val Gly Leu Pro Thr Glu Asp Ile
    450                 455                 460

Ser Leu Leu Val Ala Val Asp Trp Leu Leu Asp Arg Met Arg Thr Ser
465                 470                 475                 480

Val Asn Val Val Gly Asp Ser Phe Gly Ala Gly Ile Val Tyr His Leu
            485                 490                 495

Ser Lys Ser Glu Leu Asp Thr Ile Asp Ser Gln His Arg Val His Glu
            500                 505                 510

Asp Ile Glu Met Thr Lys Thr Gln Ser Ile Tyr Asp Asp Met Lys Asn
            515                 520                 525

His Arg Glu Ser Asn Ser Asn Gln Cys Val Tyr Ala Ala His Asn Ser
        530                 535                 540

Val Ile Val Asp Glu Cys Lys Val Thr Leu Ala Ala Asn Gly Lys Ser
545                 550                 555                 560

Ala Asp Cys Ser Val Glu Glu Glu Pro Trp Lys Arg Glu Lys
                565                 570

(2) INFORMATION FOR SEQ ID NO:3:

(i) SEQUENCE CHARACTERISTICS:
        (A) LENGTH: 1182 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..161

(xi) SEQUENCE DESCRIPTION: SEQ ID NO:3:

GG CAA CTG GGG ATG TAC ATG GTA ACA GTG ATC ATA GGC CTC ATC ATC       47
   Gln Leu Gly Met Tyr Met Val Thr Val Ile Ile Gly Leu Ile Ile
   1               5                  10                  15

CAC GGG GGC ATC TTT CTC CCC TTG ATT TAC TTT GTA GTG ACC AGG AAA      95
His Gly Gly Ile Phe Leu Pro Leu Ile Tyr Phe Val Val Thr Arg Lys
                20                  25                  30

AAC CCC TTC TCC TGT TGT GGT GGC ATT TTC CAA GCT TGG ATC ACT GCC     143
Asn Pro Phe Ser Cys Cys Gly Gly Ile Phe Gln Ala Trp Ile Thr Ala
            35                  40                  45

CTG GGC ACC GCT TCC AGG TAGAGAACAA AAGAAATCAC CTTTCTCTTT            191
Leu Gly Thr Ala Ser Arg
        50

GCTCACTCTT GGCCCTCTTT GCCATTTCTC ATTCTCAACC CCCTCCCATC ACAAAGTTCA   251

ATAAGAACAC TTGGCACACA TTACTTGATC TTTTGGAAAA GGCGAATGAT TTGAATTTTT   311
```

```
GTCTCCTTCT AGGAACTTCT GAGCCTTCTG GTGAACATTT TTGCTGGTTT GCAACTATAT    371

TGGAAATACG ATCTCACATT AAATTTTTCA GATAAATGCA TGCTATTTGT TTGCATGCCT    431

AATTTGCCAC TTAAATCATT AGTTTAGTTT TAGATGTTTT CTAAAGGGAG TGTAACAGGA    491

TATTTTTCAA TAAACATTTC ACCTGTGATT TGGAAAATGC TATCACAAAA TATTACTCTT    551

TGAAGATTTT GGTAAATACA TTTTCAAAAG TAGGAGAAGC AGCTTTTACA AAGTAAATGG    611

TATGTTAGGT GAGACTTTTT CTAACAAAAT TCGGCCAAGT CTTTGACCTC GACACGAACC    671

TCTAATGGAT TATTTTTCCC CAGAGTTAAC TTGTCATTGA TGAAGAATCA GTTCCCCCTT    731

TGTTACTTAG TTCCAGTACC TAGAAAGCCA AAGAGGACCC CAGAGATATG TAGAGAAAAA    791

TCATTTTTTG GACTATCATC TTGGACTGAA TCTAACAAAA ACAAACCAAC AAATGAACAA    851

GAAGAAATAC ATAAGAAACG TCTTACAATT AGGCTGGGCG CAGTAGCTCA TGCTTGTAAT    911

CCCAGCACTT TGGGAGGCCT CGGCAGGCGG ATCACTTGAA GTCAGGAGTT CGAGGCCAGC    971

CTGGCTAACA TGGTGAAACC CCGTCTCTCC TAAAAAAACA AAAATTAACC AGGTGCGGTG   1031

GGGGGCGCCT ATAATCCCAG CTATTCGGTA GTCTGTGTCA GGAGAATTGC TTGAACCTAG   1091

GAGGCAGAGG TTGCAGTGAG CTGAGATTGC ATCACTGCAC TCTAGTCTGG GTGGCAAAGT   1151

GAGGCTCCAT CTGTAAAAAA AAAAAAAAA A                                  1182

(2) INFORMATION FOR SEQ ID NO:4:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO:4:

Gln Leu Gly Met Tyr Met Val Thr Val Ile Ile Gly Leu Ile Ile His
  1               5                  10                  15

Gly Gly Ile Phe Leu Pro Leu Ile Tyr Phe Val Val Thr Arg Lys Asn
             20                  25                  30

Pro Phe Ser Cys Cys Gly Gly Ile Phe Gln Ala Trp Ile Thr Ala Leu
         35                  40                  45

Gly Thr Ala Ser Arg
         50

(2) INFORMATION FOR SEQ ID NO:5:

(i) SEQUENCE CHARACTERISTICS:
        (A) LENGTH: 1665 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GATAGTGCTG AAGAGGAGGG GCGTTCCCAG ACCATGGCAT CTACGGAAGG TGCCAACAAT     60

ATGCCCAAGC AGGTGGAAGT GCGAATGCCA GACAGTCATC TTGGCTCAGA GGAACCCAAG    120

CACCGGCACC TGGGCCTGCG CCTGTGTGAC AAGCTGGGGA AGAATCTGCT GCTCACCCTG    180

ACGGTGTTTG GTGTCATCCT GGGAGCAGTG TGTGGAGGGC TTCTTCGCTT GGCATCTCCC    240

ATCCACCCTG ATGTGGTTAT GTTAATAGCC TTCCCAGGGG ATACTCAT GAGGATGCTA     300

AAAATGCTCA TTCTCCCTCT AATCATCTCC AGCTTAATCA CAGGGTTGTC AGGCCTGGAT    360
```

```
GCTAAGGCTA GTGGCCGCTT GGGCACGAGA GCCATGGTGT ATTACATGTC CACGACCATC      420

ATTGCTGCAG TACTGGGGGT CATTCTGGTC TTGGCTATCC ATCCAGGCAA TCCCAAGCTC      480

AAGAAGCAGC TGGGGCCTGG GAAGAAGAAT GATGAAGTGT CCAGCCTGGA TGCCTTCCTG      540

GACCTTATTC GAAATCTCTT CCCTGAAAAC CTTGTCCAAG CCTGCTTTCA ACAGATTCAA      600

ACAGTGACGA AGAAAGTCCT GGTTGCACCA CCGCCAGACG AGGAGGCCAA CGCAACCAGC      660

GCTGAAGTCT CTCTGTTGAA CGAGACTGTG ACTGAGGTGC CGGAGGAGAC TAAGATGGTT      720

ATCAAGAAGG GCCTGGAGTT CAAGGATGGG ATGAACGTCT TAGGTCTGAT AGGGTTTTTC      780

ATTGCTTTTG GCATCGCTAT GGGGAAGATG GGAGATCAGG CCAAGCTGAT GGTGGATTTC      840

TTCAACATTT TGAATGAGAT TGTAATGAAG TTAGTGATCA TGATCATGTG GTACTCTCCC      900

CTGGGTATCG CCTGCCTGAT CTGTGGAAAG ATCATTGCAA TCAAGGACTT AGAAGTGGTT      960

GCTAGGCAAC TGGGGATGTA CATGGTAACA GTGATCATAG GCCTCATCAT CCACGGGGGC     1020

ATCTTTCTCC CCTTGATTTA CTTTGTAGTG ACCAGGAAAA ACCCCTTCTC CCTTTTTGCT     1080

GGCATTTTCC AAGCTTGGAT CACTGCCCTG GGCACCGCTT CCAGTGCTGG AACTTTGCCT     1140

GTCACCTTTC GTTGCCTGGA AGAAAATCTG GGGATTGATA AGCGTGTGAC TAGATTCGTC     1200

CTTCCTGTTG GAGCAACCAT TAACATGGAT GGTACAGCCC TTTATGAAGC GGTGGCCGCC     1260

ATCTTTATAG CCCAAATGAA TGGTGTTGTC CTGGATGGAG GACAGATTGT GACTGTAAGG     1320

GACAGGATGA GAACTTCAGT CAATGTTGTG GGTGACTCTT TTGGGGCTGG GATAGTCTAT     1380

CACCTCTCCA AGTCTGAGCT GGATACCATT GACTCCCAGC ATCGAGTGCA TGAAGATATT     1440

GAAATGACCA AGACTCAATC CATTTATGAT GACATGAAGA ACCACAGGGA AAGCAACTCT     1500

AATCAATGTG TCTATGCTGC ACACAACTCT GTCATAGTAG ATGAATGCAA GGTAACTCTG     1560

GCAGCCAATG AAAGTCAGC CGACTGCAGT GTTGAGGAAG AACCTTGGAA ACGTGAGAAA     1620

TAAGGATATG AGTCTCAGCA AATTCTTGAA TAAACTCCCC AGCGT                     1665

(2) INFORMATION FOR SEQ ID NO:6:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGCCCCGCAG CAAAGCACAG GTGGCAGCGG CTGCAGGGGC GCATCGCCGG CGTGCGCCCT       60

CCTGCAGCCC TGGGCGCATC GCTCTCTCGG GGAAGCCACC CTCGGAGCCC CCGGAGCTCC      120

CCGCCAAGCG CCATCTTTAT AGCCCAAATG AATGGTGTTG TCCTGGATGG AGGACAGATT      180

GTGACTGTAA GCCTCACAGC CACCCTGGCA AGCGTCGGCG CGGCCAGTAT CCCCAGTGCC      240

GGGCTGGTCA CCATGCTCCT CATTCTGACA GCCGTGGGCC TGCCAACAGA GGACATCAGC      300

TTGCTGGTGG CTGTGGACTG GCTGCTGGAC AGGATGAGAA CTTCAGTCAA TGTTGTGGGT      360

GACTCTTTTG GGGCTGGGAT AGTCTATCAC CTCTCCAAGT CTGAGCTGGA TACCATTGAC      420

TCCCAGCATC GAGTGCATGA AGATATTGAA ATGACCAAGA CTCAATCCAT TTATGATGAC      480

ATGAAGAACC ACAGGGAAAG CAACTCTAAT CAATGTGTCT ATGCTGCACA CAACTCTGTC      540

ATAGTAGATG AATGCAAGGT AACTCTGGCA GCCAATGGAA AGTCAGCCGA CTGCAGTGTT      600

GAGGAAGAAC CTTGGAAACG TGAGAAATAA GGATATGAGT CTCAGCAAAT TCTTGAATAA      660
```

ACTCCCCAGC GT                                                             672

(2) INFORMATION FOR SEQ ID NO:7:

(i) SEQUENCE CHARACTERISTICS:
        (A) LENGTH: 659 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

AGCCCCGCAG CAAAGCACAG GTGGCAGCGG CTGCAGGGGC GCATCGCCGG CGTGCGCCCT          60

CCTGCAGCCC TGGGCGCATC GCTCTCTCGG GGAAGCCACC CTCGGAGCCC CCGGAGCTCC         120

CCTTTATAGC CCAAATGAAT GGTGTTGTCC TGGATGGAGG ACAGATTGTG ACTGTAAGCC         180

TCACAGCCAC CCTGGCAAGC GTCGGCGCGG CCAGTATCCC CAGTGCCGGG CTGGTCACCA         240

TGCTCCTCAT TCTGACAGCC GTGGGCCTGC AACAGAGGA CATCAGCTTG CTGGTGGCTG          300

TGGACTGGCT GCTGGACAGG ATGAGAACTT CAGTCAATGT TGTGGGTGAC TCTTTTGGGG         360

CTGGGATAGT CTATCACCTC TCCAAGTCTG AGCTGGATAC CATTGACTCC CAGCATCGAG         420

TGCATGAAGA TATTGAAATG ACCAAGACTC AATCCATTTA TGATGACATG AAGAACCACA         480

GGGAAAGCAA CTCTAATCAA TGTGTCTATG CTGCACACAA CTCTGTCATA GTAGATGAAT         540

GCAAGGTAAC TCTGGCAGCC AATGGAAAGT CAGCCGACTG CAGTGTTGAG GAAGAACCTT         600

GGAAACGTGA GAAATAAGGA TATGAGTCTC AGCAAATTCT TGAATAAACT CCCCAGCGT         659

(2) INFORMATION FOR SEQ ID NO:8:

(i) SEQUENCE CHARACTERISTICS:
        (A) LENGTH: 1477 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GATAGTGCTG AAGAGGAGGG GCGTTCCCAG ACCATGGCAT CTACGGAAGG TGCCAACAAT          60

ATGCCCAAGC AGGTGGAAGT GCGAATCCAC GACCATCATT GCTGCAGTAC TGGGGGTCAT         120

TCTGGTCTTG GCTATCCATC CAGGCAATCC CAAGCTCAAG AAGCAGCTGG GGCCTGGGAA         180

GAAGAATGAT GAAGTGTCCA GCCTGGATGC CTTCCTGGAC CTTATTCGAA ATCTCTTCCC         240

TGAAAACCTT GTCCAAGCCT GCTTTCAACA GATTCAAACA GTGACGAAGA AGTCCTGGT          300

TGCACCACCG CCAGACGAGG AGGCCAACGC AACCAGCGCT GAAGTCTCTC TGTTGAACGA         360

GACTGTGACT GAGGTGCCGG AGGAGACTAA GATGGTTATC AAGAAGGGCC TGGAGTTCAA         420

GGATGGGATG AACGTCTTAG GTCTGATAGG GTTTTTCATT GCTTTTGGCA TCGCTATGGG         480

GAAGATGGGA GATCAGGCCA AGCTGATGGT GGATTTCTTC AACATTTTGA ATGAGATTGT         540

AATGAAGTTA GTGATCATGA TCATGTGGTA CTCTCCCCTG GGTATCGCCT GCCTGATCTG         600

TGGAAAGATC ATTGCAATCA AGGACTTAGA AGTGGTTGCT AGGCAACTGG GGATGTACAT         660

GGTAACAGTG ATCATAGGCC TCATCATCCA CGGGGCATC TTTCTCCCCT TGATTTACTT         720

TGTAGTGACC AGGAAAAACC CCTTCTCCCT TTTTGCTGGC ATTTTCCAAG CTTGGATCAC         780

TGCCCTGGGC ACCGCTTCCA GTGCTGGAAC TTTGCCTGTC ACCTTCGTT GCCTGGAAGA         840

| AAATCTGGGG ATTGATAAGC GTGTGACTAG ATTCGTCCTT CCTGTTGGAG CAACCATTAA | 900 |
| CATGGATGGT ACAGCCCTTT ATGAAGCGGT GGCCGCCATC TTTATAGCCC AAATGAATGG | 960 |
| TGTTGTCCTG GATGGAGGAC AGATTGTGAC TGTAAGCCTC ACAGCCACCC TGGCAAGCGT | 1020 |
| CGGCGCGGCC AGTATCCCCA GTGCCGGGCT GGTCACCATG CTCCTCATTC TGACAGCCGT | 1080 |
| GGGCCTGCCA ACAGAGGACA TCAGCTTGCT GGTGGCTGTG GACTGGCTGC TGGACAGGAT | 1140 |
| GAGAACTTCA GTCAATGTTG TGGGTGACTC TTTTGGGGCT GGGATAGTCT ATCACCTCTC | 1200 |
| CAAGTCTGAG CTGGATACCA TTGACTCCCA GCATCGAGTG CATGAAGATA TTGAAATGAC | 1260 |
| CAAGACTCAA TCCATTTATG ATGACATGAA GAACCACAGG GAAAGCAACT CTAATCAATG | 1320 |
| TGTCTATGCT GCACACAACT CTGTCATAGT AGATGAATGC AAGGTAACTC TGGCAGCCAA | 1380 |
| TGGAAAGTCA GCCGACTGCA GTGTTGAGGA AGAACCTTGG AAACGTGAGA ATAAGGATA | 1440 |
| TGAGTCTCAG CAAATTCTTG AATAAACTCC CCAGCGT | 1477 |

(2) INFORMATION FOR SEQ ID NO:9:

(i) SEQUENCE CHARACTERISTICS:
        (A) LENGTH: 873 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

| GATAGTGCTG AAGAGGAGGG GCGTTCCCAG ACCATGGCAT CTACGGAAGG TGCCAACAAT | 60 |
| ATGCCCAAGC AGGTGGAAGT GCGAATGCCA GACAGTCATC TTGGCTCAGA GGAACCCAAG | 120 |
| CACCGGCACC TGGGCCTGCG CCTGTGTGAC AAGCTGGGGA AGAATCTGCT GCTCACCCTG | 180 |
| ACGGTGTTTG TGTCATCCT GGGAGCAGTG TGTGGAGGGC TTCTTCGCTT GGCATCTCCC | 240 |
| ATCCACCCTG ATGTGGTTAT GTTAATAGCC TTCCCAGGGG ATATACTCAT GAGGATGCTA | 300 |
| AAAATGCTCA TTCTCCCTCT AATCATCTCC AGCTTAATCA CAGGGTTGTC AGGCCTGGAT | 360 |
| GCTAAGGCTA GTGGCCGCTT GGGCACGAGA GCCATGGTGT ATTACATGTC CACGACCATC | 420 |
| ATTGCTGCAG TACTGGGGGT CATTCTGGTC ACCATGCTCC TCATTCTGAC AGCCGTGGGC | 480 |
| CTGCCAACAG AGGACATCAG CTTGCTGGTG GCTGTGGACT GGCTGCTGGA CAGGATGAGA | 540 |
| ACTTCAGTCA ATGTTGTGGG TGACTCTTTT GGGGCTGGGA TAGTCTATCA CCTCTCCAAG | 600 |
| TCTGAGCTGG ATACCATTGA CTCCCAGCAT CGAGTGCATG AAGATATTGA AATGACCAAG | 660 |
| ACTCAATCCA TTTATGATGA CATGAAGAAC CACAGGGAAA GCAACTCTAA TCAATGTGTC | 720 |
| TATGCTGCAC ACAACTCTGT CATAGTAGAT GAATGCAAGG TAACTCTGGC AGCCAATGGA | 780 |
| AAGTCAGCCG ACTGCAGTGT TGAGGAAGAA CCTTGGAAAC GTGAGAAATA AGGATATGAG | 840 |
| TCTCAGCAAA TTCTTGAATA AACTCCCCAG CGT | 873 |

(2) INFORMATION FOR SEQ ID NO:10:

(i) SEQUENCE CHARACTERISTICS:
        (A) LENGTH: 989 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

| AGCCCCGCAG CAAAGCACAG GTGGATTTCT TCAACATTTT GAATGAGATT GTAATGAAGT | 60 |

| | |
|---|---|
| TAGTGATCAT GATCATGTGG TACTCTCCCC TGGGTATCGC CTGCCTGATC TGTGGAAAGA | 120 |
| TCATTGCAAT CAAGGACTTA GAAGTGGTTG CTAGGCAACT GGGGATGTAC ATGGTAACAG | 180 |
| TGATCATAGG CCTCATCATC CACGGGGGCA TCTTTCTCCC CTTGATTTAC TTTGTAGTGA | 240 |
| CCAGGAAAAA CCCCTTCTCC CTTTTTGCTG GCATTTTCCA AGCTTGGATC ACTGCCCTGG | 300 |
| GCACCGCTTC CAGTGCTGGA ACTTTGCCTG TCACCTTTCG TTGCCTGGAA GAAAATCTGG | 360 |
| GGATTGATAA GCGTGTGACT AGATTCGTCC TTCCTGTTGG AGCAACCATT AACATGGATG | 420 |
| GTACAGCCCT TTATGAAGCG GTGGCCGCCA TCTTTATAGC CCAAATGAAT GGTGTTGTCC | 480 |
| TGGATGGAGG ACAGATTGTG ACTGTAAGCC TCACAGCCAC CCTGGCAAGC GTCGGCGCGG | 540 |
| CCAGTATCCC CAGTGCCGGG CTGGTCACCA TGCTCCTCAT TCTGACAGCC GTGGGCCTGC | 600 |
| CAACAGAGGA CATCAGCTTG CTGGTGGCTG TGGACTGGCT GCTGGACAGG ATGAGAACTT | 660 |
| CAGTCAATGT TGTGGGTGAC TCTTTTGGGG CTGGGATAGT CTATCACCTC TCCAAGTCTG | 720 |
| AGCTGGATAC CATTGACTCC CAGCATCGAG TGCATGAAGA TATTGAAATG ACCAAGACTC | 780 |
| AATCCATTTA TGATGACATG AAGAACCACA GGGAAAGCAA CTCTAATCAA TGTGTCTATG | 840 |
| CTGCACACAA CTCTGTCATA GTAGATGAAT GCAAGGTAAC TCTGGCAGCC AATGGAAAGT | 900 |
| CAGCCGACTG CAGTGTTGAG GAAGAACCTT GGAAACGTGA GAAATAAGGA TATGAGTCTC | 960 |
| AGCAAATTCT TGAATAAACT CCCCAGCGT | 989 |

(2) INFORMATION FOR SEQ ID NO:11:

(i) SEQUENCE CHARACTERISTICS:
        (A) LENGTH: 1174 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

| | |
|---|---|
| GATAGTGCTG AAGAGGAGGG GCGTTCCCAG ACCATGGCAT CTACGGAAGG TGCCAACAAT | 60 |
| ATGCCCAAGC AGGTGGAAGT GCGAATGCCA GACAGTCATC TTGGCTCAGA GGAACCCAAG | 120 |
| CACCGGCACC TGGGCCTGCG CCTGTGTGAC AAGCTGGGGA AGAATCTGCT GCTCACCCTG | 180 |
| ACGGTGTTTG GTGTCATCCT GGGAGCAGTG TGTGGAGGGC TTCTTCGCTT GGCATCTCCC | 240 |
| ATCCACCCTG ATGTGGTTAT GTTAATAGCC TTCCCAGGGG ATATACTCAT GAGGATGCTA | 300 |
| AAAATGCTCA TTCTCCCTCT AATCATCTCC AGCTTAATCA CAGGGTTGTC AGGCCTGGAT | 360 |
| GCTAAGGCTA GTGGCCGCTT GGGCACGAGA GCCATGGTGT ATTACATGTC CACGACCATC | 420 |
| ATTGCTGCAG TACTGGGGGT CATTCTGGTC TTGGCTATCC ATCCAAGCTT GGATCACTGC | 480 |
| CCTGGGCACC GCTTCCAGTG CTGGAACTTT GCCTGTCACC TTTCGTTGCC TGGAAGAAAA | 540 |
| TCTGGGGATT GATAAGCGTG TGACTAGATT CGTCCTTCCT GTTGGAGCAA CCATTAACAT | 600 |
| GGATGGTACA GCCCTTTATG AAGCGGTGGC CGCCATCTTT ATAGCCCAAA TGAATGGTGT | 660 |
| TGTCCTGGAT GGAGGACAGA TTGTGACTGT AAGCCTCACA GCCACCCTGG CAAGCGTCGG | 720 |
| CGCGGCCAGT ATCCCCAGTG CCGGGCTGGT CACCATGCTC CTCATTCTGA CAGCCGTGGG | 780 |
| CCTGCCAACA GAGGACATCA GCTTGCTGGT GGCTGTGGAC TGGCTGCTGG ACAGGATGAG | 840 |
| AACTTCAGTC AATGTTGTGG GTGACTCTTT TGGGGCTGGG ATAGTCTATC ACCTCTCCAA | 900 |
| GTCTGAGCTG GATACCATTG ACTCCCAGCA TCGAGTGCAT GAAGATATTG AAATGACCAA | 960 |
| GACTCAATCC ATTTATGATG ACATGAAGAA CCACAGGGAA AGCAACTCTA ATCAATGTGT | 1020 |

```
CTATGCTGCA CACAACTCTG TCATAGTAGA TGAATGCAAG GTAACTCTGG CAGCCAATGG        1080

AAAGTCAGCC GACTGCAGTG TTGAGGAAGA ACCTTGGAAA CGTGAGAAAT AAGGATATGA        1140

GTCTCAGCAA ATTCTTGAAT AAACTCCCCA GCGT                                    1174
```

(2) INFORMATION FOR SEQ ID NO:12:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GATAGTGCTG AAGAGGAGGG GCGTTCCCAG ACCATGGCAT CTACGGAAGG GGACAGGATG          60

AGAACTTCAG TCAATGTTGT GGGTGACTCT TTTGGGGCTG GGATAGTCTA TCACCTCTCC         120

AAGTCTGAGC TGGATACCAT TGACTCCCAG CATCGAGTGC ATGAAGATAT TGAAATGACC         180

AAGACTCAAT CCATTTATGA TGACATGAAG AACCACAGGG AAAGCAACTC TAATCAATGT         240

GTCTATGCTG CACACAACTC TGTCATAGTA GATGAATGCA AGGTAACTCT GGCAGCCAAT         300

GGAAAGTCAG CCGACTGCAG TGTTGAGGAA GAACCTTGGA AACGTGAGAA ATAAGGATAT         360

GAGTCTCAGC AAATTCTTGA ATAAACTCCC CAGCGT                                   396
```

(2) INFORMATION FOR SEQ ID NO:13:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
GATAGTGCTG AAGAGGAGGG GCGTTCCCAG ACCATGGCAT CTACGGAAGG CCTCACAGCC          60

ACCCTGGCAA GCGTCGGCGC GGCCAGTATC CCCAGTGCCG GGCTGGTCAC CATGCTCCTC         120

ATTCTGACAC CCGTGGGCCT GCCAACAGAG GACATCAGCT TGCTGGTGGC TGTGGACTGG         180

CTGCTGGACA GGATGAGAAC TTCAGTCAAT GTTGTGGGTG ACTCTTTTGG GGCTGGGATA         240

GTCTATCACC TCTCCAAGTC TGAGCTGGAT ACCATTGACT CCCAGCATCG AGTGCATGAA         300

GATATTGAAA TGACCAAGAC TCAATCCATT TATGATGACA TGAAGAACCA CAGGGAAAGC         360

AACTCTAATC AATGTGTCTA TGCTGCACAC AACTCTGTCA TAGTAGATGA ATGCAAGGTA         420

ACTCTGGCAG CCAATGGAAA GTCAGCCGAC TGCAGTGTTG AGGAAGAACC TTGGAAACGT         480

GAGAAATAAG GATATGAGTC TCAGCAAATT CTTGAATAAA CTCCCCAGCG T                  531
```

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

```
GGCAACTGGG GATGTACA                                           18
```

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

```
CCAGAAGGCT CAAGAAGT                                           18
```

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

```
ACGCTGGGGA GTTTATTCAA GAAT                                    24
```

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:17:

```
ACCGTCCTCT GCCACCACTC T                                       21
```

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:18:

```
AGGAGGTTTG GCTTTCTGTG G                                       21
```

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:19:

```
GGTTTTTAAC ACCTGGTGCT CAA                                              23
```

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

```
CGGCTGACTT TCCATTGGCT G                                                21
```

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:21:

```
CCTGGTGCTC AAGAAAGTGT TTC                                              23
```

(2) INFORMATION FOR SEQ ID NO:22:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

```
GGATCCCGGG CCCTTTCTCA CGTTTCCAAG G                                     31
```

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:23:

```
GGATCCCGGG CCCCCTGGAA GCGGTGCCCA G                                     31
```

(2) INFORMATION FOR SEQ ID NO:24:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

-continued

TCTGTTCCAG TGCCA                                                    15

(2) INFORMATION FOR SEQ ID NO:25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TTCCTTTTAG GTGTC                                                    15

(2) INFORMATION FOR SEQ ID NO:26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

TTCAATCCAG GGTTG                                                    15

(2) INFORMATION FOR SEQ ID NO:27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

ACTCTGTTAG ATTCA                                                    15

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

CACCCAACAG GTCTG                                                    15

(2) INFORMATION FOR SEQ ID NO:29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TGTTTTTCAG GTACT                                                    15

```
(2) INFORMATION FOR SEQ ID NO:30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TTGTTCTCAG TGCTG                                                      15

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GTTCTCATAG CCTCA                                                      15

(2) INFORMATION FOR SEQ ID NO:32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TGTACCCCAG GGACA                                                      15

(2) INFORMATION FOR SEQ ID NO:33:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TTATTTTCAG GTAAC                                                      15

(2) INFORMATION FOR SEQ ID NO:34:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

GAAGGGTGAG GGATT                                                      15

(2) INFORMATION FOR SEQ ID NO:35:

(i) SEQUENCE CHARACTERISTICS:
        (A) LENGTH: 15 base pairs
```

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GTTTGGTAGG TACCT                                              15

(2) INFORMATION FOR SEQ ID NO:36:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

CACAGGTAAG ACTAC                                              15

(2) INFORMATION FOR SEQ ID NO:37:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

AACAGGTAAC CCAGA                                              15

(2) INFORMATION FOR SEQ ID NO:38:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

CTTAGGTAGG CCAGC                                              15

(2) INFORMATION FOR SEQ ID NO:39:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

ATGTGGTAAG TGGCC                                              15

(2) INFORMATION FOR SEQ ID NO:40:

(i) SEQUENCE CHARACTERISTICS:
        (A) LENGTH: 15 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:40:

TCCAGGTAGA GAACA                                                15

(2) INFORMATION FOR SEQ ID NO:41:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:41:

GTAAGGTGAG AAGGG                                                15

(2) INFORMATION FOR SEQ ID NO:42:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:42:

CTGCTGTAAG TGTCT                                                15

(2) INFORMATION FOR SEQ ID NO:43:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:43:

GCAAGGTACA TTTCC                                                15

(2) INFORMATION FOR SEQ ID NO:44:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:44:

AAGCGCCATC CCCGCGGGCG                                           20

(2) INFORMATION FOR SEQ ID NO:45:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:45:

```
GGAGCTCCCC GCCAAGCGCC                                          20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

GAAGTGCGAA TGCCAGACAG                                          20

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

GGGGGTCATT CTGGTCTTGG                                          20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

CAAAGCACAG CGCCCCGAGC                                          20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

ATCTATCCAT CCAGGCAATC                                          20

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

CTACGGAAGG TGCCAACAAT                                          20

(2) INFORMATION FOR SEQ ID NO:51:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

CTACGCAAGG TGCCAACAAT                                                     20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

GGCCGCCATC TTTATAGCCC                                                     20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

GGCCGCCATC TTTATAGCCC                                                     20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

GTATTACATG TCCACGACCA                                                     20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

CAGTGCCGGG CTGGTCACCA                                                     20

(2) INFORMATION FOR SEQ ID NO:56:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:56:

CAAGCTGATG GTGGATTTCT                                              20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

CTGGCATTTT CCAAGCTTGG                                              20

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

ACTGGCTGCT GGACACGATG                                              20

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

TGACTGTAAG CCTCACAGCC                                              20

(2) INFORMATION FOR SEQ ID NO:60:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

AGCCCCGCAG CAAAGCACAG GTGGCAGCGG CTGCAGGGGC GCATCGCCGG CGTGCGCCCT    60

CCTGCAGCCC TGGGCGCATC GCTCTCTCGG GGAAGCCACC CTCGGAGCCC CCGGAGCTCC   120

CCGCCAAGCG CCATCCCCGC GGGCGGAGGG GAGCGCGGGT CGCGCGCCGT GGAGAGCCGG   180

GACGCGGATT AGCGCCCGCA GGAGCCTCCT GCGCCCGTTG AGGCGCTAAA GGGCTTACCC   240

CCGGAGGCGG GTGGAAGGGC GGGCAGAGGC TCCTCTTAAA TACCGCTCCC GGCCGCACTT   300
```

```
-continued

CGCGCTCACC CCGGCGTCCG CTTTCTCCCT CGCCCACAGC TGCCGGATAG TGCTGAAGAG    360

GAAGGGGCGT TCCCCAGACC ATG                                            383
```

ABERRANT GLUTAMATE TRANSPORTERS AND METHODS OF USE

GOVERNMENT SUPPORT

This work described herein was supported by a grant from the National Institutes of Health. Therefore, the U.S. Government may have certain rights in the invention.

BACKGROUND OF THE INVENTION

1. Field of the Invention

The present invention features methods for detecting at least one specified neurological disorder in a subject. In one aspect, the invention relates to novel polynucleotides for detecting the neurological disorder. In a related aspect, the invention provides methods for identifying, analyzing, and using the polynucleotides. Further provided are screening methods for detecting therapeutic compounds with capacity to treat the neurological disorder. The present invention has a variety of uses including detecting a specified motor neuron disorder in a patient.

2. Background

Neurological disorders can significantly impact the central nervous system (CNS) and motor neuron units. For example, certain neurological disorders of the CNS are known to adversely affect the brain and associated structures. Neurological disorders affecting motor neuron units have been grouped into motor neuron diseases and peripheral neuropathies. See generally Kandel, E. R. et al; (1991) in *Principles of Neuroscience*, Appleton & Lange, Norwalk, Conn.; and Rowland, L. P. (ed.) (1982) in *Human Motor Neuron Diseases*. New York. Raven Press.

An illustrative motor neuron disease is amyotrophic lateral sclerosis (ALS). ALS has been reported to be a chronic neuromuscular disorder having recognized clinical manifestations. For example, it has been suggested that degeneration of cortical and spinal/bulbar motor neurons may play a key role in the disorder. ALS is nearly always fatal. About 95% of all ALS cases are sporadic, with many of the remaining cases showing autosomal dominant inheritance. See e.g., Kuncl R. W. et al., (1992) *Motor Neuron Diseases In Diseases of the Nervous System*, Asbury et al. eds. (Philadelphia W. B. Saunders) pp. 1179–1208; Brown, R. H., (1996) *Amer. Neurol.* 30:145; Siddique, T. and Deng., H. X. (1996) *Hum. Mol. Genetics* 5:1465).

Specific CNS disorders have been also described. In particular, some have been attributed to cholinergic, dopaminergic, adrenergic, serotonergic deficiencies or combinations thereof. CNS disorders of severe impact include pre-senile dementia (sometimes referred to as Alzheimer's disease (AD) or early-onset Alzheimer's disease), senile dementia (dementia of the Alzheimer's type), Parkinson's disease (PD), and Huntington's disease (HD, sometimes referenced as Huntington's chorea). Such CNS disorders are well-represented in the human population. See generally; Gusella, J. F. et al. (1983) *Nature* 306: 234; Borlauer. W. and Jprmuloewoca. P. (eds.) (1976); *Adv. in Parkinsonism: Biochemistry, Physiology, Treatment. Fifth International Symposium on Parkinson's Disease* (Vienna) Basel: Roche; and references cited therein.

Significant attention has been directed towards understanding the etiology of motor neuron diseases. For example, abnormal levels of certain excitotoxic neurotransmitters have been reported to adversely contribute to many motor neuron diseases. In particular, glutamate-mediated excitotoxicity is recognized to have a critical role in ALS. See e.g., Rothstein J. D. et al., (1990) *Ann. Neurol.* 28: 18.; Rothstein J. D. et al. (1992) *N. Engl. Med.* 326: 1464; Rothstein J. D. et al. (1993) *PNAS (USA)* 90: 6591; and Lacomblez, L. et al., (1996) *Lancet* 347: 1179.

There has been substantial efforts towards understanding mechanisms for reducing glutamate levels in the nervous system. For example, high-affinity, sodium-dependent glutamate transport is one reported means of inactivating glutamate. In particular, astrocytic excitatory amino acid transporter 2 (EAAT 2) proteins are believed to have substantial functions in that inactivation. See e.g., Rothstein J. D. et al. (1994) *Neuron* 28: 18; Rothstein J. D. et al., (1995) *Ann. Neurol.* 38: 78, and references cited therein.

In particular, investigations have suggested that EAAT 2 is a predominant glutamate transporter. More particularly, certain antisense knockdown studies have been reported to demonstrate that EAAT 2 loss can lead to excitotoxic neuronal degeneration and progressive motor impairment. Studies of ALS and other neurodegenerative disorders have related impaired glutamate transport to loss of the EAAT 2 protein. In particular, up to 60% to 70% of the sporadic ALS patients examined have a 30% to 95% loss of the EAAT 2 protein. See e.g., Haugeto et al., supra; Rothstein J. D., et al., (1996) *Neuron* 16: 675; Bristol, L. A. and Rothstein, J. D. (1996) *Ann. Neurol.* 39: 676.

There have been attempts to treat or prevent neurological disorders of the CNS and the motor neuron units. However, most existing therapies do not always stem the development or severity of the disorders in afflicted patients. See e.g., Rowell, (1987) *Adv. Behav. Biol.* 31: 191; Rinne, et al. *Brain Res.* (1991) 54: 167; U.S. Pat. No. 5,210,076 to Berliner; Yurek, D. M. (1990) *Ann. Rev. Neurosci.* 13: 415, and Rowland et al. supra.

Substantial research effort has focussed on developing effective methods for detecting neurological disorders in patients. However, many existing methods are not always effective or reliable. For example, some methods are optimized to analyze post-mortem samples. Such methods provide little benefit for the afflicted patient. Other methods rely on testing living patients for specific cognitive or motor skills. However, such tests can be difficult to perform or interpret in some settings.

Accordingly, there is a need in the field for effective and reliable methods for detecting neurological disorders in a living patient. There is general recognition that such methods would positively impact many existing therapies. It would be particularly desirable to have methods for detecting specific neurological disorders in a living patient before disease onset or at an early stage of disease progression.

SUMMARY OF THE INVENTION

The present invention features methods for detecting at least one specified neurological disorder in a subject. In one aspect, the methods include obtaining a biological sample from the subject and detecting at least one type of aberrant human glutamate transporter 2 mRNA in the sample. Presence of the aberrant mRNA is indicative of the neurological disorder in the subject. The invention also relates to novel polynucleotides that can be used to detect the neurological disorder. Further provided are methods for isolating a variety of aberrant human glutamate transporter 2 polynucleotides. The invention also provides screening methods for detecting compounds useful in the diagnosis or treatment of specified neurological disorders. The present invention has a variety of uses including monitoring efficacy of a therapy for treating the neurological disorder.

In general, we have discovered aberrant human glutamate transporter 2 mRNAs in patients suffering from or suspected of suffering from a specific neurological disorder. It was found that incidence of the aberrant mRNAs substantially increased in affected nervous system regions. For example, incidence of the aberrant mRNAs could be detected in patients afflicted with a specific motor neuron disease. Significantly, the present invention provides sensitive and reliable methods for detecting specific neurological disorders in living patients with minimal impact to the nervous system.

The term "human glutamate transporter 2" is sometimes abbreviated herein as "EAAT 2". The term "EAAT 2" will be particularly used to refer to the human astroglial glutamate transporter 2 gene as well as normal or aberrant polynucleotides derived from that gene.

As will be discussed more fully below, aberrant EAAT 2 polynucleotides of this invention are novel molecular markers that can be used to detect specific neurological disorders. In particular, aberrant EAAT 2 mRNAs of this invention are intron-retention or exon-skipping variants of normal EAAT 2 mRNA. The aberrant EAAT 2 mRNAs were found in a majority of patients that were known to have or were suspected of having a specified neurological disorder. However, the aberrant EAAT 2 mRNAs were not found in control samples obtained from apparently healthy and non-affected donors. Accordingly, detection of at least one type of aberrant EAAT 2 mRNA in the patient is taken to be indicative of the neurological disorder in that patient.

The neurological disorders that can be detected in accord with the present invention include specific disorders that have been reported to be associated with excitotoxicity. Particularly included are specified neurological disorders affecting motor neuron function. Specifically included are neurological disorders impacting the CNS or motor neuron units such as amyotrophic lateral sclerosis (ALS), Huntington's disease (HD), Parkinson's disease (PD), and Alzheimer's disease (AD). As will be pointed out below, in selected disorders, at least one type of aberrant EAAT 2 mRNA has been detected in a majority of patients that have or were suspected of having the disorder. As noted, those aberrant mRNAs were not detected in apparently healthy and non-affected donors.

The present invention has a number of important advantages. For example, the invention can be used to detect a specified neurological disorder in a living patient with minimal impact to the nervous system. For example, one embodiment of the present invention features a method for detecting at least one type of aberrant EAAT 2 mRNA in a replaceable nervous system fluid that can be readily obtained from the patient. In this embodiment, presence of at least one type of aberrant EAAT 2 mRNA in the fluid is indicative of the neurological disorder in that patient.

In some instances, the patient to be tested may not yet manifest overt signs of any neurological disorder. In this instance, the methods of the invention can serve as an indicator of predisposition for or susceptibility to the disorder. In contrast, many prior methods for detecting neurological disorders rely on difficult cognitive or motor tests. Other more definitive tests are typically formatted to characterize post-mortem nervous system tissue. Unlike these prior methods, the present invention provides reliable and sensitive methods for detecting neurological disorders while the patient is living. Significantly, opportunities for early medical intervention are increased by practice of the invention.

In one aspect, the present invention provides an assay method for detecting at least one specified neurological disorder in a patient who has or is suspected of having that neurological disorder. The method generally involves obtaining a biological sample from the patient and detecting at least one type of aberrant EAAT 2 mRNA in the sample as indicative of the neurological disorder. In one embodiment of the method, detection of the aberrant EAAT 2 mRNA is achieved by amplifying the sample in a polymerase chain reaction (PCR) or suitable related method. Typically, the amplification method selected will be sufficient to make complementary polynucleotides, typically complementary DNA (cDNA), from the sample. That is, the PCR or related method is used to make nucleic acid copies of the mRNA which copies are usually cDNA copies but can be at least partially RNA copies (cRNA) in some instances. A preferred amplification method is a reverse transcriptase-PCR (RT-PCR) method using at least two oligonucleotide primers. In a particular embodiment, amplified cDNA made from aberrant EAAT 2 mRNA (if present in the sample) is sequenced and the resulting DNA sequence is compared to the sequence of the normal EAAT 2 cDNA (FIGS. 1 A–C and SEQ ID NO: 1). The comparison allows determination of the aberrant EAAT 2 mRNA structure in most instances. In many cases, a suitable control sample is included to provide suitable co-amplification of normal EAAT 2 mRNA. Preferred control samples generally provide a baseline for any basal expression of the normal EAAT 2 mRNA. In another particular embodiment, DNA sequence from the cDNA is substantially homologous or identical to specific aberrant EAAT 2 cDNA sequences disclosed below.

In another aspect of the present invention, assay methods are provided for detecting the neurological disorder in the patient in which aberrant EAAT 2 mRNA is detected by making a polynucleotide library from the biological sample. In one embodiment, the polynucleotide library is a cDNA library and the methods include detecting in the library at least one nucleic acid that includes a sequence substantially homologous or identical to specified aberrant EAAT 2 cDNA sequences disclosed below.

Further provided by the present invention are methods for detecting at least one specified neurological disorder in the patient in which the methods involve obtaining a first biological sample from a suitable control donor and a second biological sample from the patient, amplifying nucleic acid in the samples independently, and detecting in the second sample any amplified nucleic acid as indicative of the neurological disorder in the patient. In one embodiment of the method, mRNA in the first and second samples is independently amplified under conditions capable of producing cDNA from at least one type of aberrant EAAT 2 mRNA (if present) in the sample. In this embodiment, the aberrant mRNA includes intron sequence from the EAAT 2 gene. The method is especially useful for detecting specific aberrant EAAT 2 mRNAs which retain at least one intron or intron fragment from the EAAT 2 gene. Presence of a suitable amplification product in the second sample, when compared to the first sample (control), is an indication of the neurological disorder in the patient.

It will be appreciated that in instances where a baseline level of normal EAAT 2 gene expression has been established in the control donor or group of such donors it will not always be necessary to obtain the first biological sample. In such cases, the method can be performed by manipulating the second sample and comparing results obtained from the second sample to the baseline.

The present invention provides additional methods for detecting at least one specified neurological disorder in the patient which includes obtaining a first biological sample from a control donor and a second biological sample from the patient and detecting at least one type of aberrant EAAT 2 mRNA in the second sample. In one embodiment, nucleic acid in the first and second samples is independently amplified under conditions capable of producing complementary nucleic acid from the mRNA, typically cDNA. In this embodiment, presence of at least one amplification product in the second sample that is substantially smaller than its corresponding amplification product in the first sample is indicative of the neurological disorder in the patient. That is, presence of an amplification product in the second sample which has fewer nucleotides than the corresponding amplification product in the first sample is an indicator of the disorder. That determination can be made by standard nucleic acid sizing manipulations such as those found below. The method is particularly useful for detecting exon-skipping EAAT 2 mRNAs in the second sample. More particularly, the method is useful for identifying aberrant EAAT 2 mRNAs that are missing at least a fragment of an EAAT 2 gene exon up to an entire exon and including loss of multiple exons. The multiple exons can be contiguous or non-contiguous with respect to the normal EAAT 2 gene.

As noted above, in some instances it will not be necessary to obtain the first biological sample in cases where a suitable baseline of normal EAAT 2 gene expression has been established.

Additionally provided are methods for detecting at least one specified neurological disorder in the patient which methods include obtaining a biological sample from the patient and detecting at least one type of aberrant human EAAT 2 mRNA in the sample. In one embodiment, the method includes contacting the sample with a nucleic acid that includes sequence complementary to at least a fragment of an EAAT 2 gene intron up to an entire intron. Generally, the contact will be under conditions conducive to forming a specific binding complex between the nucleic acid and any aberrant EAAT 2 mRNA in the sample. Preferred use of the method requires that the aberrant EAAT 2 mRNA in the sample include a retained intron or a retained fragment of the intron. In this method, detection of the specific binding complex is indicative of the neurological disorder in the patient.

In a particular embodiment of the method, detection of the specific binding complex can be achieved by one or a combination of different strategies including treating the binding complex with a nuclease, typically a single-strand nuclease, and then identifying any hydrolyzed nucleic acid in the binding complex as indicative of the neurological disorder. Alternatively, the detection can be achieved by standard hybridization techniques such as those specified below.

Preferred use of the present methods will typically include RT-PCR amplification of specified nucleic acid sequence in biological samples of interest, although other PCR methods or recombinant methods such as cloning can be used in some instances for the amplification. Additionally, it is generally preferred that the biological samples include detectable levels of RNA; preferably mRNA; and more preferably normal EAAT 2 mRNA, aberrant EAAT 2 mRNA, or both. Additionally preferred is use of a biological sample that includes or consists of a replaceable nervous system fluid, preferably cerebrospinal fluid (CSF) which when taken from the patient will, by conventional medical procedures, minimally impact the nervous system. However in other embodiments of the invention, biological samples such as nervous system tissue samples, e.g., biopsies, tissue slices and the like can be used in some instances. Additionally preferred is use of the present invention to detect specific neurological disorders (ALS, AD, HD and PD). A particularly preferred neurological disorder for purposes of this invention is ALS.

The invention further provides methods for isolating an aberrant EAAT 2 polynucleotide which methods generally include obtaining a first biological sample from a control donor and a second biological sample from the patient. In one embodiment, the RNA samples include detectable amounts of RNA and particularly mRNA, and the method involves making cDNA in each of the first and second samples. Production of the cDNA can be accomplished by nearly any suitable method including PCR and particularly RT-PCR using at least two specified oligonucleotide primers. In this method, a first portion of the cDNA is introduced into suitable control cells under culture conditions sufficient to express the cDNA in the control cells. A second portion of the cDNA is introduced into suitable test cells under the same or closely related conditions. The test and control cells are then independently assayed for glutamate transport as discussed below.

Reference herein to a "standard glutamate transport" assay or similar term is meant to denote a preferred assay for detecting glutamate transport in suitable cultured cells. In particular, a substantial reduction in glutamate transport in the test cells described above is indicative of presence of at least one type of aberrant EAAT 2 cDNA in the second sample. Preferably, the glutamate transport is reduced in the test cells (relative to the control cells) by at least about 10%, more preferably at least about 20%, 30%, or about 40%, and still more preferably at least about 50%, 60%, 70%, 80%, 90%, or 99% or more up to about 100% relative to glutamate transport in the control cells.

In a particular embodiment of the method, cDNA produced from the first and second samples is co-introduced into the test cells, e.g., by combining the cDNA from each of the samples prior to the co-introduction. The test cells are subsequently cultured under conditions sufficient to express each of the cDNAs in the test cells. The test cells and control cells are then independently assayed to analyze glutamate transport, e.g., in the standard glutamate transport assay. A substantial reduction or absence of glutamate transport in the test cells is indicative of presence of at least one type of aberrant human EAAT 2 cDNA in the second sample.

As will be explained more fully in the discussion that follows, it has been found that specific aberrant EAAT 2 cDNAs of this invention, when expressed in suitable test cells, are capable of significantly decreasing or eliminating expression from the co-introduced normal EAAT 2 cDNA. That reduction can be detected and quantified if desired by several means including conducting the standard glutamate transport assay described below. Decreased expression of the normal EAAT 2 gene (or introduced cDNA) will sometimes be referred to as "dominant down-regulation" or a related term to denote capacity of the aberrant EAAT 2 cDNA to decrease expression of the normal EAAT 2 gene or (cDNA). A specific aberrant EAAT 2 cDNAs with such capacity is described below.

As will be fully appreciated, it will not always be necessary to obtain the first biological sample from the control donor or to make the control cells in instances where a suitable baseline level of glutamate transport has already been established.

As noted, the methods of the present invention are highly useful for detecting at least one or specified neurological disorder in a patient, which patient has or is suspected of having the neurological disorder. In one embodiment, the invention can be employed to confirm presence of the neurological disorder. In a particular embodiment more specifically described below, the present invention embraces certain hybridization chips that can be employed to detect the neurological disorder.

In another embodiment, the invention can be used to evaluate efficacy of a therapy employed to treat a patient suffering from a specified neurological disorder such as ALS. In this embodiment, levels of normal EAAT 2 protein, mRNA, or both are determined in a biological sample obtained from the patient before (control), during, and/or following treatment. An increase in the level of the normal protein, mRNA (or both) will be indicative of efficacious therapy. Preferred are therapies formatted to treat ALS and particularly therapies including or consisting of administration of Rilutek™ (riluzole).

The present invention further pertains to a polynucleotide (RNA, mRNA, cDNA, genomic DNA, or a chimera thereof) that includes or consists of an isolated nucleic acid that encodes an aberrant EAAT 2 mRNA or the complement thereof (RNA, DNA, or a chimera thereof). In one embodiment, the isolated nucleic acid includes a DNA complement of the aberrant EAAT 2 mRNA which complement can be cDNA. The polynucleotide can be derived (whole or in part) from a variety of sources, e.g., by amplifying a biological sample of interest. In a particular embodiment, the amplification is suitably conducted by PCR or a related method with RT-PCR being a preferred amplification method.

In one embodiment, the isolated nucleic acid is preferably inserted into a suitable recombinant vector such as a suitable recombinant DNA vector. It is preferred that the vector be capable of propagating the nucleic acid in a suitable prokaryotic or eukaryotic host cell. Additionally preferred recombinant vectors are capable of expressing that isolated nucleic acid as RNA and preferably mRNA, in a suitable cell expression system. The recombinant vector typically includes control elements operably linked to the inserted nucleic acid (e.g., promoter, leader, and/or enhancer elements) which control elements can be selected to optimize replication and/or transcription of the vector in the cells.

Polynucleotides of the invention generally include an isolated nucleic acid sequence that encodes an aberrant EAAT 2 mRNA of this invention or the complement thereof. In one embodiment, the polynucleotides include an isolated nucleic acid sequence that is substantially homologous to at least one aberrant EAAT 2 cDNA. See in the drawings below and SEQ ID NOS 3 & 5–13, respectively, in order of appearance (inclusive). In a specific embodiment, the isolated nucleic acids include or consists of cDNA and have a length of between about 50 to about 100 nucleotides, about 100, 200, 500, 1000, 2000 to about 2500 nucleotides, as determined by standard nucleic acid sizing methods as disclosed below. In another embodiment, the isolated nucleic acid includes or consists of RNA and particularly mRNA that is also substantially homologous to the specific cDNA sequences and which have having substantially the same length as the cDNA.

Particularly preferred are the aberrant EAAT 2 cDNA sequences specifically shown in the drawings and in SEQ ID NOS 3 & 5–13, respectively, in order of appearance. Additionally preferred are those sequences that are capable of significantly reducing glutamate transport in the standard glutamate transport assay. For example, specific use of the standard glutamate transport assay includes co-introduction in suitable cells of the aberrant EAAT 2 cDNA sequence with the normal EAAT 2 cDNA (SEQ ID No. 1) or a suitable fragment thereof. Preferably, the aberrant EAAT 2 cDNA sequence is capable of reducing the glutamate transport in the cells by at least about 10%, preferably at least about 20%, 30%, or about 40%, more preferably about 50%, 60%, 70%, 80%, 90%, 99% or more up to about 100% relative to glutamate transport in a suitable control assay.

Additionally preferred are complement sequences (DNA or RNA) at least substantially homologous and preferably identical to the DNA sequences shown in SEQ ID NOS 3 & 5–13, respectively, in order of appearance.

As will become more apparent below, many aberrant EAAT 2 polynucleotides of the invention are not capable of producing significant levels of polypeptide under most conditions. However in some cases, significant amounts of the polypeptide may be produced from a particular polynucleotide of interest. That polypeptide can be at least partly functional and may be almost totally functional as determined by the standard glutamate transport assay. For example, the polypeptide will exhibit at least about a 50%, 60%, 70%, or at least about an 80%, up to at least about a 90% or at least about a 95% or more reduction in glutamate transport when compared to a suitable control. The polypeptides will sometimes be referred to herein as a "aberrant polypeptides" or a related term to denote less than about 100% of the activity of the normal EAAT 2 polypeptide.

Additionally provided are antibodies (polyclonal and monoclonal) that are capable of specifically binding to an aberrant polypeptide.

Further provided are cultured host cells which have been transformed, transfected or infected either transiently or stably by at least one recombinant vector of the invention which vector includes an isolated nucleic acid that is capable of encoding an aberrant EAAT 2 mRNA of the complement thereof (DNA or RNA).

The present invention also provides useful oligonucleotide primers, typically single-stranded primers, which oligonucleotide primers are complementary to an RNA splice junction of an aberrant EAAT 2 polynucleotide. As will be shown in the discussion and drawings which follow, an RNA splice junction is typically referenced with respect to a cDNA sequence. Preferred are RNA splice junctions that are unique to an aberrant EAAT 2 cDNA and are not found in the normal EAAT 2 cDNA sequence (FIGS. 1 A–C and SEQ ID NO. 1). Accordingly, the oligonucleotide primers will not usually hybridize to a normal EAAT 2 gene, cDNA or mRNA sequence under normal hybridization conditions specified below. The oligonucleotide primers can be employed, e.g., to detect or amplify an aberrant EAAT 2 mRNA of interest.

Additional polynucleotides of the present invention have important uses. For example, the invention provides for recombinant vectors that include an isolated nucleic acid as discussed. The recombinant vectors can be used to produce significant amounts of nucleic acid sequence that can be sense or anti-sense, single-stranded or double-stranded. Generally, normal mRNA transcribed from DNA is referred to as the "sense" RNA strand and oppositely oriented RNA is termed antisense RNA. Antisense polynucleotides, then, refer to sequences of DNA or RNA which can bind in a Watson-Crick fashion to a sequence on a target mRNA. See generally Bentley, D. L. and Groudine, M. (1986) *Nature* 321:702; and Kimelman, D. *Gene regulation: Biology of Antisense RNA and DNA*, R. P. Erickson, J. G. Izant, eds. (Raven Press, New York).

Aberrant EAAT 2 mRNA in a biological sample will sometimes be referred to herein as a "target" to denote potential for specific binding between a polynucleotide of interest, e.g., a suitable anti-sense RNA, and the aberrant EAAT 2 mRNA in the sample.

In one preferred embodiment, the recombinant vectors include DNA sequences that encode an anti-sense RNA which RNA is substantially homologous to specified aberrant EAAT 2 cDNA sequences described below. In this instance it will be understood that the anti-sense RNA will usually include a uracil (U) in place of thymidine (T) where the cDNA sequence has a thymidine. In a preferred embodiment, the anti-sense RNA has a length of at least about 20 to about 50 nucleotides, at least about 100 to about 250 nucleotides, at least about 300 to about 700 nucleotides, or at least about 1000 to about 2000 and up to about 2500 nucleotides as determined by standard polynucleotide sizing methods. In most cases, the length of the anti-sense RNA will be guided by intended use including the length of the target.

The antisense RNA encoded by specific recombinant vectors of this invention is usually designed to undergo complementary base pairing (hybridization) with the target, rendering the target essentially unavailable for translation in most cases. In some instances, the antisense RNA will render the target susceptible to degradation, thereby substantially reducing the amount of the target in relevant cells or tissue. Accordingly, the recombinant vectors of the invention can be used to control undesired aberrant EAAT 2 mRNA in the cells or tissue.

Specific recombinant vectors of this invention that are capable of producing anti-sense RNA complementary to a specific aberrant EAAT 2 mRNA (or more than one of such mRNA) can be used therapeutically to reduce levels of the target in vivo or in vitro. For example, in one embodiment, a desired recombinant vector is administered to a patient in need of reduced levels of the target. In this case, the administration is sufficient to reduce levels of the target mRNA in the patient. Presence of the anti-sense RNA in the cells or tissue can in some settings boost expression of the normal EAAT 2 gene therein. That increase in expression can be monitored by a spectrum of tests including the standard glutamate transport assay.

In another embodiment, the recombinant vector is formatted to produce anti-sense DNA of about the same size as the anti-sense DNA.

In addition, the polynucleotides of this invention and particularly the isolated nucleic acids and recombinant vectors described herein can be used as important controls for detecting and analyzing normal and aberrant EAAT 2 gene expression in vitro and in vivo.

Additionally provided by the present invention is a solid support to which has been bound at least one of specified polynucleotide of this invention. In another embodiment, a plurality of specified polynucleotides, the same or different, are bound to the solid support. In a particular embodiment, the solid support is a hybridization chip (sometimes referred to as a "micro-chip" or like term) that is capable of detecting at least one aberrant EAAT 2 polynucleotide, typically an aberrant EAAT 2 mRNA in a biological sample obtained from a patient.

Further provided are methods for isolating a nucleic acid and particularly a cDNA that is complementary to at least one aberrant EAAT 2 mRNA of this invention. The methods generally involve obtaining a suitable biological sample from a patient and preparing cDNA from the sample. Preparation of the cDNA can be achieved by several methods including PCR and particularly RT-PCR. The cDNA produced can be purified if needed and can be inserted into a suitable recombinant vector by standard techniques. Alternatively, the cDNA can be used in linear form, e.g., as a detectably-labeled probe, without insertion into the recombinant vector.

Recombinant vectors of the invention can be introduced into suitable cells or groups of such cells including tissue or organs if desired either in vitro or in vivo. Preferably the cells are capable of expressing the recombinant vector at detectable levels. Host cells comprising the vectors can be cultured in medium capable of supporting propagation and/or expression of the vectors in the cells. The cells can be eukaryotic cells, preferably mammalian cells, that are capable of expressing desired sequences in the recombinant vector. In some instances it will be desirable to introduce the vector into a suitable prokaryotic host e.g., bacteria to propagate the vector.

Isolated nucleic acids and polypeptides of the invention can be obtained as a substantially pure preparation if desired. That is, the nucleic acids and polypeptides can be isolated in substantially pure form by standard methods and can be provided as sterile preparations if desired. Methods for providing substantially pure preparations of nucleic acids and polypeptides are discussed below.

Additionally provided are methods for identifying a compound useful in the treatment or diagnosis of at least one of the neurological disorders specified herein. In one embodiment, the method includes contacting a suitable cultured cell with at least one candidate compound and detecting an increase in normal EAAT 2 polypeptide activity as indicative of the compound. Typically, the cultured cell will include at least one aberrant EAAT 2 polynucleotide, e.g., mRNA. It is generally preferred that the cultured cell be capable of expressing normal EAAT 2 mRNA, e.g., by methods involving transient or stable expression of the normal EAAT 2 cDNA (FIG. 1 and SEQ ID NO 1). Alternatively, the cultured cell may naturally express the normal EAAT 2 gene at suitable levels. In a particular embodiment, the cultured cell includes at least one aberrant EAAT 2 cDNA that is capable of being expressed at the mRNA or protein level in the cultured cell.

In preferred embodiments, the compound is capable of boosting expression of the normal EAAT 2 polypeptide by at least about 20%, at least about 30% to about 50%, preferably at least about 60%, 70%, 80%, 90%, or about 100% or (more relative to a suitable control) as determined, e.g., by a Western blot or by the standard glutamate transport assay. Additionally preferred are compounds that are capable of increasing normal EAAT 2 mRNA levels by at least about 10%, preferably at least about 20%, 30%, 40% to about 50%, more preferably at least about 60%, 70%, 80%, 90%, or about 100% or more relative to a suitable control as determined, e.g., by quantitative PCR or Northern blots.

The invention further provides methods for treating or preventing a neurological disorder in a patient. In one embodiment, the method includes administering to the patient a therapeutically effective amount of a recombinant vector of the invention which is capable of expressing anti-sense mRNA that can specifically bind target. The recombinant vector can be administered to the patient either as the sole active agent or in combination with other agents including additional recombinant vectors as provided herein.

Additionally provided are kits useful in the detection or treatment of at least one specific neurological disorder in a patient.

The invention also features a polynucleotide library including nucleic acid sequence encoding a sequence substantially homologous or identical to at least one of the aberrant EAAT 2 polynucleotides disclosed herein.

All documents disclosed herein are incorporated by reference in their entirety. The following non-limiting examples are illustrative of the invention.

BRIEF DESCRIPTION OF THE DRAWINGS

FIGS. 1 A–C show the sequence of the human astrocytic EAAT 2 cDNA and polypeptide sequence (SEQ ID NOS 1 & 2).

FIGS. 2 A–B show the sequence of an aberrant EAAT 2 cDNA sequence, with a retained intron sequence (SEQ ID NOS 3 & 4).

FIG. 3 is a drawing showing an aberrant EAAT 2 cDNA sequence with skipped exon sequence (SEQ ID NO: 5).

FIG. 4 is a drawing showing an aberrant EAAT 2 cDNA sequence with skipped exon sequence (SEQ ID NO: 6)

FIG. 5 is a drawing showing an aberrant EAAT 2 cDNA sequence with skipped exon sequence (SEQ ID NO: 7).

FIG. 6 is a drawing showing an aberrant EAAT 2 cDNA sequence with skipped exon sequence (SEQ ID NO: 8).

FIG. 7 is a drawing showing an aberrant EAAT 2 cDNA sequence with skipped exon sequence (SEQ ID NO: 9).

FIG. 8 is a drawing showing an aberrant EAAT 2 cDNA sequence with skipped exon sequence (SEQ ID NO: 10).

FIG. 9 is a drawing showing an aberrant EAAT 2 cDNA sequence with skipped exon sequence (SEQ ID NO: 11).

FIG. 10 is a drawing showing an aberrant EAAT 2 cDNA sequence with skipped exon sequence (SEQ ID NO: 12).

FIG. 11 is a drawing showing an aberrant EAAT 2 cDNA sequence with skipped exon sequence (SEQ ID NO: 13).

FIG. 12 is a table showing exon positions, RNA splice acceptor sequences (SEQ ID NOS 24–33 respectively, in order of appearance) and RNA splice donor sequences (SEQ ID NOS 34–43 respectively, in order of appearance) of the normal EAAT 2 gene sequence.

FIG. 13B is a schematic drawing showing sequence analysis of truncated EAAT 2 transcripts (SEQ ID NOS 44–59, respectively, in order of appearance). It will be appreciated that each of the sequences shown (sometimes referenced as $B_1$ to $B_8$) are representative of larger sequences (see FIGS. 3–11 and SEQ ID NOS 5–13, respectively, in order of appearance). In the right panel, twenty nucleotides on both sides of each internal deletion transcript are displayed. Arrows indicate splicing junctions. Sequences between the arrows are spliced out. Dashed lines indicate nucleotides within the deleted sequences. A schematic representation of the deleted regions is presented in the right panel. Cross-hatched boxes represent regions of missing RNA sequence.

FIG. 14A is a representation of a Western blot and a Southern blot of RT-PCR reactions. The figure shows that aberrant mRNA species are present in ALS, but not control motor cortex.

FIG. 14B is a representation of a Southern blot of RT-PCR reactions. The blot shows an aberrant mRNA species in ALS but not control motor cortex.

FIGS. 15A–15H are representations of in situ hybridization of partial intron 7-retention mRNA in motor cortex. Immunohistochemistry and in situ hybridization studies were performed on 3 different specimens. Scale bar for A, B, C, G, H=0.1 mm; scale bar for D, E, F=0.1 mm.

FIG. 20 is a drawing showing 5'-untranslated nucleotides from the normal human glutamate transporter 2 gene (SEQ ID NO: 60). The reported transcription start site is indicated.

DETAILED DESCRIPTION OF THE INVENTION

Figure 13A:
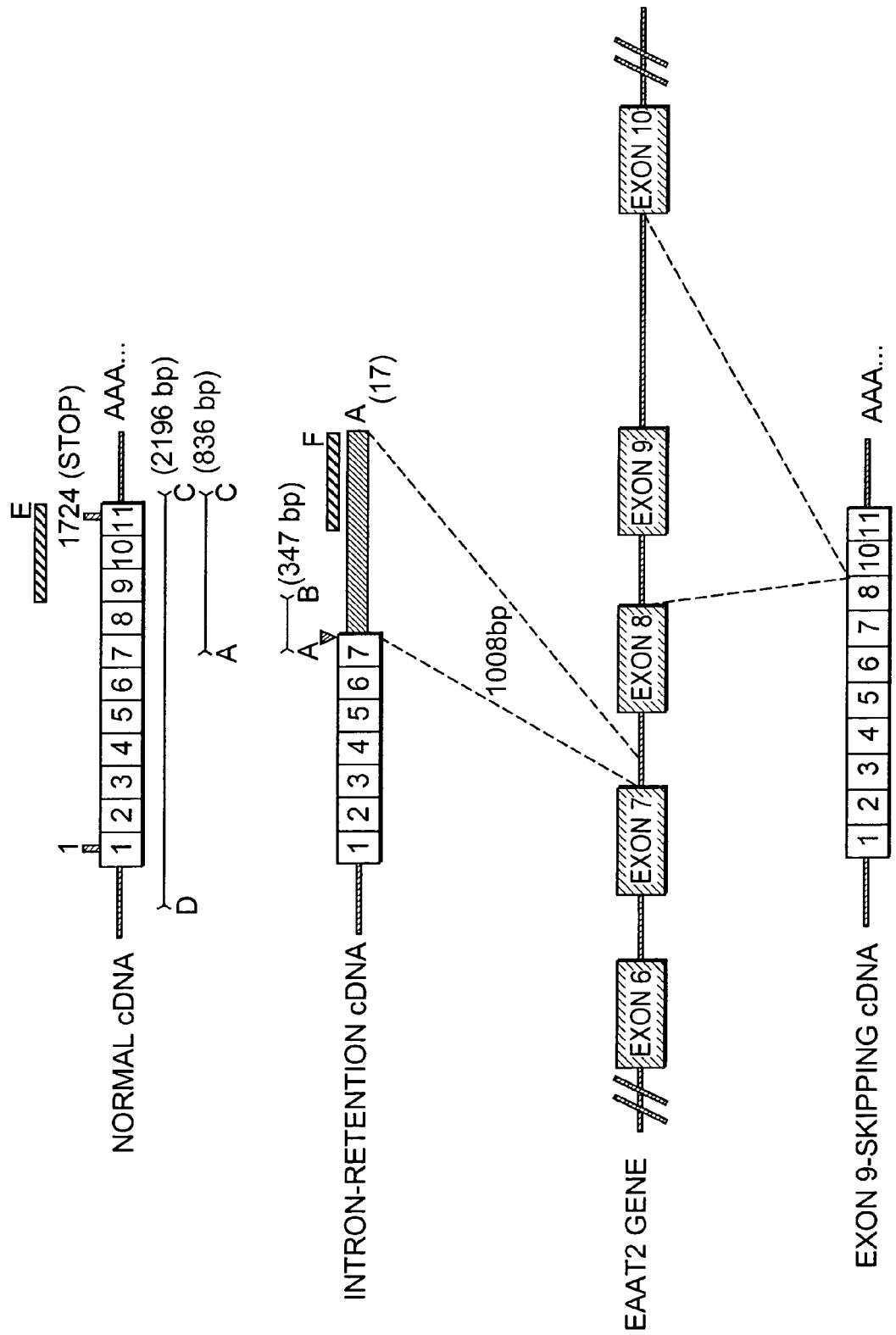
FIG. 13A is a schematic drawing showing some aberrant EAAT 2 mRNAs in relation to the normal EAAT 2 gene sequence. Numbered boxes represent individual exons. The connected arrow heads indicate the primer regions used for RT-PCR. The hatched bars indicate the regions used to prepare probes for in situ hybridization. The triangle indicates a Hind III site used as an insertion site for constructing an internal control plasmid pE2F.

As summarized above, the present invention provides highly useful methods for detecting at least one specified neurological disorder in a patient. Further provided are novel polynucleotides that can be used in the methods. Further provided are methods for isolating a variety of aberrant human glutamate transporter 2 nucleic acids. Additionally provided are screening methods for detecting compounds that can boost normal EAAT 2 polypeptide activity. Additionally provided are hybridization chips that can be used to facilitate detection of the neurological disorder.

In general, optimal practice of the present invention can be achieved by use of recognized manipulations. For example, techniques for isolating mRNA, methods for making and screening cDNA libraries, purifying and analyzing nucleic acids, methods for making recombinant vector DNA, cleaving DNA with restriction enzymes, ligating DNA, introducing DNA into host cells by stable or transient means, culturing the host cells, methods for isolating and purifying polypeptides and making antibodies are generally known in the field. See generally Sambrook et al., *Molecular Cloning* (2d ed. 1989), and Ausubel et al., *Current Protocols in Molecular Biology*, (1989) John Wiley & Sons, New York.

As discussed above, the invention features methods for detecting at least one type of aberrant EAAT 2 mRNA in a patient which methods are indicative of at least one specified neurological disorder in the patient. As also discussed, the aberrant EAAT 2 mRNAs of this invention fell into two broad classes: intron-retention EAAT 2 mRNA or an exon skipping EAAT 2 mRNA. Illustrative of each type of mRNA, shown at the level of cDNA, is provided in the drawings and examples, which follow. See e.g., FIGS. 2 A–B and 3–11.

In particular, an intron-retention EAAT 2 mRNA of this invention will include a normal (i.e., full-length) or modified EAAT 2 mRNA fused to at least a fragment of an EAAT 2 gene intron. In one embodiment, the intron-retention EAAT 2 mRNA includes a modified EAAT 2 mRNA fused to substantially all of the EAAT 2 gene intron or more than one intron up to about 2 or 3 of such introns. For example, the intron-retention EAAT 2 mRNA can include a modified EAAT 2 mRNA fused to about 1%, 2%, 5%, 10%, 20%, 30%, 50%, 60%, or 70%, up to about 80% or more of an EAAT 2 gene intron. In another example, the intron-retention EAAT 2 mRNA includes a modified EAAT 2 mRNA fused to substantially all of an EAAT 2 gene intron up to 100% of that intron.

As is known in this field, the normal EAAT 2 gene generally include introns between exons 1 and 2, exons 2 and 3, exons 3 and 4, exons 4 and 5, exons 5 and 6, exons 6 and 7, exons 7 and 8, exons 8 and 9, exons 9 and 10; and exons 10 and 11 of the normal EAAT 2 gene. Introns can be isolated by several techniques known in the field, e.g., hybridization techniques that detect repetitive intron sequences. The introns generally have a nucleotide length of between about 500 to about 5000 basepairs or more. An exemplary EAAT 2 gene intron is the intron between exons 7 and 8 of the EAAT 2 gene sequence (sometimes referred as intron 7). A preferred intron-retention EAAT 2 mRNA includes between about 1 to about 1000 and preferably about 1008 nucleotides of the intron 7 sequence. See FIGS. 13A and 13B below.

Reference herein to a "normal" EAAT 2 gene or related term is meant a wild-type EAAT 2 gene sequence (including normal allelic variants) that can be found in healthy donors with no apparent nervous system dysfunction. See, e.g., U.S. Pat. No. 5,658,782 which discloses the human EAAT 2 cDNA sequence, the disclosure of the which is specifically incorporated herein by reference. See also FIGS. 1 A–C and SEQ ID No. 1 for the sequence of the cDNA complement of normal EAAT 2 mRNA sequence.

By the term "modified EAAT 2 mRNA" is meant an EAAT 2 RNA sequence (sometimes referenced as a primary EAAT 2 transcript) which RNA sequence has been processed so that the processed RNA molecule lacks, either partially or fully, exon sequence found in the full-length EAAT 2 mRNA. Such processing is often referred to as RNA "splicing". For example, a modified EAAT 2 mRNA may lack at least about 2% to about 5%, at least about 10%, 20%, 30%, to 40%, 50%, 60% to about 80%, about 90% or about 95% or more of the exon sequence found in the normal EAAT 2 mRNA sequence.

It will be apparent from the preceding discussion that some modified EAAT 2 mRNAs will be exon skipping EAAT 2 mRNAs. By the term "exon skipping" is meant specifically incorrect RNA processing of the primary EAAT 2 RNA. That processing results in a modified EAAT 2 mRNA and particularly an exon-skipping EAAT 2 mRNA. For example, the exon skipping EAAT 2 mRNA may lack, either partially or fully, sequence encoded by at least one exon when compared to the full-length EAAT 2 mRNA. In particular, the exon skipping EAAT 2 mRNA may lack all or part of sequence encoded by exons 1, 2, 3, 4, 5, 6, 7, 8, 9, 10 or 11 of the EAAT 2 gene. The exon skipping EAAT 2 mRNA may lack all or part of sequence encoded by multiple exons, i.e. exons 2, 3, 4, 5, 6, 7, 8, 9, or 10. In some embodiments, the lack of sequence encoded by multiple exons may relate to a lack of contiguous or non-contiguous exons with respect to exon organization of the EAAT 2 gene. Illustrative of such exon skipping EAAT 2 mRNAs, shown at the cDNA level, are set forth below and in the drawings. See FIG. 13A for an exon map of the normal EAAT 2 cDNA.

By lack of at least part of an EAAT 2 exon is meant at least about 2%, 5%, 10%, 20%, 40%, or 50%, preferably at least about 70%, 80%, 90%, and more preferably at least about 95% up to 100% of the exon. See FIGS. 13A, 13B, and FIG. 12 for information relating to exon structure in the EAAT 2 gene.

As noted, neurological disorders of specific interest include those associated with abnormal release or removal of excitotoxic amino acids such as glutamate. Several CNS neuron types are especially adversely affected by excitotoxic glutamate. See e.g., Choi, D. W. (1988) *Neuron* 1: 623; and references cited therein. Specifically preferred neurological disorders include AD, HD, PD with ALS being especially preferred.

As noted, preferred use of the present invention involves detecting at least one specified neurological disorder in a subject, preferably a mammal, and more preferably a human patient. That patient may have or may be suspected of having (including having sometime in the future) the neurological disorder. Optimal practice of the invention generally requires obtaining a suitable biological sample. Preferred samples are obtained from a human patient although other samples can be obtained if needed. In particular, the biological sample can be obtained from a suitable cell line, tissue culture, or other source such as a tissue or organ which is known to contain detectable amounts of RNA, preferably mRNA and more preferably EAAT 2 mRNA (normal and/or aberrant). Some biological sources will include functional EAAT 2 polypeptide, e.g., as when the sample is obtained from an apparently healthy and non-affected donor. Methods for ascertaining apparently healthy and non-affected donors are known in the field.

Methods for detecting the EAAT 2 RNA or EAAT 2 polypeptide are known and include Northern blotting, Western blotting, and glutamate transport assays such as those specifically provided below. A preferred biological sample can be tissue obtained from the CNS, e.g., a biopsy taken from the brain. Preferred are those brain regions that are known to express EAAT 2 polypeptide as provided below. Additional biological samples can be obtained from fetal tissue if desired. Especially preferred biological samples include nervous system fluid and especially cerebrospinal fluid (CSF).

Reference herein to a "first biological sample" as typically obtained from a control subject is meant to describe a sample from an apparently healthy donor or other source that is known not to exhibit a specified neurological disorder. More specifically, the first sample will not include detectable levels of any aberrant EAAT 2 mRNA. Thus, the level of normal EAAT 2 mRNA and/or EAAT 2 polypeptide in selected first samples provides a useful baseline from which to make various comparisons. As will be fully appreciated, once levels of the normal EAAT 2 mRNA and/or polypeptide are established for any healthy donor or group of donors, it is usually not necessary to assay for the normal EAAT 2 mRNA and polypeptide for each assay. As noted, preferred samples will typically include detectable RNA, preferably mRNA and particularly EAAT 2 mRNA (normal and/or aberrant). By "detectable" is meant that the nucleic acid can be detected by any of the PCR methods, including preferred RT-PCR methods described herein.

Total cell RNA in a biological sample including mRNA can be purified for amplification by any of several methods if desired. Normal or aberrant EAAT 2 mRNA levels can be assayed using nearly any appropriate method known in the field including Northern analysis, single-stand nuclease mapping, particularly S1 nuclease mapping, PCR, reverse transcription in combination with PCR (RT-PCR), cloning, and reverse transcription in combination with a ligase chain reaction (RT-LCR). Additional methods include use of commercially available kits for isolating and purifying mRNA. See e.g., Chomczynski and Sacchi, *Anal. Biochem.* (1987) 162: 156 for one method of isolating RNA.

As noted, it is generally preferred to detect normal and aberrant EAAT 2 mRNA in a sample by amplification, preferably by PCR or a related method, more preferably by RT-PCR. Using RT-PCR, levels of intact and full-length EAAT 2 mRNA can be readily measured, as can levels of any aberrant EAAT 2 mRNAs present in the sample. See e.g., Makino et al. (1990) *Technique* 2: 295; *Polymerase Chain Reaction* (PCR): *The Technique and Its Applications* (1993) R. G. Landes Company for specific disclosure relating to the methods. See also the specific examples provided below.

The RT-PCR can be performed by one or a combination of different strategies. For example, one method involves adding RNA from a suitable biological fluid such as CSF in a reaction mixture including at least one oligonucleotide primer, typically referred to as an RT primer, and a suitable buffer. In some cases, it may be useful to add an aliquot of the CSF directly to the reaction mixture. After allowing a sufficient time for hybridization (annealing) of the RT primer to the RNA, the reaction can be supplemented with additional RT buffer, deoxynucleotide triphosphates (dNTPs), DTT, one or more RNAse inhibitors such as RNAsin, and an appropriate amount of reverse transcriptase. After incubation for a sufficient time to allow reverse transcription of the RNA, the RT products and then subjected to PCR using suitable oligonucleotide primers, e.g., a pair of such primers. The PCR primers can be detectably-labeled if desired or a detectable label can be added to the PCR reaction to follow the amplification of the reverse transcription template.

Methods for detectably-labeling nucleic acids are well known in the field and include use of certain radionuclides, stable radioisotopes, chromophores, fluorophores and the like.

The PCR amplification can be achieved by a variety of suitable methods including performing the reaction in a commercially available DNA thermal cycle. After a suitable number of rounds of amplification, the amplified PCR products, usually cDNA, are separated by molecular weight on an appropriate gel made, e.g., from polyacrylamide or agarose. If desired, the amounts of the amplification products can be measured by detecting the detectable label incorporated into the amplification products. In most cases, use of a commercially available imaging analyzer will be preferred. Various acceptable RT and PCR conditions and reagents are well known in the field. Specific RT-PCR reaction conditions are provided in the examples which follow. See e.g., Ausubel et al. supra; and Makino et al. supra.

Almost any pair of oligonucleotide primers that are capable of amplifying the EAAT 2 gene sequence (exons, introns, or exons and introns) are potentially useful for the purposes of this invention. Generally, a suitable oligonucleotide primer will be a DNA sequence of between about 12 to about 70 nucleotides in length preferably about 20, 30, 40, to about 50 or about 55 nucleotides in length. The oligonucleotide primers can suitably include restriction sites to add specific restriction enzyme cleavage sites to the PCR product as needed, e.g., to introduce a ligation site. Preferred DNA oligonucleotide primers are spaced from one another in opposing direction relative to extension of the primers. That is, the primers are spaced relative to each other on a polynucleotide template (usually on different strands) sufficient to produce an amplification product of at least about 50 nucleotides, at least about 60 to about 100 nucleotides, at least about 200 to 500 nucleotides, at least about 600 to 1000 nucleotides, or at least about 1000 to 2500 nucleotides as determined, e.g., by gel electrophoresis. Exemplary primers are provided in the examples and Drawings which follow.

Preferred methods of the invention include determining the DNA sequence of PCR amplified products which products will preferably include DNA sequence, typically cDNA sequence, which is preferably substantially homologous or identical to any one of the DNA sequences shown in SEQ ID NOS 3 & 5–13, respectively, in order of appearance (or the complement thereof).

By the term "substantially homologous" is meant relationship between two nucleic acid molecules and generally refers to subunit sequence similarity between the two molecules. Typically, the two nucleic acid molecules will be DNA. When a subunit position in both of the DNA molecules is occupied by the same monomeric subunit, i.e. a nucleotide, then they are homologous at that position. Homology between the two sequences is a direct function of the number of matching or homologous positions, egg., if 50% of the subunit positions in the two DNA sequences are homologous then the two sequences are 50% homologous. By "substantially homologous" is meant largely but not wholly homologous. More particularly, the term is meant to denote at least about 60%, 70%, 80%, 90%, 95% or greater homology up to about 99% homology with respect to any one of the DNA sequences illustrated in SEQ ID NOS 3 & 5–13, respectively, in order of appearance.

Two substantially homologous polynucleotides can be identified by one or a combination of different strategies. For example, in one approach, a polynucleotide of this invention that is substantially homologous to any one of the DNA sequences shown in SEQ ID NOS 3 & 5–13, respectively, in order of appearance (inclusive), in addition to fragments and derivatives thereof of a length sufficient to bind to the DNA sequences in SEQ ID NOS 3 & 5–13, respectively, in order of appearance (inclusive), can be identified by employing moderately stringent conditions (referred to herein as "normal stringency" conditions). In particular, normal stringency conditions are meant to include a hybridization buffer comprising 20% formamide in 0.8M saline/0.08M sodium citrate (SSC) buffer at a temperature of 37° C. and remaining bound when subject to washing once with that SSC buffer at 37° C. See e.g., Sambrook et al. supra. Additional methods include use of commercially available computer programs that can readily determine homology between nucleic acids of known or partially known sequence.

Nucleic acid fragments and derivatives of this invention preferably should comprise at least about 20 to about 50 nucleotides, at least about 60, 100 to 200 nucleotides, at least about 300, 400, to about 500 nucleotides, or at least about 1000, 1500, 2000 to about 2500 nucleotides. In some preferred embodiments, the nucleic acid fragment or derivative is bound to some moiety, which permits ready identification such as a radionucleotide, fluorescent or other chemical identifier.

As discussed, the invention provides methods for detecting at least one specified neurological disorder in a subject. For example, in one embodiment, the method includes obtaining a first biological sample from a control subject and a second biological sample from the patient, wherein the first and second samples each preferably comprise detectable mRNA. The method also includes contacting the first and second samples independently with at least two suitable oligonucleotide primers in which at least one primer, typically one of the primers, is capable of hybridizing to the DNA sequence shown in SEQ ID NO. 1, e.g., under normal stringency conditions. At least one other primer is capable of hybridizing to an EAAT 2 intron sequence under the same or related stringency conditions. It is generally preferred that the contacting be conducted under conditions capable of hybridizing each primer pair to the mRNA. The method further includes incubating any hybridized pair of oligonucleotide primers in the first and second samples under conditions capable of producing cDNA; and detecting in the second sample, any cDNA of between from about 25, 50, 100, 200, 300, 500, 600, 700, 900, 1000, 1500 to about 2200 or about 2500 nucleotides in length as being indicative of the neurological disorder in the patient.

The term "indicative of a neurological disorder" is used herein to mean that presence of at least one type of EAAT 2 mRNA is taken to be correlative with presence or risk of the disorder.

In preferred embodiments of the method, the neurological disorder is ALS, HD, PD or AD, and most preferably ALS. Particularly preferred is when at least one of the oligonucleotide primers is capable of hybridizing to the EAAT 2 gene intron 7 sequence under the normal hybridization conditions. Preferred primers are those capable of producing amplification products within the size ranges discussed above. Illustrative, are specific primers such as primer A (SEQ ID NO: 14) and primer B (SEQ ID NO: 15). See the examples and drawings below. Alternatively, suitable oligonucleotide primers can be substantially homologous to the primer A and/or primer B sequences.

Additionally provided is a method for detecting a neurological disorder in a subject such as a human patient in which the method includes obtaining a first biological sample from a control subject and a second biological sample from the patient in which each sample comprises mRNA. In one embodiment, the method includes contacting the first and second samples independently with at least a pair of oligonucleotide primers that are capable of hybridizing to the DNA sequence shown in SEQ ID No. 1. Typically, the contacting will be under conditions sufficient to hybridize the primers to the mRNA, such as the normal hybridization conditions described above. In a particular embodiment, the method includes extending the pair of oligonucleotide primers in each of the first and second samples under conditions sufficient to produce cDNA; and detecting in the second sample any cDNA having a smaller nucleotide length than cDNA in the first sample as being indicative of ALS in the patient. The nucleotide size differential, if present, can be readily detected by electrophoresis including polyacrylamide or agarose gel electrophoresis using appropriate molecular weight markers (e.g., a Hind III digest of bacteriophage λ).

In this embodiment of the method, it is preferred that the neurological disorder to be detected be ALS, HD, PD or AD, with ALS being particularly preferred. Additionally preferred are oligonucleotide primers which are capable of hybridizing to the normal EAAT 2 cDNA sequence set forth in SEQ ID No. 1, e.g., under normal or related hybridization conditions. Preferred primers are those capable of producing amplification products within the size ranges discussed above. Illustrative are primer A (SEQ ID NO: 14) and primer C (SEQ ID NO: 16) as set forth in the examples below. Alternatively, suitable oligonucleotide primers can be substantially homologous to the primer A and/or primer C sequences.

The term "complementary" or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99 to about 100%. Complementary polynucleotide sequences can be identified by a variety of approaches including use of well-known computer algorithms and software.

The present invention also features methods for detecting a neurological disorder in a subject such as a human patient which method involves isolating mRNA from a biological sample and contacting the mRNA in the sample with a nucleic acid comprising a polynucleotide sequence, preferably a DNA sequence, that is complementary to an intron or intron fragment from the normal EAAT 2 gene. The contacting will generally be under hybridization conditions capable of forming a specific binding complex between the mRNA and the nucleic acid. The method further includes detecting the binding complex as being indicative of the aberrant human glutamate transporter 2 (EAAT 2) mRNA in the sample.

In one embodiment, the method specifically includes treating the binding complex with a single-strand nuclease particularly S1 nuclease and identifying any hydrolyzed nucleic acid as being indicative of the aberrant human glutamate transporter 2 (EAAT 2) mRNA in the sample. In a particular embodiment, the intron sequence is from intron 7 of the EAAT 2 gene. See the examples, which follow for specific disclosure relating to use of S1 nuclease. See also Ausubel et al. supra; and Sambrook et al. supra.

By the term "specific binding" or similar term is meant a molecule disclosed herein which binds another molecule, thereby forming a specific binding pair, but which does not recognize and bind to other molecules as determined by, e.g., Western blotting, Northern or Southern blotting, ELISA, RIA, gel mobility shift assay, enzyme immunoassay, competitive assays, saturation assays or other suitable protein binding assays known in the field.

Further provided is a method of isolating an aberrant EAAT 2 cDNA. In one embodiment, the method includes obtaining a first biological sample from a control subject and a second biological sample from a patient in which the method includes producing cDNA in each of the first and second samples. In this embodiment, the cDNA comprises DNA sequence substantially homologous to SEQ ID NO. 1 and then introducing the cDNA from the first sample into control cells under conditions sufficient to express the cDNA in the control cells. Typically, introduction of the cDNA from the first sample and the second sample into test cells is performed under conditions sufficient to express the cDNA in the test cells. The method also includes detecting a reduction in glutamate transport in the test cells compared to the control cells as indicative of isolation of the aberrant human glutamate transporter 2 (EAAT 2) cDNA.

Additional methods for isolating the aberrant EAAT 2 cDNA include hybridization of cDNA libraries made from the sample with detectably-labeled probes to detect homologous or substantially homologous sequences.

The term "standard glutamate assay" or like term is meant to include one or more of the following steps:
a) making a first recombinant vector comprising DNA sequence encoding the normal EAAT 2 cDNA (SEQ ID NO. 1) or a suitable fragment thereof,
b) making a second recombinant vector comprising DNA sequence encoding an aberrant EAAT 2 cDNA of interest, e.g., the cDNA sequence illustrated in SEQ ID NO: 3,
c) introducing the first vector into a suitable cells such as COS-7 cells (control cells),
d) introducing the second vector into COS-7 cells or other suitable cells (test cells);
e) adding detectably-labeled glutamate; and
f) detecting glutamate transport in the control cells and any glutamate transport in the test cells.

As will be appreciated, the standard glutamate assay can be modified in several ways to suit intended use. For example, in instances where a baseline level of EAAT 2 gene or cDNA expression has been established in the control cells, it may not always be necessary to make the first recombinant vector or to introduce same into the control cells. In this embodiment, results from the test cells can be directly compared to the baseline level if desired.

Typically, the standard glutamate assay is a sodium-dependent glutamate transport assay. Introduction of the recombinant vectors in accord with the standard glutamate assay can be conducted by any acceptable means, e.g., retroviral transfer, viral or bacteriophage infection, calcium-, liposome-, DEAE or polybrene-mediated transfection, biolistic transfer, or other techniques known in the art. See Sambrook, et al. supra; Ausubel, et al. supra.

In one embodiment of the standard glutamate essay, the test and control cells are washed following introduction of the recombinant vectors and then incubated with a suitable amount of detectably-labeled glutamate, e.g., $^3$H-labeled glutamate (DuPont-NEN) and non-labeled glutamate. Following a suitable incubation interval, test and control cells are washed several times in a suitable wash buffer such as ice-cold PBS, solublized in a solution comprising about 0.1% SDS and the amount of radioactivity associated with the cells determined using conventional scintillation counting methods.

An especially preferred glutamate transport assay has been disclosed by Rothstein et al. (1995) *Ann. Neurol.* 38: 78. See also Rothstein et al. (1992) *N. Engl. J. Med.* 326: 1464. The disclosures of which are specifically incorporated by reference. See also the examples and drawings, which follow.

As noted, the present invention further provides polynucleotide sequences substantially homologous or identical to the DNA sequences represented in SEQ ID NOS 3 & 5–13, respectively, in order of appearance (inclusive) or the complement thereof. A complementary sequence may include an antisense polynucleotide which can be DNA, RNA, cDNA, cRNA genomic DNA or chimeras thereof. When the sequence is RNA, the deoyribonucleotides A, G, C, and T will be replaced by ribonucleotides A, G, C and U, respectively. Also included in the invention are fragments or derivatives of such sequences.

The polynucleotide sequences of the invention can be altered by mutations such as substitutions, additions or deletions that can provide for substantially homologous nucleic acid sequences. In particular, a given nucleotide sequence can be mutated in vitro or in vivo, to create variations in the nucleotides, e.g., to form new or additional restriction endonuclease sites or to destroy preexisting ones and thereby to facilitate further in vitro modification. Any technique for mutagenesis known in the art can be used including, but not limited to, in vitro site-directed mutagenesis (Hutchinson et al., *J. Biol. Chem.*, 253:6551 (1978)), use of TAB Registered TM linkers (Pharmacia), PCR-directed mutagenesis, and the like.

The isolated nucleotide sequences of the invention may be cloned or subcloned using any method known in the art. See e.g., Sambrook, J. et al., supra. In particular, nucleotide sequences of the invention may be cloned into any of a large variety of vectors. Possible vectors include, but are not limited to, cosmids, plasmids or modified viruses, although the vector system must be compatible with the host cell used. Viral vectors include, but are not limited to, lambda, simian virus, bovine papillomavirus, Epstein-Barr virus, and vaccinia virus. Viral vectors also include retroviral vectors, such as Amphatrophic Murine Retrovirus (see Miller et al., *Biotechniques*, 7:980–990 (1984)), incorporated herein by reference). Plasmids include, but are not limited to, pBR, pCMV5, PUC, pGEM (Promega), and Bluescript 9 (Stratagene) plasmid derivatives. Introduction into and expression in host cells is done for example by, transformation, transfection, infection, electroporation, etc. See the examples which follow for particularly preferred recombinant vectors.

For preferred production of anti-sense RNA, use of specified recombinant vectors typically including strong bacterial or eukaryotic (e.g., viral) promoters will usually be desired. See e.g., Ausubel et al. supra and the discussion which follows.

The term "vector" or "recombinant vector" as used herein means any nucleic acid sequence of interest capable of being incorporated into a host cell and resulting in the expression of a nucleic acid sequence of interest. Vectors can include, e.g., linear nucleic acid sequences, plasmids, cosmids, phagemids, and extrachromosomal DNA. Specifically, the vector can be a recombinant DNA. Also used herein, the term "expression" or "gene expression", is meant to refer to the production of the protein product of the nucleic acid sequence of interest, including transcription of the DNA and translation of the RNA transcript. Most recombinant vectors will include a "cloning site" which as used herein is intended to encompass at least one restriction endonuclease site. Typically, multiple different restriction endonuclease sites (e.g., a polylinker) are contained within the vector to facilitate cloning.

Exemplary host cells which can express the isolated nucleic acids of this invention include bacterial cells (e.g., *E. coli*) such as MM294, DM52, XL1-blue (Stratagene) strains of *E. coli*, and animal cells (e.g., CV-1 and COS-7 cells). In addition, it is possible to express certain isolated nucleic acids of the invention in certain yeast cells (e.g., *S. cerevisiae*), amphibian cells (e.g., *Xenopus oocyte*), and insect cells (e.g., *Spodoptera frugiperda* and *Trichoplusia ni*). Methods for expressing isolated and recombinant DNA in these cells are known. See e.g., Sambrook et al., *Molecular Cloning* (2d ed. 1989), Ausubel et al. supra, and Summer and Smith, A Manual of Methods for Baculovirus Vectors and Insect Cell Culture Procedures: Texas *Agricultural Experimental Station Bulletin* No. 1555, College Station Texas (1988).

A "polypeptide" refers to any polymer consisting essentially of any of the 20 amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted.

As will be described in more detail by the examples and discussion which follows, in most cases, aberrant EAAT 2 mRNA of this invention will give rise to negligible or undetectable levels of polypeptide. However, where significant levels of polypeptide can be deleted, e.g., as when other host cells conducive to polypeptide production or stability are used, conventional immunological methods can be used to raise antibodies, preferably monoclonal antibodies, against the polypeptides. The polypeptides can be detected by a variety of means including western blots using anti-EAAT 2 antibodies.

Additional antibodies of interest will be those directed against specified oligopeptide sequences. The oligopeptides will generally be amino acid sequence spanning a deletion site in an aberrant EAAT 2 mRNA sequence, i.e. The abnormal splice site. The oligopeptide sequences can be make synthetically by techniques well known in the field. Methods for making oligopeptide sequences and antibodies have been disclosed in Ausubel et al. supra and Harlow and Lane in, *Antibodies: A Laboratory Manual* (1988).

A further embodiment of the present invention provides methods for screening a biological sample for at least one specified neurological disorder. More particularly, the method can be used as a diagnostic aid to screen the biological sample. Diagnostic aids and methods for using the diagnostic aids are particularly useful when it is desirable to screen the biological sample for presence of a at least one aberrant EAAT 2 mRNA. Such an approach would be especially useful for the detection of the aberrant EAAT 2 mRNAs in particular patients having or suspected of having at least one specified neurological disorder. Additionally useful is detection among families of patients, e.g., to analyze incidence of phenotypic, genotypic (allelic), or somatic EAAT 2 gene variation.

In a particular embodiment, the diagnostic aids include specific polynucleotides of this invention that have been fixed (i.e. preferably covalently attached) to a solid support which support is typically contacted with the biological sample (or more than one of such samples). The polynucleotide can be fixed directly to the support or indirectly through a suitable linker as needed. Detection of hybridization (if present) between at least one target nucleic acid in the sample and at least one fixed polynucleotide on the support is taken to be indicative of at least one neurological disorder in the patient from which the sample was obtained. It will be appreciated that in many cases the target nucleic acid will be RNA and particularly mRNA although in some cases the target can be cDNA.

In most cases, the specified polynucleotides will be DNA typically of a length of between at least about 5 nucleotides to about 20 nucleotides, preferably at least about 10 to about 25 to about 30 nucleotides in length. However, certain sold supports are known to be compatible with larger DNA molecules, e.g., at least about 35 nucleotides, up to about 40, 45, 50, 60, up to about 100 nucleotides, at least about 200 nucleotides up to about 300, 400, 500, 600, 700, up to about 1000, 2000 to about 2500 nucleotides or more if desired. The polynucleotides can be suitably single- or double-stranded according to intended use. The polynucleotides can be made by any acceptable means including synthetic, recombinant, or semi-synthetic approaches known in the field.

In one embodiment, the specified polynucleotide is single-stranded DNA that is complementary to sequence of an aberrant EAAT 2 mRNA which sequence is not present in the normal EAAT 2 mRNA. For example, in one embodiment, the diagnostic aid can include a single-stranded DNA bound to a suitable solid support in which the DNA consists of intronic sequence from the EAAT 2 gene. In a particular embodiment, the single-stranded DNA consists of sequence from intron 7. Illustrations of such a DNA molecule is primer B (SEQ ID NO: 15). In another embodiment, the single-stranded DNA includes sequence complementary to a novel RNA splice site sequence that is present in the EAAT 2 mRNA but not the normal EAAT 2 mRNA. The examples and drawings which follow provide illustrative RNA splice site sequences, shown at the level of cDNA, that can be used to make suitable single-stranded DNA oligonucleotides. See e.g. FIGS. 2 A–B, 3–11, 13A and 13B.

In another embodiment, the specified polynucleotide is a DNA sequence substantially homologous to any one of the sequences shown in FIGS. 2 A–B, 3–11, 13A and 13B. (SEQ ID NOS 3 & 5–13, respectively in order of appearance (inclusive)).

As noted, the diagnostic aid includes a solid support that is capable of covalently binding directly and indirectly a specific polynucleotide which can be a suitable single-stranded nucleic acid as described above. Preferred are solid supports including or consisting of a plastic, ceramic, metal, resin, gel, or a membrane. A more preferred example includes a two-dimensional, or three-dimensional matrix, such as a gel, with potential multiple binding sites for the specified polynucleotide. Thus, in one embodiment, the solid support includes a plurality of a single type of bound polynucleotide as described. In this embodiment, the solid support has capacity to recognize (i.e. hybridize) one type of target if present in the sample. In another embodiment, the solid support includes at least two types of bound polynucleotide (e.g., (SEQ ID NOS 3 & 5–13, respectively, in order of appearance) different polynucleotides). In this specific embodiment, the solid support has capacity to bind (SEQ ID NOS 3 & 5–13, respectively, in order of appearance) different targets, respectively, in the sample.

An especially preferred solid support for binding at least one specified polynucleotide of this invention is a hybridization chip. See e.g., Pevzner et al., (1991) *J. Biomol. Struc. & Dyn.* 9: 399; Maskos and Southern (1992) *Nucl. Acids. Res.* 20: 1679; Johnston, M (1998) *Current Biology* 8: R171; and U.S. Pat. Nos. 5,631,134 and 5,556,752 to Cantor and Lockhart et al., respectively, for methods of making and using hybridization chips comprising a desired nucleic acid.

An illustrative hybridization chip uses at least one type of cDNA printed on a glass surface so that the chip can provide a high-density hybridization target. The chip can be contacted with a detectably-labeled mixture of mRNA obtained from a biological sample of interest. Detection schemes can be employed to provide rapid and simultaneous expression analysis of independent biological samples. See e.g., Schena M. *Bioessays* (1996) 18: 427; and Schena M. et al. (1995) *Science* 270: 467.

More particularly, hybridization chips can be used with one or more than one type of polynucleotide of this invention. When the hybridization chip is contacted with a desired biological sample any hybridization therein can be analyzed by one or a combination of different approaches. For example, the target nucleic acids can be detectably-labeled with any suitable label as described herein including a radioisotope, a stable isotope, an enzyme, a fluorescent molecule, a luminescent molecule, a chromophore, metal, electric charge, or a detectable structure such as an epitope. Methods for detectably labeling the target nucleic acids are generally known in the field. The label may be directly or indirectly detected using scintillation counting, an imaging implementation, or mass spectrometry. Preferred methods of detection include use of wave detection of surface plasmon resonance of thin metal film labels such as gold, by, e.g., BIAcore sensor (Pharmacia) or other suitable biosensors.

An especially preferred embodiment is a hybridization "micro-chip" comprising one or more than one specified polynucleotide of this invention. Such a chip will be particularly useful, e.g., in detecting at least one type of aberrant EAAT 2 mRNAs in CSF obtained from a patient. Hybridization, if present, can be detected by BIAcore or other suitable method.

Further provided by the present invention are methods for screening compounds useful in the diagnosis or treatment of a neurological disorder of interest, preferably ALS. In general, the compounds will be candidate compounds that will be selected for capacity to modulate expression of the normal EAAT 2 gene in suitable host cells or tissue particularly in the presence of at least one type of aberrant EAAT 2 mRNA or cDNA. Preferred compounds will increase the expression by at least about 10%, at least about 20% to about 30%, at least about 50% to about 70%, at least about 80% to 95%, and at least about 100% or more when compared to a suitable control assay without addition of the compound. In preferred embodiments, suitable cells such as Cos-7 cells are co-transformed with a recombinant vector including a normal and an aberrant EAAT 2 cDNA. The transformed cells are then contacted with the compound, and the effect of the compound, if any, on expression of the normal cDNA is determined, e.g., by Northern hybridization or by the standard glutamate transport assay discussed above. Of particular interest are agonists of the normal EAAT 2 cDNA expression.

Further provided by the invention is a method of treating or preventing a neurological disorder in a patient, the method comprising administering a therapeutically effective amount of a suitable recombinant vector capable of expressing an anti-sense nucleic acid, e.g., antisense RNA, which is capable of specifically binding at least one type of aberrant EAAT 2 mRNA.

The recombinant vector can be administered to a patient in need of treatment by one or a combination of strategies. For example, in one embodiment, the method includes administering to the patient at least one of the recombinant vectors in a form that permits entry of the construct into patient cell or groups of cells including tissues or organs. Preferred cells are those in the nervous system such as neurons, glia, and astrocytes. The administration may be carried out by any of various techniques known, for example, in the art of gene therapy. (see e.g., J. W. Larrick and Kathy L. Burck, (1991) *Gene Therapy, Application of Molecular Biology*, (Elsevier, Holland). In another embodiment, at least one of the recombinant vectors is administered by use of liposomes, e.g., immunoliposomes, according to techniques known in the field. Use of immunoliposomes has several advantages including the capacity to target contents to a desired cell or tissue type. Alternatively, the recombinant vector may be delivered via injection to a desired site including continuous injection via a shunt. Although not always optimal, delivery by way of mucosally-lined passages; or via the airways, for example; may be useful in some instances. See e.g., U.S. Pat. No. 5,624,803 to Noonberg et al. and references cited therein for compositions and methods for delivering of antisense oligonucleotides into desired cells.

Preferred in some instances is viral integration of at least one of the recombinant vectors into the chromosome of a desired cell. In this embodiment, it is possible to confer permanence or semi-permanence to expression of the recombinant vector in the cell or tissue of interest.

As noted, the invention can also be used to evaluate the efficacy of a therapy employed to treat a neurological disorder in a patient. In one embodiment, the disorder is ALS. In this embodiment, treatment of the ALS patient includes or consists of treatment with Rilutek™ (riluzole), a benzothiazole used to treat ALS. In this embodiment, an increase in normal EAAT 2 protein or mRNA in the patient will be taken as indicative of a beneficial effect of the drug in the patient. Although nearly any increase in the levels of normal EAAT 2 protein or mRNA will be considered beneficial to the patient, an increase of normal EAAT 2 protein or mRNA in the range of about 1.5 to about 10 fold or more relative to a suitable control will be especially desirable. It will be appreciated that the increase observed will depend on several factors as the age, sex and general health of the patient. A suitable control will include testing the patient prior to administration of the drug. The increase in normal EAAT 2 protein or mRNA can be evaluated by a variety of methods including measuring the increase relative to incidence of at least one type of aberrant EAAT 2 mRNA in the patient. It is preferred that the method be performed on CSF although other biological samples can be used if desired. The increase in normal EAAT 2 protein can be determined by assays disclosed herein (e.g., Western blots, Northern blots or PCR). Rilutek™ is available from Rhone-Poulenc Rorer Pharmaceuticals Inc. Collegeville, Pa. 19426-0107. See also the Physicians' Desk Reference (1998) (Medical Economics Company, Inc., Montvale, N.J.) pages 2380–2883 for therapies employing Rilutek™.

As noted, the invention also provides a kit for detecting at least one specified neurological disorder in a patient. In a preferred embodiment, the kit includes at least one container means. The container means includes a system for detecting the neurological disorder in the patient, wherein the system comprises at least one of: 1) at least a pair of oligonucleotide primers capable of specifically binding to any one of the DNA sequences of SEQ ID NOS 3 & 5–13, respectively, in order of appearance or the complement thereof; 2) an antibody capable of specifically binding a polypeptide encoded by an aberrant human glutamate 2 (EAAT 2) mRNA; 3) a hybridization chip comprising at least one isolated nucleic acid substantially homologous or identical to any one of the DNA sequences of SEQ ID NOS 3 & 5–13, respectively, in order of appearance or the complement thereof; and 4) a polynucleotide sequence comprising sequence substantially homologous or identical to any of the DNA sequences of SEQ ID NOS 3 & 5–13, respectively, in order of appearance (inclusive) or the complement thereof.

Additionally provided is a kit to treat a neurological disorder in the patient, which kit includes at least one container means including a recombinant vector capable of producing an anti-sense nucleic acid substantially homologous or identical to any of the DNA sequences of SEQ ID NOS 3 & 5–13, respectively in order of appearance or the complement thereof. In one embodiment, the anti-sense nucleic acid is RNA. Components of the kit can be used alone or with other therapeutic compounds as needed.

A kit of this invention may include additional components, as needed, including suitable buffers, indicators (e.g., fluorophores, chromophores or enzymes providing same), controls (e.g., a suitable polynucleotide of this invention) and directions for using the kit. Kit components can be provided in nearly any acceptable form, including a liquid or solid, e.g, as a lyophilized powder.

Further provided is cDNA library comprising sequence substantially homologous to the DNA sequence of any one of SEQ ID NOS 3 & 5–13, respectively, in order of appearance or the complement thereof.

Polynucleotides of this invention are typically isolated, meaning that the polynucleotides usually constitute at least about 0.5%, preferably at least about 2%, and more preferably at least about 5% by weight of total polynucleotide present in a given fraction. A partially pure polynucleotide constitutes at least about 10%, preferably at least about 30%, and more preferably at least about 60% by weight of total nucleic acid present in a given fraction. A pure polynucleotide constitutes at least about 80%, preferably at least about 90%, and more preferably at least about 95% by weight of total polynucleotide present in a given fraction. Purity can be determined by standard methods including gel electrophoresis.

It is preferred that the polypeptides of the present invention be substantially pure. That is, the polypeptides have been isolated from cell substituents that naturally accompany it so that the polypeptides are present preferably in at least 80% or 90% to 95% homogeneity (w/w). Polypeptides having at least 98 to 99% homogeneity (w/w) are most preferred for many pharmaceutical, clinical and research applications. Once substantially purified the polypeptide should be substantially free of contaminants for therapeutic applications. Once purified partially or to substantial purity, the polypeptides can be used therapeutically, or in performing a desired assay. Substantial purity can be determined by a variety of standard techniques such as chromatography and gel electrophoresis.

The following are non-limiting examples of the present invention.

EXAMPLE 1

Identification of Aberrant EAAT 2 Transcripts in ALS Affected Areas 1. cDNA from Patient Motor Cortex A male ALS patient (66 years old, 5 hr postmortem delay), without SOD1 mutations, was initially investigated. This patient was chosen because immunoblot studies revealed extremely low levels of EAAT 2 protein (5% of control) in motor cortex (Rothstein et al. (1995) *Ann. Neurol.* 38, 73). The Northern blotting revealed that the quantity and size of EAAT 2 mRNA were normal (Bristol, L. A., and Rothstein, J. D. (1996) *Ann. Neurol.* 39, 676). To investigate whether there were aberrant EAAT 2 mRNA species, a cDNA library was constructed from a poly (A)+ mRNA prepared from the motor cortex of this patient. The cDNA library was then screened and an abnormal cDNA clone was subsequently identified from positive clones by restriction analysis. Sequencing of this clone revealed that it contained 1091 bp of the EAAT 2 coding region from exon 1 to exon 7, followed by 1008 bp of intron region, corresponding to partial sequence of intron 7, ending with a poly A tail (Aoki et al. (1998) *Ann. Neurol.* 43, In press) (FIG. 13 A). A stop codon was found immediately after this exon and intron junction. Thus, the presumed translation product would be EAAT 2 protein truncated after codon 364.

FIG. 13 A is a schematic presentation of abnormally processed partial intron 7-retention and exon 9-skipping species in relation to the normal EAAT 2 gene. Probe E corresponds to position 1687 to 2210 from the 5' translation region. Probe F corresponds to position 537 to 1008 from exon 7 intron junction.

To ensure that it was not a cloning artifact, reverse-transcription polymerase chain reaction (RT-PCR) with the use of a primer pair that included normal exon and intronic sequences (FIG. 13 A, primer A and B), was performed on equal amounts of poly (A)+ mRNA (DNase I treated) prepared from motor cortex of the ALS patient and normal controls. As shown in FIG. 14A (at intron-retention EAAT 2; ALS patient 3), a strong signal was observed in the ALS specimen, but not in the control specimens.

Figure 14C:
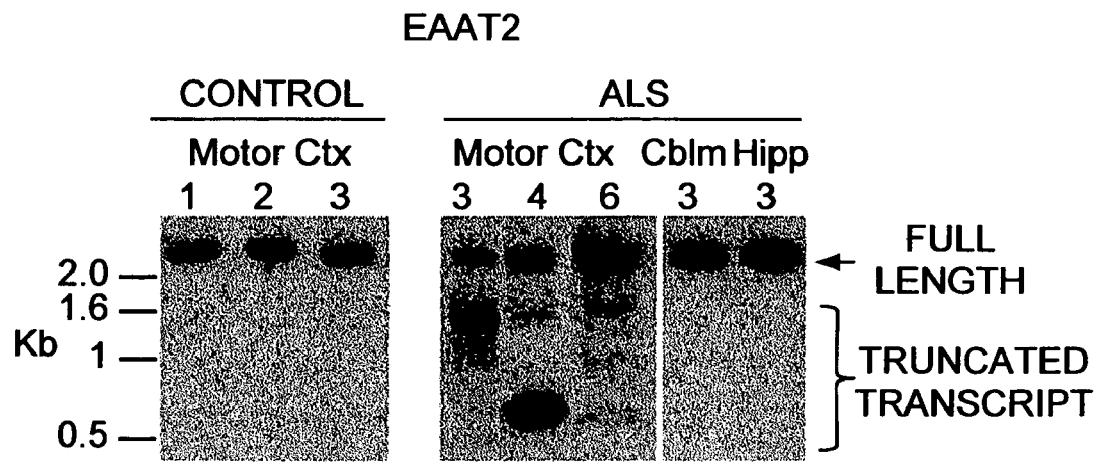
FIG. 14C is a representation of a Southern blot of RT-PCR reactions. The blot shows truncated EAAT 2 transcripts in ALS but not control motor cortex. Lanes numbers are identical to patients labeled in FIG. 1A.
Figure 14D:
FIG. 14D is a representation of a Southern Blot of RT-PCR reactions. The blots show no aberrant EAAT1 or SMN transcripts were found in ALS motor cortex. Lanes numbers are identical to patients labeled in FIG. 13A.

FIG. 14 A shows analysis of EAAT 2 protein (Western blot) and aberrant EAAT 2 mRNA species (RT-PCR/Southern blot) in ALS and control motor cortex. Aliquots of tissue homogenates from control or ALS motor cortex were subjected to SDS-polyacrylamide gel electrophoresis and immunoblotted with affinity-purified polyclonal carboxy-terminal antibody to EAAT 2. Controls included non-neurological and neurodegenerative disease specimens. Individual lanes are numbered for each patient. RT-PCR was performed on parallel tissue samples from each control or ALS motor cortex specimen. An internal control was designed for comparative analysis of the partial intron 7-retention mRNA between samples.

2. cDNA from Spinal Cord and Motor Cortex (Patient and Control)

As another approach, RT-PCR was used to amplify EAAT 2 cDNA fragments from poly (A)+ mRNA prepared from the spinal cord or motor cortex of the patient and from normal controls. A shorter PCR fragment was subsequently identified, using primer A and C (FIG. 13 A), which was amplified along with the normal size PCR fragment in the patient, but was not present in normal controls (FIG. 14 A; at exon 9-skipping EAAT 2, ALS patient 2). The shorter PCR fragment was cloned. DNA sequencing revealed it to be a 135 bp in-frame deletion in which exon 8 is linked directly to exon 10, demonstrating that it arises from skipping of exon 9 (Aoki et al., 1998 supra) (FIG. 13 A).

Furthermore, when primers D and C (FIG. 13 A) were used to amplify the full length EAAT 2 coding region, a large amount of shorter PCR fragments were observed in motor cortex of ALS, but not in normal controls (FIG. 14 C). All the shorter PCR fragments from ALS patient #3 (FIG. 14 C) were then cloned. Twenty clones were randomly selected and analyzed by restriction digestion. All of the these clones were found to have different internal deletions. In addition, a single band from the gel (Patient 3, FIG. 14 C) was cloned and was found to consist of multiple internally deleted cDNA, all similar in size. These results indicate that there are many different truncated EAAT 2 transcripts in ALS motor cortex.

Eight of the truncated cDNAs were then sequenced at the junction of the deletion regions (FIG. 13 B). Two cDNAs were found to be truncated due to exon-skipping (FIGS. 13 B₇ and 13 B₈). One cDNA was truncated at the appropriate splicing donor and acceptor sites (FIG. 13 B₅). Other truncated cDNAs were identified, although the deletions did not occur at common splicing sites (FIGS. 13 B₁₋₄, 13 B₆). The presence of multiple precise exon-skipping deletions (FIGS. 13 A and 13 B) suggest that it is very unlikely that they could be caused by somatic DNA deletions. The abundance of multiple truncated transcripts may be the result of aberrant RNA splicing.

3. Defect Specificity by Brain Region and Transporter Subtype

To examine the specificity of these defects for brain region and transporter subtypes, ALS and control tissue from several brain regions in the same patient was examined. As shown in FIG. 14 C, multiple truncated EAAT 2 mRNAs were found in ALS motor cortex, but not cerebellum or hippocampus from the same patient (3). Similar results were obtained every ALS patient examined (n=20). Other cell specific and general cellular mRNA species were examined. Truncated transcripts were not found for the astroglial glutamate transporter EAAT1 (FIG. 14 D), the neuronal protein EAAT3, or the constitutive spliceosomal assembly protein, survival motor neuron (SMN) (Fischer et al. (1997) *Cell* 90, 1023; Liu et al. (1997). *Cell* 90, 1013). (FIG. 14 D). EAAT1 and EAAT3 protein levels were previously shown to be normal in ALS (Rothstein et al., 1995 supra).

Thus, the results indicate that these aberrant RNA species were specific for ALS and were not an artifact. They were not observed in a small sample of other neurodegenerative disorders—Huntington's disease, Alzheimer's disease, and spinal muscular atrophy; they were found only in ALS neuropathologically affected brain regions, while unaffected brain regions in the same patients had normal EAAT 2 RNA; other transporter proteins, and constitutive RNA species were not affected. See Example 9 below.

3. Tissue and Cerebrospinal Fluid Specimens

ALS brain and spinal cord tissue was obtained from the Johns Hopkins ALS Brain Bank and the Alzheimer's Disease Research Center Brain Bank, with institution-approved informed consent. Post-mortem delays for autopsy were generally less than 12 hr. ALS and some control tissue was rapidly dissected; dissected regions were rapidly frozen (isopentane/dry ice), and then stored at −75° C. until use. Additional specimens were fixed in 4% paraformaldehyde. Pathological confirmation of ALS was made on all specimens by standard histological evaluation of spinal cord and motor cortex, with use of hematoxylin and eosin to evaluate motor neuron loss, and with myelin stains (Luxol-fast blue) to establish corticospinal tract degeneration. SOD1 mutation analysis was performed. Pathologically confirmed Alzheimer's disease and Huntington's disease brain tissue was provided by the Johns Hopkins Alzheimer's Disease Research Center Brain Bank. SMA spinal tissue was obtained at autopsy from patients diagnosed. Cerebrospinal fluid was obtained at the time of diagnostic evaluation for ALS and control patients with institution-approved informed consent. CSF was rapidly frozen and stored at −20 to −70° C. for up to 6 years.

The clinical diagnosis of ALS was made by the El Escorial criteria (Brooks, (1994) *J. Neurol. Sci.* 124 (suppl.) 96, including the presence of both upper and lower motor neuron signs, a definite history of progression, absence of sensory abnormalities, normal nerve conduction velocities and late responses, and electromyographic evidence of diffuse enervation. Patients typically were initially classified as having either probable or definite ALS based on these criteria. Patients were excluded if they had unexplained bowel or bladder changes, anatomic, metabolic, or toxic disorders that could mimic ALS, e.g. endocrine abnormalities, hexosaminidase A deficiency, lead intoxication, myelopathy, or peripheral neuropathy.

4. Methods

Poly (A) mRNA was isolated by using the FastTrack 2.0 mRNA isolation kit (Invitrogen). cDNA was synthesized from the isolated mRNA by using ZAP express cDNA synthesis kit (Stratagene). The cDNA was size-fractionated into three fractions, >6 kb, 3–6 kb, and <3 kb, by Sephacryl S-500 spin column. Each cDNA fraction was ligated into the ZAP express vector arms and packaged into Gigapack III Gold packing extract (Stratagene). The cDNA library was subsequently screened by a DNA probe prepared from full length EAAT 2 cDNA by random priming. The positive clones in the pBK-CMV phagemid were obtained after in vivo excision from the ZAP express vector with ExAssist helper phage.

Poly (A) mRNA was isolated from 50–100 mg of specimens (motor cortex, frontal cortex, hippocampus, caudate, cerebellum, lumbar or cervical spinal cord) by using Micro-Fast Track Kit (Invitrogen). The isolated mRNA was treated with DNase I for 20 min, heated to 65° C. for 5 min, and then reverse transcribed into cDNA. A 25 µl reverse transcription reaction mixture containing 50 mg of RNA, 1 mm dithiothreitol, 0.5 mM dNTPs, 20 units of RNasin, 200 units of M-MLV reverse transcriptase (BRL), 1× buffer, 0.5 µM primer (primer B for the intron-retention and primer C for the exon 9-skipping and the full length cDNA) was incubated at 42° C. for 60 min, heated to 65° C. for 5 min, and quick-chilled on ice. PCR was performed at a final concentration of 1×PCR buffer/0.2 mM dNTPs/0.5 µM each 5' and 3' primers (primer A and B for the intron-retention; primer A and C for the exon 9-skipping; primer D and C for the full length; FIGS. 13 A, 13B)/2 units of Taq polymerase (Boehringer Mannheim)/2.5 µl of reverse transcription reaction mixture in a total volume of 50 µl. The mixture was overlaid with mineral oil and then amplified with the Delta cycler II thermal cycler (Ericomp) for 25 or 30 cycles. The amplification profile involved denaturation at 94° C. for 30 sec, primer annealing at 55° C. for 30 sec, and extension at 72° C. for 1 min. PCR products (10 µl) were resolved by 1.2% agarose gel electrophoresis and transferred to membrane. The blot was probed with a ³²P-labeled EAAT 2 cDNA probe prepared by the random priming method (FIGS. 14 A and 18A, 18B) or a ³²P-end labeled oligonucleotide probe (FIGS. 14B, 14C, 16A and 16C) and then subjected to autoradiography. The same RT-PCR conditions were used to analyze EAAT1 mRNA.

To screen for intron-retention mRNA, a plasmid (pE2F) was constructed for use as an internal control for the comparative analysis of the intron-retention mRNA between patients. A 185 bp DNA fragment with Hind III on both ends was inserted into the intronic mutant cDNA at a Hind III site (indicated in FIG. 13A, triangle). This plasmid, pE2F, was used as a template for transcription by the T3 polymerase. The resulting pE2F complementary RNA (cRNA) product was purified by oligo (dT) chromatography. 50 mg of mRNA isolated from human tissue and 5 pg. of cRNA were combined and then reverse transcribed into cDNA by using primer B (FIG. 13A). The cDNA mixture was then amplified for 25 cycles. Under these conditions, the reaction rates of pE2F cRNA and intron-retention mRNA were identical within an exponential phase of the PCR reaction. Because the exon-skipping mRNA was 135 bp shorter than the wild-type EAAT 2 mRNA, the wild type EAAT 2 mRNA was used as an internal control for the comparative analysis of the exon-skipping mRNA between patients. Using the internal controls as standards, the relative amounts of intron-retention and exon 9-skipping mRNA were calculated and compared, between patient samples, by densitometric analysis of Southern blots.

For CSF studies, 400 μl CSF was centrifuged (1500×g) for 10 min to pellet blood cell debris. Total RNA was isolated from the supernatant using QIAamp kit (Qiagen). Poly (A) mRNA was further isolated and subjected to RT-PCR procedures as described above. EAAT 2 is only expressed by CNS tissue. No wild-type or exon 9-skipping EAAT 2 mRNA was detected from the pelleted blood cell debris.

PCR products were isolated from agarose gel by using QIAquick Gel Extraction Kit (Qiagen). They were then cloned into pCR 2.1 vector (TA cloning Kit, Invitrogen). Plasmid DNA were isolated from transformed cells by using PERFECT prep Plasmid DNA kit (5 prime 3 prime, Inc). Sequencing of the DNA was carried out on an Automated DNA Sequencer (Applied Biosystem).

Primers used for RT-PCR of EAAT 2 were as follows: Primer A (5'-GGCAACTGGGGATGTACA-3' SEQ ID NO: 14) corresponding to position 933 from 5' translation region; Primer B (5'-CCAGAAGGCTCAAGAAGT-3' SEQ ID NO: 15) corresponding to position 170 from exon 7-intron junction; Primer C (5'-ACGCTGGGGAGTTTATTCAAGAAT-3' SEQ ID NO: 16) corresponding to position 1768 from the 5' translation region; Primer D (5'-ACCGTCCTCTGCCAC-CACTCT-3' SEQ ID NO: 17) corresponding to position −428. Primers used for RT-PCR of EAAT1 were as follows: 5'-AGGAGGTTTGGCTTTCTGTGG-3' (SEQ ID NO: 18) corresponding to position -73; 5'-GGTTTTTAACACCTG-GTGCTCAA-3' (SEQ ID NO: 19 corresponding to position 1655 from the 5' translation region. Oligonucleotides used for preparing probe were as follows: 5'-CGGCTGACTTTC-CATTGGCTG-3' (SEQ ID NO: 20) corresponding to position 1664 from the 5' translation region of EAAT 2; 5'-CCTGGTGCTCAAGAAAGTGTTTC-3' (SEQ ID NO: 21) corresponding to position 1664 from the 5' translation region of EAAT 1.

EXAMPLE 2

Aberrant EAAT 2 Transcripts are Present In Vivo

Figure 15D:
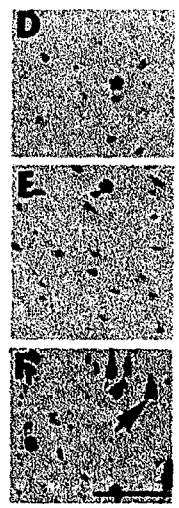
Figure 15E:
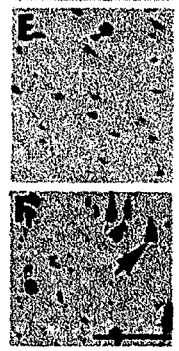

To verify that the aberrant EAAT 2 transcripts of Example 1 were present in vivo and not a cloning or PCR artifact, in situ hybridization was performed to detect partial intron 7-retention mRNA using a riboprobe to the intronic region (FIG. 13A, probe F). FIGS. 15A and 3B show that this partial intron 7-retention mRNA was present only in ALS motor cortex, but not in control specimens, in agreement with the RT-PCR results. In addition, signals were uniformly localized to small cells, presumably astrocytes, present throughout the motor cortex (EAAT 2 is an astrocyte-specific protein) (FIG. 15D; asterisk). As a control, signals for actin (FIGS. 15C and F) were found expressed by both neurons (arrowhead) and astroglia. Wild-type EAAT 2 mRNA in ALS (FIG. 15E) and in control tissue were expressed in a distribution similar to the partial intron 7-retention mRNA. No staining was seen with sense controls. Furthermore, the dramatic loss of EAAT 2 protein (Rothstein et al., 1995 supra) (FIGS. 15 G and 15H) in ALS motor cortex appears to be associated with the presence of the partial intron 7-retention transcripts, which was specific to ALS and was not detected in motor cortex from control specimens (FIG. 15B), or in specimens of motor cortex from ALS patients that were not RT-PCR positive for the intron-retention transcripts.

In FIGS. 15A to 15H, the partial intron 7-retention mRNA was localized to small cells throughout the motor cortex in ALS (FIG. 15A), but was not detected in control motor cortex (FIG. 15B). When compared to mRNA for the general cellular protein actin (FIG. 15C), the localization appeared to be consistent with astrocytes. Higher power analysis (FIGS. 15D, 15E and 15F) of ALS motor cortex confirmed that aberrant partial intron 7-retention mRNA was localized to small cortical cells (asterisk, FIG. 15D), identical to the localization of wild-type EAAT 2 mRNA in ALS cortical astrocytes (FIG. 15E), whereas actin was localized in both astrocytes and neurons (FIG. 15F, arrow) in ALS motor cortex. The localization of the partial intron 7-retention EAAT 2 mRNA (FIG. 15A) correlated with the decreased expression of EAAT 2 protein (FIG. 15G) in ALS compared with expression of EAAT 2 protein in control motor (FIG. 15H) cortex.

In situ hybridization was performed with digoxigenin-UTP labeled RNA probes generated from 1 μg of DNA template using the Maxiscript In vitro transcription kit (Ambion, Calif.). The probes for detecting wild-type EAAT 2 mRNA and the partial intron 7-retention mRNA are indicated in FIG. 13A as probes E and F, respectively. Specificity controls included sense RNA probes and pre-treatment of tissue with RNase A (10 μg/ml) in 2×SSC at 37° C. for 30 min. An actin control provided with the kit contained ~250 bp of β-actin fragment in the antisense orientation. Frozen tissue was sectioned (8 μm), fixed with 4% paraformaldehyde in 0.1 M phosphate buffered saline (PBS; pH 7.4), rinsed with PBS, treated with 0.2% Triton X-100, rinsed again with PBS, followed by proteinase K (1 μg/m) in TE buffer (100 mM Tris-HCl, 50 mM EDTA, pH 8.0) at 37° C. for 30 min, then 0.1 M glycine in PBS, and again with 4% paraformaldehyde in PBS. The sections were acetylated with 0.25% acetic anhydride in TE with 0.1 triethanolamine, rinsed with DEPC water, air dried, then hybridized overnight with probe (2 μg/ml) in hybridization buffer (50% deionized foramide, 5×SSC, 10% dextran sulfate, 5X Denhardt solution, 2% SDS, 100 μg/ml denatured salmon sperm DNA). The single-stranded RNA probe was removed with RNase A (10 μg/ml) at 37° C. for 30 min. The immunological detection of the digoxigenin-labeled RNA probe was performed using alkaline phosphatase-conjugated anti-digoxigenin antibody (Boehringer Mannheim) at 1:200 and standard reagents for alkaline phosphatase.

EXAMPLE 4

Nuclease S1 Protection Analysis

S1 nuclease protection analysis of EAAT 2 mRNA (FIG. 16C; described below) also provided evidence that the aberrant splicing EAAT 2 transcripts of Example 1 were present in vivo. Northern analysis of EAAT 2 mRNA was difficult to use for this purpose because the size of normal EAAT 2 mRNA is about 11 Kb and the truncated transcript would only be ~1–2 Kb smaller. Therefore, it would be difficult to identify these truncated transcripts from full length transcript using this method.

Figure 16A:
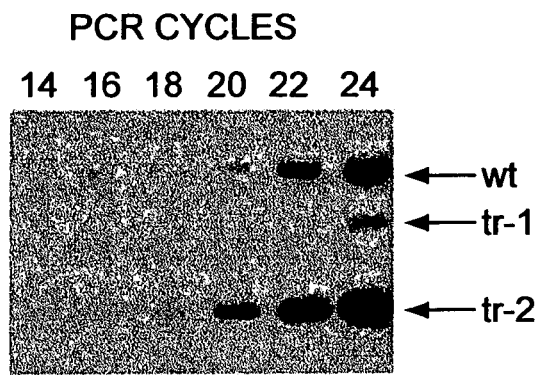
FIG. 16A is a representation of a Southern blot of RT-PCR reactions. PCR reaction products from different amplification cycles were subjected to Southern blot analysis using an oligonucleotide probe located 3' end of the PCR fragment, wt, wild-type EAAT 2; tr-1 and tr-2, two truncated aberrant species.
Figure 16B:
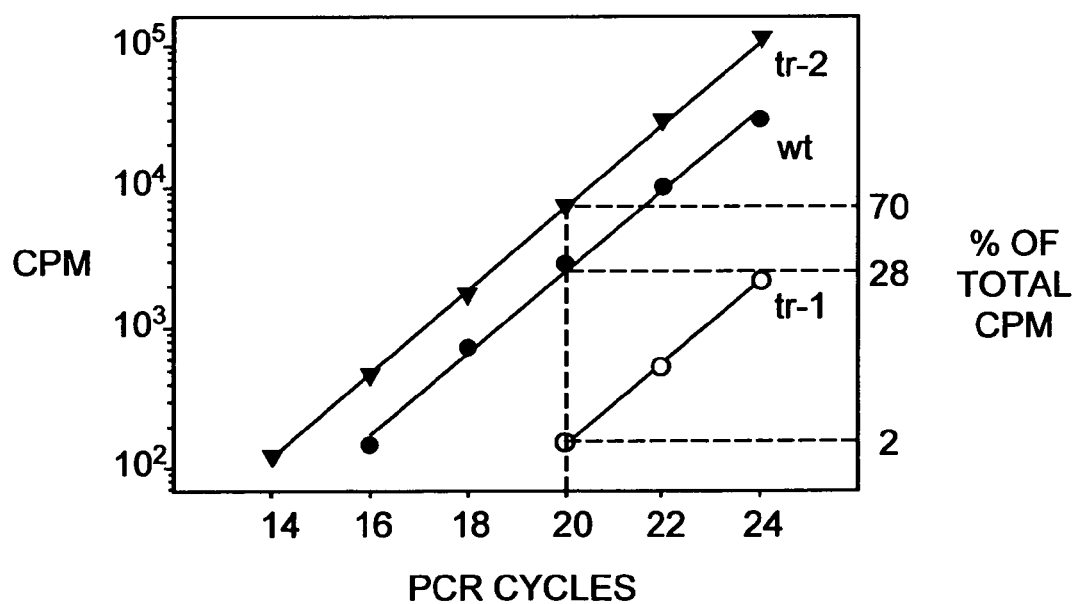
FIG. 16B is a graph showing quantitative analysis of aberrant EAAT 2 mRNA in ALS motor cortex.
Figure 16C:
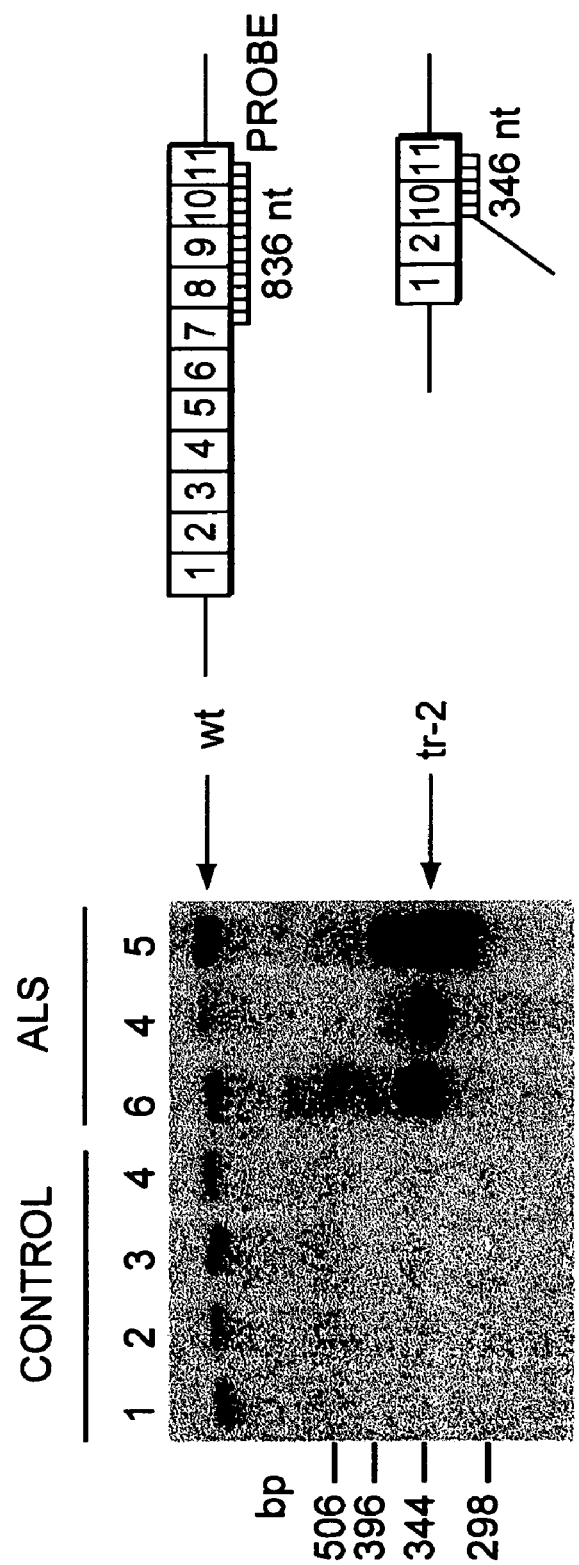
FIG. 16C is a representation of a Southern blot of an S1 nuclease analysis of EAAT 2 mRNA. A schematic representation of the probe, the wild-type mRNA, and the aberrantly spliced mRNA (tr-2) are shown on the right.

FIG. 16C shows an S1 nuclease protection analysis of EAAT 2 mRNA using a 836 base single strand DNA probe, located at 3' end of the coding region. The protection fragments were subjected to Southern blot analysis using an oligonucleotide probe located 3' end of the protection fragment. As with quantitative RT-PCR, the abnormal species were abundant in the ALS specimens compared to normal EAAT 2.

S1 nuclease protection assays were conducted as follows. A 836 base single strand DNA probe was generated by asymmetry PCR using primer A and C. PCR conditions are the same as described above except 0.05 µM primer A and 0.5 µM primer C were used. The expected single strand DNA was isolated from the gel. For hybridization and S1 nuclease analysis, 0.5 pmol of single strand DNA probe was mixed with 1 µg of the mRNA sample and hybridized in a solution containing 80% formamide, 0.4 M NaCl, 40 mM piperazine-N, N'-bis (2-ethanesulfonic acid) (PIPES; pH 6.4), and 1 mM EDTA for 16 hr at 55° C. Samples were then diluted 15-fold with ice-cold S1 nuclease buffer (BRL) and treated with 0.5 U of S1 nuclease per microliter at 25° C. for 1 hr. The protected fragments were resolved by 1.5% agarose gel electrophoresis and transferred to membrane. The blot was probed with an oligonucleotide probe located at the 3' end of the protection fragment (described above) and then subjected to autoradiography.

EXAMPLE 5

Quantitative Analysis of Aberrant RNA Processing Products

To determine the abundance of the aberrant mRNA species relative to wild type EAAT 2, quantitative RT-PCR was performed using mRNA from ALS patient 4. This patient was chosen because RT-PCR studies revealed only two types of truncated transcripts (FIG. 14C). PCR reaction products from different amplification cycles were resolved by gel electrophoresis and transferred to membrane for Southern blot analysis (FIG. 16A). The amount of radioactivity recovered from the excised membrane bands was plotted as function of the number of cycles (FIG. 16B). The rates of amplification were exponential between 14 and 24 cycles for full length and truncated templates. The results revealed that full length (wild-type, wt) and truncated transcripts tr-1, and tr-2 represent 28%, 2%, and 70% of total EAAT 2 transcript, respectively. It is notable that the truncated transcript tr-2 from this patient is same as the transcript in FIG. 13B$_7$. As described below, this truncated transcript produced downregulation of normal EAAT 2 in vitro. It was found that up to 70% of total EAAT 2 transcripts were aberrant RNA processing products.

In FIG. 16B, the amounts of radioactivity recovered from the excised membrane bands in (FIG. 16A) were plotted as function of the number of cycles. The rates of amplification were exponential between 14 and 24 cycles for full length and truncated templates. More than 70% of total EAAT 2 mRNA is in the form of aberrant transcripts.

1. Nuclease Protection Assays

S1 nuclease protection assays were also performed to evaluate the relative abundance of the aberrant mRNA species found in Example 1. A 836 base single strand DNA probe, located at the 3' end of the coding region was used. The S1 nuclease-resistant fragments were resolved by gel electrophoresis and transferred to membrane. The blot was probed with an oligonucleotide probe located 3' end of the protection fragment. As shown in FIG. 4C, large amounts of <836 bp S1 nuclease-resistant fragments were observed in ALS specimens but were not seen in the control specimens. The mRNA sample from ALS patient 4 used in this experiment was the same one used for quantitative RT-PCR described above. The 346 bp S1 nuclease-resistant fragment, corresponding to the truncated transcript tr-2, represents 73% of the total protection fragments, which is in agreement with the quantitative RT-PCR results (FIG. 16B).

EXAMPLE 6

Aberrant EAAT 2 Transcripts Were Present in Sporadic ALS and Correlated with Loss of EAAT 2 Protein To evaluate the prevalence of aberrant EAAT 2 transcripts in ALS, 30 ALS specimens were screened, including spinal cord, motor cortex, and cerebellum for partial intron 7-retention and exon 9-skipping transcripts by competitive RT-PCR (FIG. 14A). An internal control was designed to amplify along with the partial intron 7-retention mRNA (FIG. 13A). Since the exon 9-skipping mRNA was 135 bp shorter than the wild-type EAAT 2 mRNA, the wild type EAAT 2 mRNA was used as an internal control for the comparative analysis of the exon 9-skipping mRNA between patients. All RT-PCR experiments were repeated 2–5 times for each specimen to verify the presence of aberrant mRNA species. Both aberrant transcripts were commonly found; 20 of the 30 ALS patients had the partial intron 7-retention mRNA and 11 of the 30 ALS patients had the exon 9-skipping mRNA. These aberrant mRNA species were only found in ALS motor cortex and/or spinal cord, but not in cerebellum. To determine the disease specificity of these aberrant mRNA species, other non-neurological and neurological disease control tissues were examined (Table 1), including tissue from neuropathogically affected and unaffected regions. The aberrant mRNA species were not found in any of the neural tissues from a total of 40 controls, including 27 non-neurological disease control specimens (12 spinal cord and 27 motor cortex), 8 spinal muscular atrophy specimens (SMA-type 1) (spinal cord), 7 Alzheimer's disease specimens (7 hippocampus and 7 motor cortex), and 6 Huntington's disease specimens (6 caudate and 6 motor cortex). The control tissues were matched for age and postmortem delay (Table 1). Table 1 is shown below.

TABLE 1

ALS and control populations used for the analysis of EAAT 2 mutations.

| Group | # of patients | M/F | Age at death (mean yr SE) | | Post-mortem delay (hr) (mean SE) | |
|---|---|---|---|---|---|---|
| ALS | 30 | 23/7 | 60.4 | 2.1 | 7.3 | 0.8 |
| Non-neurological disease | 25 | 15/19 | 65.2 | 2.2 | 10.4 | 0.6 |
| SMA* | 8 | 3/5 | 6.6 | 1.0 (mo) | 9.3 | 1.8 |
| Alzheimer□s disease | 7 | 4/3 | 74.8 | 2.1 | 8.2 | 0.6 |
| Huntington□s disease | 6 | 2/4 | 59.3 | 4.9 | 11.9 | 0.7 |

*SMA = spinal muscular atrophy, type 1

Figure 17A:
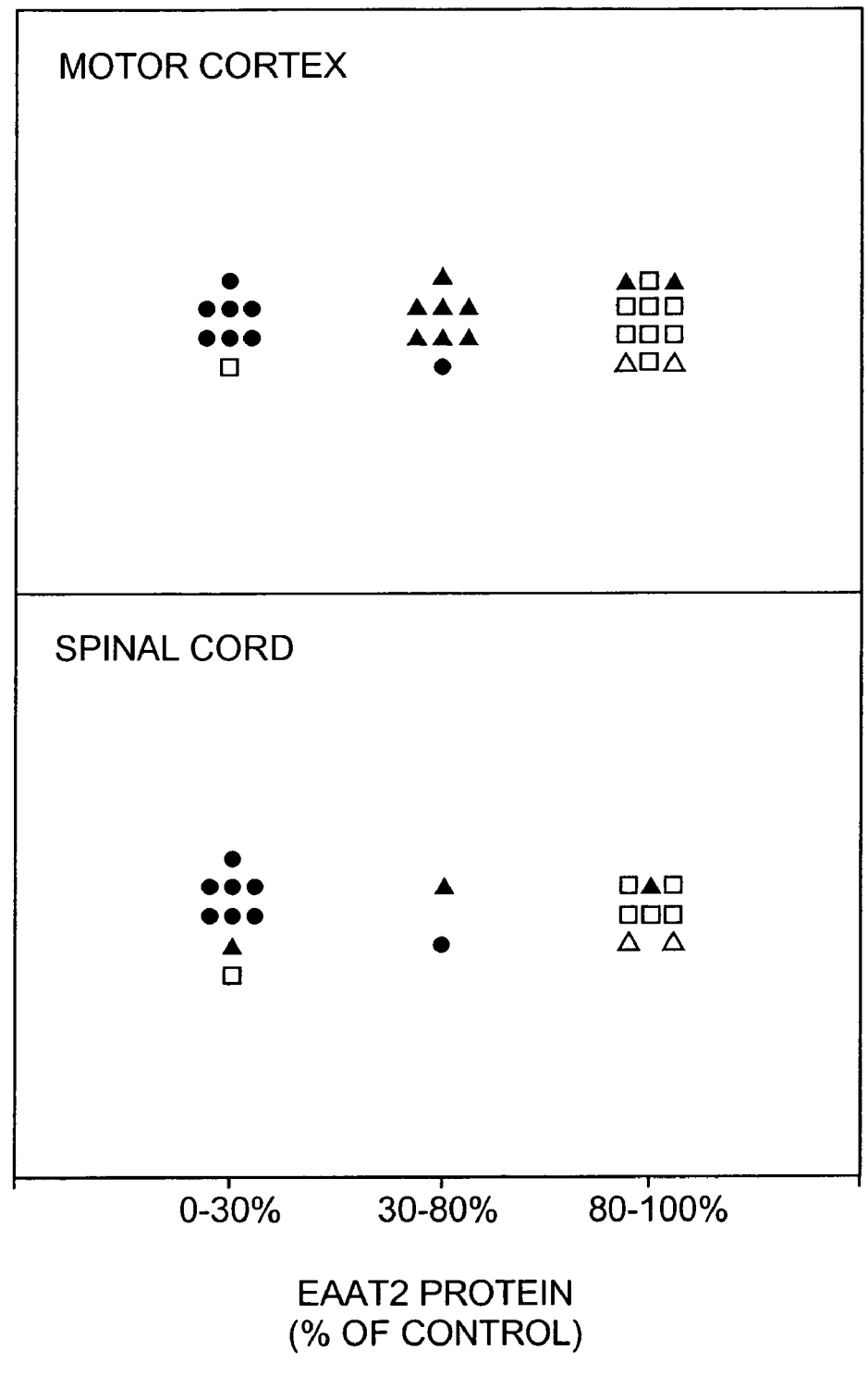
FIG. 17A–17C are graphs showing that aberrant EAAT 2 mRNA species correlate with the loss of EAAT 2 protein.
Figure 17B:
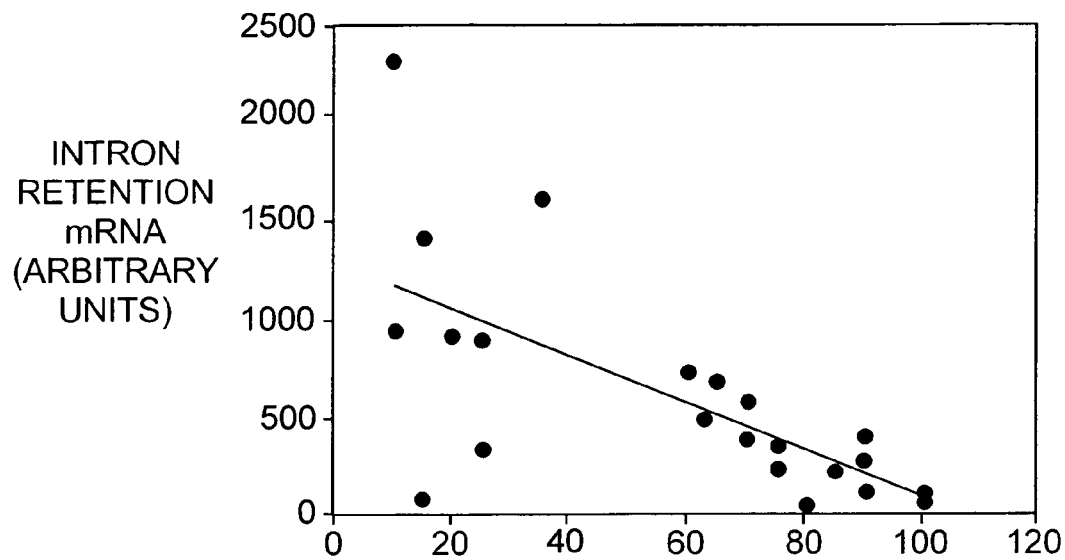
Figure 17C:
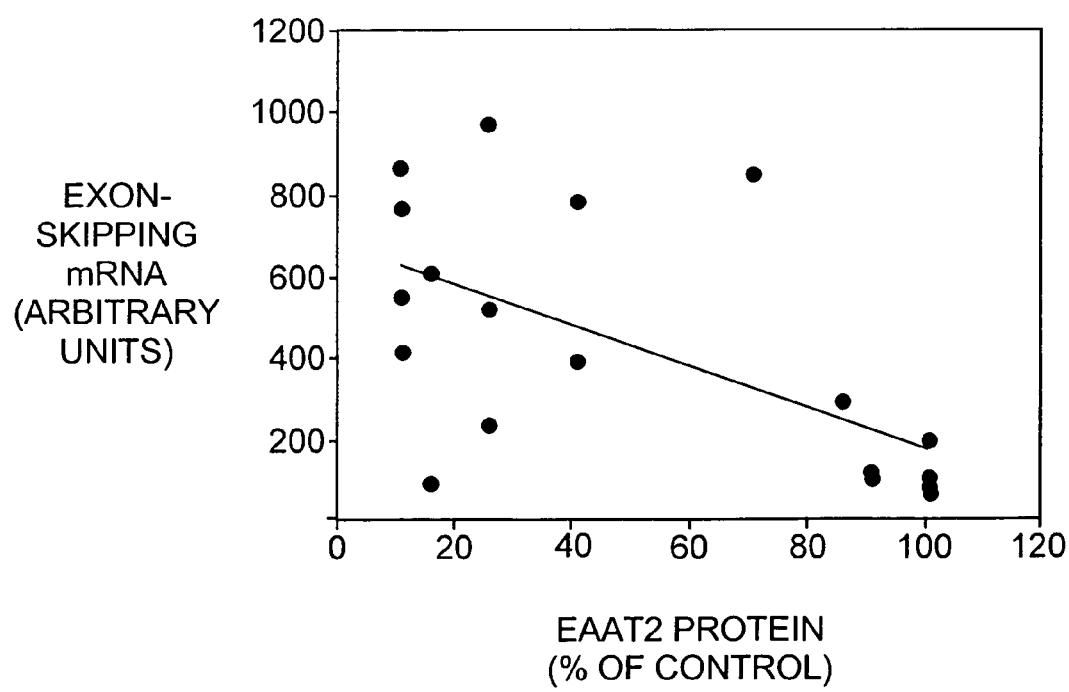

In FIG. 17A, identification of both (solid circle) partial intron 7-retention and exon 9-skipping mRNA species in the same tissue samples was typically associated with a large loss of EAAT 2 protein, while the presence of partial intron 7-retention alone (solid triangle) or trace amounts of partial intron 7-retention mRNA sequence (open triangle) was associated with moderate to little loss of EAAT 2 protein. Absence of the abnormally processed mRNA (open square) was associated with normal levels of EAAT 2 protein. In FIG. 17B, the amounts of partial intron 7-retention and exon 9-skipping mRNA species in spinal cord and motor cortex were inversely correlated with the amount of EAAT 2 protein.

More particularly, the presence of abnormal mRNA was significantly ($P<0.001$) correlated with the loss of EAAT 2 protein. ALS specimens from motor cortex or spinal cord that had very low levels of EAAT 2 protein (<30% of control) contained both partial intron7-retention and exon 9-skipping transcripts (FIG. 17A). Eight out of 30 ALS patients had both partial intron 7-retention and exon 9-skipping mRNA. An intermediate loss of EAAT 2 protein in neural tissue, 30–80% of control levels, was associated with the presence of the partial intron 7-retention mRNA alone. In addition, the loss of EAAT 2 protein was inversely correlated with the amounts of either the exon 9-skipping ($r_s$=0.81, $P<0.001$) or the partial intron 7-retention mRNA ($r_s$=0.62, $P<0.001$; FIG. 17B). Although the presence of aberrant mRNA species appeared to correlate with a loss of protein, rarely patients with a loss of EAAT 2 did not have either of these aberrant RNA. In those cases, the loss of protein could be due to other, as additional variants in EAAT 2 mRNA. Alternatively, other mechanisms known to lead to degradation of glutamate transporter proteins, e.g. oxidative stress, could have resulted in a loss of EAAT 2 (Trotti et al. (1996) *J. Biol. Chem.* 271, 5975; Volterra et al. (1994) *Mol. Pharmacol*, 46, 986).

The presence of the aberrant mRNA species did not correlate with the clinical presentation (spinal versus bulbar onset) of the disease in ALS patients. ALS patients with altered EAAT 2 mRNA species had a tendency toward shorter survival (17+/−2.9 (SEM) months) when compared to the overall average for ALS of 2–5 years (Kuncl et al. (1992). *Motor neuron diseases. In diseases of the Nervous System*, A. K. Asbury, G. M. McKhann, and W. I. McDonald, ods. (Philadelphia: W.B. Saunders). pp. 1179–1208). But not when compared to the ALS patients in this study without aberrant mRNA species (23+/−4.8 (SEM) months).

EXAMPLE 7

Detection of Aberrant EAAT 2 Transcripts in Cerebrospinal Fluid

Cerebrospinal fluid (CSF) was also examined for the presence of the exon 9-skipping transcript in ALS and control specimens (FIG. 14B). All specimens were processed identically. Control CSF was obtained from patients with neurological diagnoses that included: multiple sclerosis, normal pressure hydrocephalus, hepatic encephalopathy, migraine headache, subarachnoid hemorrhage, stroke, epilepsy, ataxia, CNS vasculitis, and dementia. The exon 9-skipping mRNA was not detected in the 38 control specimens, but was detected in 12 out of 18 (66%) ALS specimens. In addition, in four ALS cases (Table 2), CSF obtained during diagnostic evaluation and brain tissue obtained at autopsy were available from the same patients. In those patients, CSF was collected 25.5+/−6 (SEM) months prior to death. In all cases, the presence of the exon 9-skipping mRNA was detected in both ante-mortem CSF and post-mortem brain or spinal cord tissue.

FIG. 14B showed that the exon 9-skipping EAAT 2 mRNA is present in some ALS cerebrospinal fluid specimens. FIG. 14C showed RT-PCR for full length EAAT 2 reveals multiple truncated transcripts in ALS but not in controls. The aberrant species were present in motor cortex, but not cerebellum (Cblm) or hippocampus (Hipp).

Table 2 is shown below.

TABLE 2

Exon-9 skipping EAAT 2 species are present in ALS CSF years prior to death: Examination of CSF and post mortem brain specimens.

| Patient | Age (at death) | Disease Duration (mo) | CSF collection: time before death (mo) | Exon 9-skipping EAAT 2 (RT-PCR) CSF | Brain |
|---|---|---|---|---|---|
| 1 | 44 | 39 | 27 | + | + |
| 2 | 52 | 46 | 41 | + | + |
| 3 | 62 | 15 | 12 | + | + |
| 4 | 63 | 22 | 22 | − | − |

+ exon 9-skipping EAAT 2 present in sample;
− exon 9-skipping species not detectable.

EXAMPLE 8

Proteins Translated from Aberrant Transcripts are Unstable and/or Cause Down-Regulation of Normal EAAT 2 In Vitro To determine if proteins translated from these aberrant EAAT 2 transcripts could be identified in the ALS post mortem tissue, ALS motor cortex was analyzed for a carboxy-terminal truncated EAAT 2 protein (the presumed protein product of the partial intron 7-retention transcript) by Western blotting with amino-terminal oligopeptide antibodies to human EAAT 2 protein (Rothstein et al., 1995 supra). Previous studies have shown that the amino terminal antibody can recognize wild-type EAAT 2 in human tissue. However, using this antibody, no immunoreactive band with the expected size of the truncated EAAT 2 protein was detected. The protein from the exon 9-skipping transcript was also investigated in ALS tissue, using oligopeptide antibodies to the amino acid sequence spanning the deletion site. Again, no immunoreactive band was detected. The inability to detect the aberrant EAAT 2 proteins could be due to at least two possibilities: 1) the aberrant EAAT 2 transcripts could be very unstable and/or rapidly degraded in post mortem tissue, or 2) may not be detectable with the available antibodies. They also may affect normal EAAT 2 function.

1. Glutamate Transport Assays

Figure 18A:
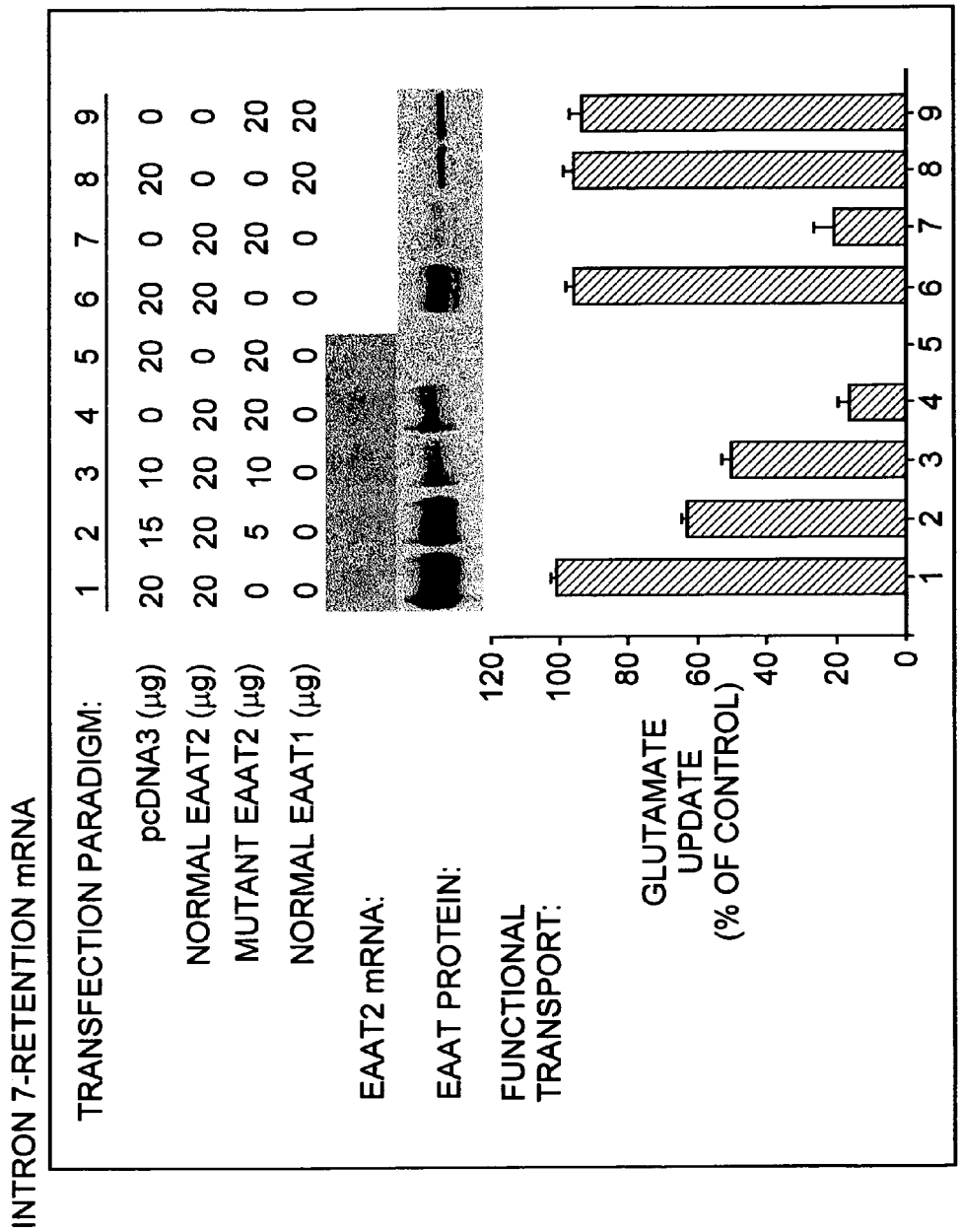
FIG. 18A is a diagram showing glutamate uptake related to various transfection paradigms using cDNA for the intron 7-retention mRNA. The diagram includes representations of a Southern blot and a Western blot of expressed EAAT 2 mRNA and protein, respectively.

To evaluate the properties of these abnormal transcripts, EAAT 2 cDNA was transiently expressed in COS7 cells. EAAT 2 protein was quantitated 72 hours post-transfection by Western blotting and activity of the transporter was measured by a sodium-dependent, $^3$H-glutamate transport assay (Rothstein et al. (1992) *N. Engl. J. Med.* 326, 1464; Rothstein et al., (1995), supra). Wild-type EAAT 2 protein was detected by a carboxy-terminal EAAT 2 antibody (FIG. 18A, lane 1) as well as evidence of glutamate transport. Wild-type EAAT 2 was not detected by the available amino-terminal antibody. As expected, predicted truncated protein synthesized from the partial intron 7-retention cDNA was not detected by this carboxy-terminal antibody (FIG. 18A, lane 5). Nevertheless, there was evidence that the partial intron 7-retention EAAT 2 cDNA was expressed by the COS7 cells because the partial intron 7-retention mRNA was detected in the transfected cells by Northern blotting and RT-PCR. No glutamate transport was observed in COS7 cells transfected with the partial intron 7-retention cDNA.

When the partial intron 7-retention cDNA was co-transfected with the normal EAAT 2 cDNA into COS7 cells, there was a progressive decrease in the level of normal EAAT 2 protein (FIG. 18A, lanes 2–4). However, the levels of wild type EAAT 2 mRNA, using Northern analysis, were not deceased by the partial intron 7-retention cDNA (FIG. 18A, lanes 2–4). Glutamate transport also decreased in parallel with the loss of EAAT 2 protein (FIG. 18A, lanes 2–4). The same results were obtained when the partial intron 7-retention cDNA was co-expressed in HeLa cells (FIG. 18A, lanes 6–7). These co-expression studies suggest that the partial intron7-retention cDNA could dominantly down-regulate EAAT 2 protein. This effect was specific for EAAT 2; co-expression of the intron-retention cDNA with wild-type EAAT1, EAAT3 or EAAT4 cDNA had no effect on either the astroglial subtype EAAT1 (FIG. 18A, lanes 8 and 9), or the neuronal subtypes EAAT3 and EAAT4 protein or glutamate transport. This effect is not due to the promoter competition between wild type and partial intron 7-retention cDNA because (i) the levels of wild type EAAT 2 mRNA were not decreased and (ii) this effect was not observed in other subtypes of glutamate transporters with the same vector and transfection conditions.

The exon 9-skipping EAAT 2 cDNA was also expressed in COS7 cells. Although the protein was not detected by Western blotting (FIG. 18B, lane 2), the mRNA was detected in the transfected COS7 cells by RT-PCR. However, no glutamate transport was observed in the transfected COS7 cells by sodium-dependent, $^3$H-glutamate transport assay. Notably, in this paradigm, the exon 9-skipping cDNA had no effect on the expression of wild-type EAAT 2 protein or glutamate transport (FIG. 18B, lane 3).

Figure 18B:
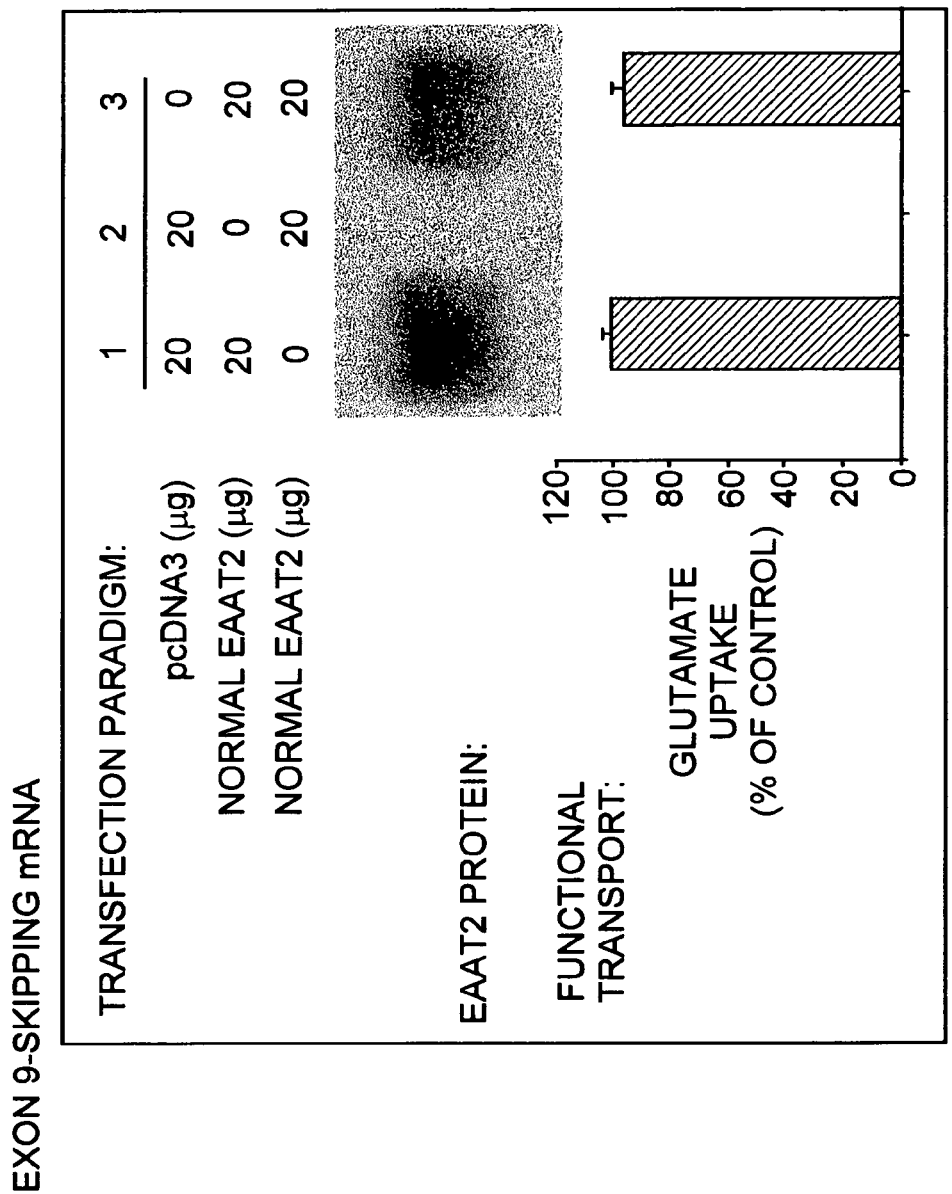
FIG. 18B is a diagram showing glutamate uptake related to various transfection paradigms using cDNA for the intron 7-retention mRNA. The diagram includes a representation of a Western blot showing expressed EAAT 2 protein.

As noted, FIGS. 18A and 18B depict transient expression of the partial intron 7-retention and exon 9-skipping EAAT 2 cDNA in COS7 cells and in HeLa cells. Different combinations of indicated plasmids were transfected into COS7 cells (FIG. 18A, paradigm 1–5 and 8–9; FIG. 18B, paradigm 1–3) or HeLa cells (FIG. 16A, paradigm 6–7) by electroporation. After 72 hours, some transfected cells were used to quantitate expressed EAAT 2 or EAAT1 protein by immunoblotting using carboxy-terminal oligopeptide antibodies to EAAT 2 or EAAT1 protein, or EAAT 2 mRNA expression by Northern blot. Others were used to measure functional EAAT 2 or EAAT1 by sodium-dependent, $^3$H-glutamate transport assay. (FIG. 18A). The partial intron 7-retention EAAT 2 cDNA produced a negative effect on the normal EAAT 2 protein level and glutamate transport (paradigm 1–7), but had no effect on EAAT 2 mRNA levels (paradigm 1–5), EAAT1 protein levels (paradigm 8,9) or EAAT1 glutamate transport (paradigm 8,9).

In FIG. 18B, the exon 9-skipping EAAT 2 species had no effect on EAAT 2 protein expression (paradigm 3) or on wild type glutamate transport (paradigm 3). All aberrant or wild-type EAAT 2 (EAAT1) cDNAs were in the same vector (pcDNA3).

Several mechanisms could account mutant protein interference with wild-type EAAT 2 activity. More information can be learned about glutamate transporter membrane organization or trafficking. Some data suggests that under normal conditions, EAAT 2 monomers may self-associate to form homomeric multimers in vivo (Haugeto et al. (1996) *J. Biol. Chem.* 271, 27715). Without wishing to be bound to any specific theory, it appears that heteromers composed of mutant truncated EAAT 2 and wild-type EAAT 2 protein subunits undergo rapid degradation. This theory could explain the loss of EAAT 2 in COS7 cell expression experiments and in ALS. Examples of such dominant-negative interactions between multimeric proteins is not uncommon. For example, in mice, a retained intron for the vitamin D receptor, leads to a truncated protein; this protein subsequently forms heterodimers with retinoic acid receptors, ultimately dominantly down regulating vitamin D signaling (Ebihara et al. (1996). *Mol. Cell. Biol.* 16, 33393).

2. Aberrant EAAT 2 cDNA Expression and Translation in Cells

Figure 19A:
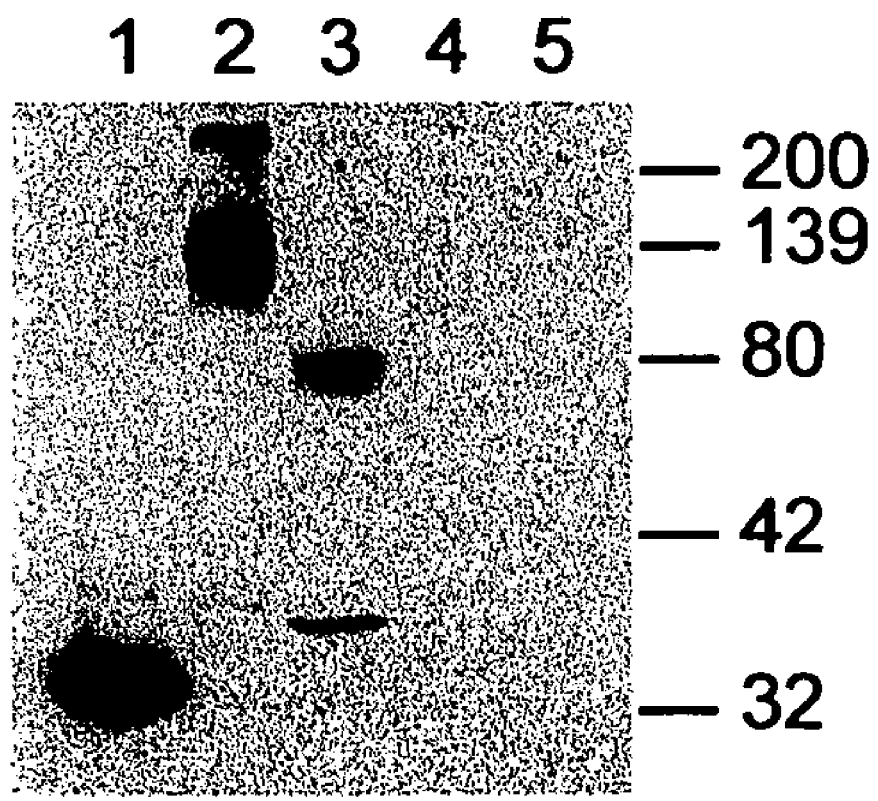
FIG. 19A is a representation of an immunoblot of COS7 cells expressing EAAT 2-GFP fusion protein using anti-GFP antibody.
Figure 19B:
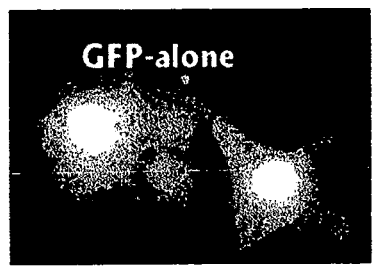
FIGS. 19B–19I are fluorescence photomicrographs showing expression of normal and aberrant EAAT 2 fused with green-fluorescent protein (GFP) in COS7 cells. Magnification=400×.

To confirm that the aberrant EAAT 2 cDNAs were expressed and translated, we constructed chimeric genes to encode C-terminal fusions of wild-type or mutant EAAT 2 to green-fluorescent protein (GFP). These constructs were expressed in COS7 cells and all produced similar levels of mRNA by Northern blotting. The wild-type EAAT 2-GFP transfected cells had normal $^3$H-glutamate transport activity when compared to non-GFP EAAT 2 transfected cells. Expression of fusion proteins was examined by Western blotting using anti-GFP antibodies (FIG. 19A). Both the partial intron 7-retention (FIG. 19A, lane 3) and the exon 9-skipping (FIG. 19A, lane 4) EAAT 2-GFP proteins were expressed at the expected lower molecular weights. Furthermore, the mutant EAAT 2-GFPs appeared to be unstable compared to the wild-type EAAT 2-GFP (FIG. 19A, lane 2) as judged by the presence of less protein and multiple lower molecular weight species (FIG. 19A, lanes 3 and 4).

As noted above, FIG. 19A is an immunoblot of COS7 cells expressing EAAT 2-GFP fusion protein using anti-GFP antibody. Lane 1, pEGFP vector; lane 2, wild-type EAAT 2-GFP; Lane 3, partial intron 7-retention EAAT 2-GFP; Lane 4, exon 9-skipping EAAT 2-GFP; lane 5, COS7 cells alone. The partial intron 7-retention and exon 9-skipping mRNA produced truncated, unstable proteins.

2. Cellular Localization of Aberrant EAAT 2 Fusion Proteins

Figure 19C:
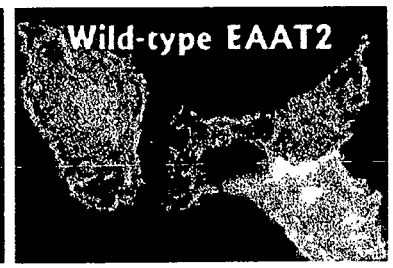
Figure 19D:
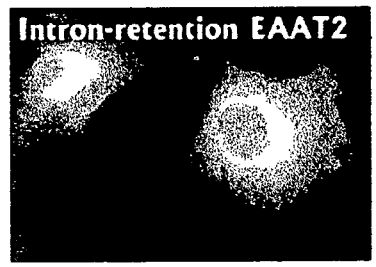
Figure 19E:
Figure 19F:
Figure 19G:
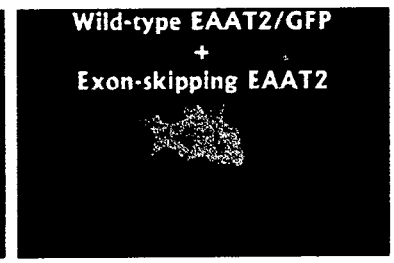
Figure 19H:
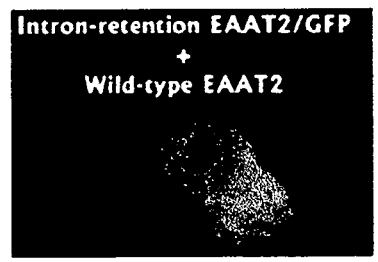
Figure 19I:
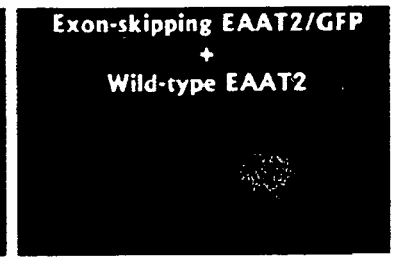

The cellular localization of the fusion proteins was then examined by fluorescent microscopy. Wild-type EAAT 2-GFP was preferentially localized to the cell surface (FIG. 19C). However, both the partial intron 7-retention and the exon 9-skipping EAAT 2-GFP fusion proteins were restricted to the cytoplasm, often peri-nuclear (FIGS. 19D–E) and occasionally in lysosomes. When wild-type EAAT 2-GFP was co-expressed with the partial intron 7-retention EAAT 2 (not GFP-labeled), the wild-type protein was found largely confined to the cytoplasm, with occasional cell membrane staining (FIG. 19F). The same results were observed from co-expression of partial intron 7-retention EAAT 2-GFP with wild-type EAAT 2 (not GFP-labeled) (FIG. 19). These results suggest that the partial intron 7-retention EAAT 2 protein may interfere with normal EAAT 2 protein complex assembly or trafficking. These results were not seen with the exon-9 skipping EAAT 2, which did not interfere with wild-type EAAT 2 localization (FIG. 19G). Importantly, the abnormal protein localization is probably not due to the influence of the GFP fusion because (i) wild-type EAAT 2-GFP transfected cells had normal glutamate uptake, (ii) the wild-type-GFP protein was localized on the cell surface when expressed alone or with the exon-9 skipping EAAT 2 (FIG. 19), and (iii) the partial intron 7-retention EAAT 2 (not GFP-labeled) still interfered with the wild-type EAAT 2 protein trafficking to the cell membrane.

As noted, FIGS. 19B–19I show a normal and aberrant EAAT 2 protein in COS7 cells. COS7 cells expressing GFP, wild-type EAAT 2-GFP, partial intron 7-retention EAAT 2-GFP, or exon 9-skipping EAAT 2-GFP proteins were examined by fluorescent microscopy. Aberrant proteins (exon-9 skipping-GFP, partial intron-7-retention-GFP expressed alone or with wild-type EAAT 2) were largely confined to the cytoplasm, compared to normal surface membrane localization of EAAT 2. A co-expression of the GFP-labeled EAAT 2 with the unlabeled partial-intron-7-retention EAAT 2 revealed that the aberrant protein interfered with the localization of wild type protein in the surface membrane. All transfection experiments were repeated five times in triplicate. $^3$H-glutamate transport expressed as mean transport+SE compared to control.

Eight other aberrant cDNAs were also expressed (described in FIG. 13B) in COS7 cells. Two of them, shown at FIGS. 13B$_4$ and 13B$_7$ also showed a dominant down-regulation effect on normal EAAT 2 activity and protein expression, like the partial intron 7-retention EAAT 2 cDNA, while the remaining cDNAs were unstable and inactive, like the exon 9-skipping EAAT 2 cDNA.

Immunoblots were performed as described previously (Rothstein et al., (1995) supra) on 4–25 µg of crude homogenate from motor cortex or from homogenized transfected COS7 cells grown on 75 mm plastic culture plates (CoStar), with affinity-purified polyclonal antibodies to the carboxyl-terminal region of EAAT 2 (Rothstein et al., (1995) supra) or to green fluorescent protein (GFP) (1:2000; Clontech). Glutamate transport was measured as described (Rothstein et al., (1992) supra) except using intact COS7 cells grown on 30 mm, 6 well plates (CoStar).

Wild-type as well as aberrant cDNA fragments were cloned into a eukaryotic expression vector (pcDNA3). The constructed plasmids were then transfected into COS7 cells or HeLa cells by electroporation. Electroporation (Bio Rad "Gene Pulser II" 300V at 500 µF) was performed on 1×10$^7$ cells in a solution of DMEM containing 500 µg of salmon sperm DNA along with the pcDNA3 plasmid containing the transporter subtype.

For construction of EAAT 2-GFP fusion gene, wild-type or aberrant EAAT 2 cDNA in pcDNA3 was amplified by PCR using (+) strand T7 primer and (−) strand primer (for wild-type and exon-skipping mutant using 5'-GGATC-CCGGGCCCTTTCTCACGTTTCCAAGG-3' (SEQ ID NO: 22); for partial intron 7-retention species using 5'-GGATCCCGGGCCCCCTGGAAGCGGTGCCCAG-3' (SEQ ID NO: 23). To create a restriction site for cloning purposes, we added a 13 sequence (shown underlined) at 5'-ends of the primer to create Apa I. The resultant PCR products were digested with EcoR I and Apa I and then cloned into the N-terminus of GFP gene in pEGFP-N2 vector (Novagen). Sequences of the chimeric genes were checked at their fusion sites.

In general, examples 1 to 8 show that loss of EAAT 2 protein in ALS is due to aberrant EAAT 2 transcripts. In particular, functional glutamate transport was found to be deficient in ALS and a substantial proportion of patients with sporadic disease were found to have a large loss of the EAAT 2 glutamate transporter protein. Without wishing to be bound to any particular theory, the examples indicate that the loss of EAAT 2 protein in ALS is due to aberrant EAAT 2 mRNA and is a consequence of abnormal RNA splicing.

Significantly, the aberrant EAAT 2 mRNAs described in the examples were restricted to motor cortex and spinal cord, the primary regions of neurodegeneration. Loss of EAAT 2 or the presence of aberrant EAAT 2 mRNA species in a subset of ALS patients was not found. All of the patients had pathological confirmation of motor neuron loss. Neither were they found in other neurodegenerative diseases, such as SMA, Alzheimer's or Huntington's disease, which are also characterized by slow loss of neurons (including motor neurons) and astrogliosis. But see Example 9 below. The aberrant mRNA species were also detected in patient cerebrospinal fluid up to 4 years prior to death. The subsequent loss of EAAT 2 could act to propagate motor neuron degeneration in ALS. The clinical efficacy of anti-glutamate drugs in ALS and transgenic models of ALS (Bensimon et al. (1994) *N. Engl. J. Med.* 330: 585; Gurney et al. (1996) *Ann. Neurol.* 39, 147; Lacomblez et al. (1996) *Lancet* 347: 1425) support the notion that glutamate-mediated toxicity, in part due to the loss of EAAT 2, can contribute to the pathogenesis of ALS Accordingly, the aberrant mRNA species are not a result of motor neuron loss or post-mortem artifact.

EXAMPLE 9

Detection of Aberrant mRNA EAAT 2 mRNA Transcripts in AD

Aberrant EAAT 2 transcripts were not found in about seven (7) Alzheimer's disease specimens including hippocampus (typically, the most affected area in AD) and motor cortex. However, aberrant EAAT 2 transcripts could be found in the frontal cortex of AD patients. It is recognized that the frontal cortex is also affected in AD. The aberrant EAAT 2 transcripts discovered include the partial intron 7-retention sequence. See FIG. 2 and SEQ ID NO: 3. It is believed that the aberrant EAAT 2 transcripts are also present in at least some AD patients. A loss of EAAT 2 protein has been found in some AD patients. See *J. of Neuropath. and Experimental Neurol.* 56:901.

The invention has been described in detail with reference to preferred embodiments thereof. However, it will be appreciated that those skilled in the art, upon consideration of this disclosure, may make modification and improvements within the spirit and scope of the invention as set forth in the following claims.

The invention claimed is:

1. An isolated nucleic acid sequence selected from the group consisting of SEQ ID No. 3, 5, 6, 7, 8, 9, 10, 11, 12 and 13.

2. A recombinant vector comprising any one of the isolated nucleic acid sequences of claim 1.

3. An isolated host cell comprising the vector according to claim 2.

4. A method for producing a polypeptide encoded by an aberrant EAAT 2 mRNA comprising:
   a) introducing an isolated nucleic acid comprising a sequence encoding a polypeptide, wherein the polypeptide is encoded by a sequence selected from the group consisting of any one of SEQ ID NO. 3 and 5–13 into a host cell; and
   b) culturing the host cell, thereby producing said polypeptide.

5. A kit comprising the isolated nucleic acid of claim 1.

6. A kit comprising the recombinant vector of claim 2.

7. A kit comprising the host cell of claim 3.

* * * * *